United States Patent
De La Rosa et al.

(10) Patent No.: US 10,927,078 B2
(45) Date of Patent: Feb. 23, 2021

(54) MODULATORS OF INDOLEAMINE 2,3-DIOXYGENASE

(71) Applicant: GLAXOSMITHKLINE INTELLECTUAL PROPERTY DEVELOPMENT LIMITED, Brentford (GB)

(72) Inventors: Martha Alicia De La Rosa, Research Triangle Park, NC (US); Wieslaw Mieczyslaw Kazmierski, Research Triangle Park, NC (US); Yoshiaki Washio, Stevenage (GB)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

(21) Appl. No.: 16/618,852

(22) PCT Filed: Jun. 27, 2018

(86) PCT No.: PCT/IB2018/054760
§ 371 (c)(1),
(2) Date: Dec. 3, 2019

(87) PCT Pub. No.: WO2019/003141
PCT Pub. Date: Jan. 3, 2019

(65) Prior Publication Data
US 2020/0165201 A1  May 28, 2020

Related U.S. Application Data

(60) Provisional application No. 62/566,638, filed on Oct. 2, 2017, provisional application No. 62/525,879, filed on Jun. 28, 2017.

(51) Int. Cl.
| | | |
|---|---|---|
| *C07D 211/26* | (2006.01) | |
| *C07D 401/12* | (2006.01) | |
| *C07D 409/12* | (2006.01) | |
| *C07D 409/14* | (2006.01) | |

(52) U.S. Cl.
CPC .......... *C07D 211/26* (2013.01); *C07D 401/12* (2013.01); *C07D 409/12* (2013.01); *C07D 409/14* (2013.01)

(58) Field of Classification Search
CPC .. C07D 211/26; C07D 401/12; C07D 409/12; C07D 409/14
See application file for complete search history.

(56) References Cited

U.S. PATENT DOCUMENTS

| | | | | |
|---|---|---|---|---|
| 2004/0204341 A1* | 10/2004 | Allen | ...................... | A61K 31/18 514/408 |
| 2008/0125470 A1 | 5/2008 | Combs | | |

FOREIGN PATENT DOCUMENTS

| | | |
|---|---|---|
| WO | WO 02/080928 A1 | 10/2002 |

OTHER PUBLICATIONS

Database Registry, Database Accession Nos. 1324707-70-1 to 1235004-10-0, 21 pages.
Database Registry [Online], Chemical Abstracts Service, Columbus, OH, Jul. 9, 2015, XP002784228, Database Accession No. 1797971-62-0, 1797793-94-2, 1797647-67-6.
Database Registry [Online], Chemical Abstracts Service, Columbus, OH, Jul. 8, 2015, XP002784229, Database Accession No. 1797213-34-3.
Database Registry [Online], Chemical Abstracts Service, Columbus, OH, Aug. 30, 2011, XP002784230, Database Accession No. 1325689-71-1.
Database Registry [Online], Chemical Abstracts Service, Columbus, OH, Aug. 4, 2010, XP002784231, Database Accession No. 1234921-21-1.
R. Dolusic. "Indoleamine 2,3-dioxygenase inhibitors: a patent review (2008-2012)". Expert Opin. Ther. Patents, 23(10): 1367-1381 (Aug. 30, 2013).

\* cited by examiner

*Primary Examiner* — Timothy R Rozof
(74) *Attorney, Agent, or Firm* — Robert H. Brink; Duke M. Fitch; Edward R. Gimmi

(57) ABSTRACT

Provided are IDO inhibitor compounds of Formula I and pharmaceutically acceptable salts thereof, their pharmaceutical compositions, their methods of preparation, and methods for their use in the prevention and/or treatment of diseases.

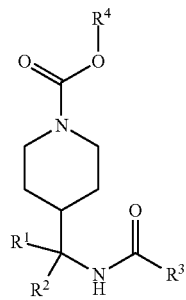

Formula I

16 Claims, No Drawings

MODULATORS OF INDOLEAMINE 2,3-DIOXYGENASE

This application is a § 371 of International Application No. PCT/IB2018/054760, filed 27 Jun. 2018, which claims the benefit of U.S. Provisional Application Nos. 62/566,638, filed 2 Oct. 2017, and 62/525,879, filed 28 Jun. 2017.

FIELD OF THE INVENTION

Compounds, methods and pharmaceutical compositions for the prevention and/or treatment of HIV; including the prevention of the progression of AIDS and general immunosuppression, by administering certain indoleamine 2,3-dioxygenase compounds in therapeutically effective amounts are disclosed. Methods for preparing such compounds and methods of using the compounds and pharmaceutical compositions thereof are also disclosed.

BACKGROUND OF THE INVENTION

Indoleamine-2,3-dioxygenase 1 (IDO1) is a heme-containing enzyme that catalyzes the oxidation of the indole ring of tryptophan to produce N-formyl kynurenine, which is rapidly and constitutively converted to kynurenine (Kyn) and a series of downstream metabolites. IDO1 is the rate limiting step of this kynurenine pathway of tryptophan metabolism and expression of IDO1 is inducible in the context of inflammation. Stimuli that induce IDO1 include viral or bacterial products, or inflammatory cytokines associated with infection, tumors, or sterile tissue damage. Kyn and several downstream metabolites are immunosuppressive: Kyn is antiproliferative and proapoptotic to T cells and NK cells (Munn, Shafizadeh et al. 1999, Frumento, Rotondo et al. 2002) while metabolites such as 3-hydroxy anthranilic acid (3-HAA) or the 3-HAA oxidative dimerization product cinnabarinic acid (CA) inhibit phagocyte function (Sekkai, Guittet et al. 1997), and induce the differentiation of immunosuppressive regulatory T cells (Treg) while inhibiting the differentiation of gut-protective IL-17 or IL-22-producing CD4+ T cells (Th17 and Th22)(Favre, Mold et al. 2010). IDO1 induction, among other mechanisms, is likely important in limiting immunopathology during active immune responses, in promoting the resolution of immune responses, and in promoting fetal tolerance. However in chronic settings, such as cancer, or chronic viral or bacterial infection, IDO1 activity prevents clearance of tumor or pathogen and if activity is systemic, IDO1 activity may result in systemic immune dysfunction (Boasso and Shearer 2008, Li, Huang et al. 2012). In addition to these immunomodulatory effects, metabolites of IDO1 such as Kyn and quinolinic acid are also known to be neurotoxic and are observed to be elevated in several conditions of neurological dysfunction and depression. As such, IDO1 is a therapeutic target for inhibition in a broad array of indications, such as to promote tumor clearance, enable clearance of intractable viral or bacterial infections, decrease systemic immune dysfunction manifest as persistent inflammation during HIV infection or immunosuppression during sepsis, and prevent or reverse neurological conditions.

IDO1 and Persistent Inflammation in HIV Infection:

Despite the success of antiretroviral therapy (ART) in suppressing HIV replication and decreasing the incidence of AIDS-related conditions, HIV-infected patients on ART have a higher incidence of non-AIDS morbidities and mortality than their uninfected peers. These non-AIDS conditions include cancer, cardiovascular disease, osteoporosis, liver disease, kidney disease, frailty, and neurocognitive dysfunction (Deeks 2011). Several studies indicate that non-AIDS morbidity/mortality is associated with persistent inflammation, which remains elevated in HIV-infected patients on ART as compared to peers (Deeks 2011). As such, it is hypothesized that persistent inflammation and immune dysfunction despite virologic suppression with ART is a cause of these non-AIDS-defining events (NADEs).

HIV infects and kills CD4+ T cells, with particular preference for cells like those CD4+ T cells that reside in the lymphoid tissues of the mucosal surfaces (Mattapallil, Douek et al. 2005). The loss of these cells combined with the inflammatory response to infection result in a perturbed relationship between the host and all pathogens, including HIV itself, but extending to pre-existing or acquired viral infections, fungal infections, and resident bacteria in the skin and mucosal surfaces. This dysfunctional host:pathogen relationship results in the over-reaction of the host to what would typically be minor problems as well as permitting the outgrowth of pathogens among the microbiota. The dysfunctional host:pathogen interaction therefore results in increased inflammation, which in turn leads to deeper dysfunction, driving a vicious cycle. As inflammation is thought to drive non-AIDS morbidity/mortality, the mechanisms governing the altered host:pathogen interaction are therapeutic targets.

IDO1 expression and activity are increased during untreated and treated HIV infection as well as in primate models of SIV infection (Boasso, Vaccari et al. 2007, Favre, Lederer et al. 2009, Byakwaga, Boum et al. 2014, Hunt, Sinclair et al. 2014, Tenorio, Zheng et al. 2014). IDO1 activity, as indicated by the ratio of plasma levels of enzyme substrate and product (Kyn/Tryp or K:T ratio), is associated with other markers of inflammation and is one of the strongest predictors of non-AIDS morbidity/mortality (Byakwaga, Boum et al. 2014, Hunt, Sinclair et al. 2014, Tenorio, Zheng et al. 2014). In addition, features consistent with the expected impact of increased IDO1 activity on the immune system are major features of HIV and SIV induced immune dysfunction, such as decreased T cell proliferative response to antigen and imbalance of Treg:Th17 in systemic and intestinal compartments (Favre, Lederer et al. 2009, Favre, Mold et al. 2010). As such, we and others hypothesize that IDO1 plays a role in driving the vicious cycle of immune dysfunction and inflammation associated with non-AIDS morbidity/mortality. Thus, we propose that inhibiting IDO1 will reduce inflammation and decrease the risk of NADEs in ART-suppressed HIV-infected persons.

IDO1 and Persistent Inflammation Beyond HIV

As described above, inflammation associated with treated chronic HIV infection is a likely driver of multiple end organ diseases [Deeks 2011]. However, these end organ diseases are not unique to HIV infection and are in fact the common diseases of aging that occur at earlier ages in the HIV-infected population. In the uninfected general population inflammation of unknown etiology is a major correlate of morbidity and mortality [Pinti, 2016 #88]. Indeed many of the markers of inflammation are shared, such as IL-6 and CRP. If, as hypothesized above, IDO1 contributes to persistent inflammation in the HIV-infected population by inducing immune dysfunction in the GI tract or systemic tissues, then IDO1 may also contribute to inflammation and therefore end organ diseases in the broader population. These inflammation associated end organ diseases are exemplified by cardiovascular diseases, metabolic syndrome, liver disease (NAFLD, NASH), kidney disease, osteoporosis, and neurocognitive impairment. Indeed, the IDO1 pathway has links in the literature to liver disease (Vivoli abstracts at Italian Assoc. for the Study of the Liver Conference 2015], diabetes [Baban, 2010 #89], chronic kidney disease [Schefold, 2009 #90], cardiovascular disease [Mangge, 2014 #92; Mangge, 2014 #91], as well as general aging and all cause mortality [Pertovaara, 2006 #93]. As such, inhibition of IDO1 may have application in decreasing inflammation in the general population to decrease the incidence of specific end organ diseases associated with inflammation and aging.

IDO1 and Oncology

IDO expression can be detected in a number of human cancers (for example; melanoma, pancreatic, ovarian, AML, CRC, prostate and endometrial) and correlates with poor prognosis (Munn 2011). Multiple immunosuppressive roles have been ascribed to the action of IDO, including the induction of Treg differentiation and hyper-activation, suppression of Teff immune response, and decreased DC function, all of which impair immune recognition and promote tumor growth (Munn 2011). IDO expression in human brain tumors is correlated with reduced survival. Orthotropic and transgenic glioma mouse models demonstrate a correlation between reduced IDO expression and reduced Treg infiltration and a increased long term survival (Wainwright, Balyasnikova et al. 2012). In human melanoma a high proportion of tumors (33 of 36 cases) displayed elevated IDO suggesting an important role in establishing an immunosuppressive tumor microenvironment (TME) characterized by the expansion, activation and recruitment of MDSCs in a Treg-dependent manner (Holmgaard, Zamarin et al. 2015). Additionally, host IDO expressing immune cells have been identified in the draining lymph nodes and in the tumors themselves (Mellor and Munn 2004). Hence, both tumor and host-derived IDO are believed to contribute to the immune suppressed state of the TME.

The inhibition of IDO was one of the first small molecule drug strategies proposed for re-establishment of an immunogenic response to cancer (Mellor and Munn 2004). The d-enantiomer of 1-methyl tryptophan (D-1 MTor indoximod) was the first IDO inhibitor to enter clinical trials. While this compound clearly does inhibit the activity of IDO, it is a very weak inhibitor of the isolated enzyme and the in vivo mechanism(s) of action for this compound are still being elucidated. Investigators at Incyte optimized a hit compound obtained from a screening process into a potent and selective inhibitor with sufficient oral exposure to demonstrate a delay in tumor growth in a mouse melanoma model (Yue, Douty et al. 2009). Further development of this series led to INCB204360 which is a highly selective for inhibition of IDO-1 over IDO-2 and TDO in cell lines transiently transfected with either human or mouse enzymes (Liu, Shin et al. 2010). Similar potency was seen for cell lines and primary human tumors which endogenously express IDO1 (IC50s~3-20 nM). When tested in co-culture of DCs and naïve CD4+CD25− T cells, INCB204360 blocked the conversion of these T cells into CD4+FoxP3+ Tregs. Finally, when tested in a syngeneic model (PAN02 pancreatic cells) in immunocompetent mice, orally dosed INCB204360 provided a significant dose-dependent inhibition of tumor growth, but was without effect against the same tumor implanted in immune-deficient mice. Additional studies by the same investigators have shown a correlation of the inhibition of IDO1 with the suppression of systemic kynurenine levels and inhibition of tumor growth in an additional syngeneic tumor model in immunocompetent mice. Based upon these preclinical studies, INCB24360 entered clinical trials for the treatment of metastatic melanoma (Beatty, O'Dwyer et al. 2013).

In light of the importance of the catabolism of tryptophan in the maintenance of immune suppression, it is not surprising that overexpression of a second tryptophan metabolizing enzyme, TDO2, by multiple solid tumors (for example, bladder and liver carcinomas, melanomas) has also been detected. A survey of 104 human cell lines revealed 20/104 with TDO expression, 17/104 with IDO1 and 16/104 expressing both (Pilotte, Larrieu et al. 2012). Similar to the inhibition of IDO1, the selective inhibition of TDO2 is effective in reversing immune resistance in tumors overexpressing TDO2 (Pilotte, Larrieu et al. 2012). These results support TDO2 inhibition and/or dual TDO2/IDO1 inhibition as a viable therapeutic strategy to improve immune function.

Multiple pre-clinical studies have demonstrated significant, even synergistic, value in combining IDO-1 inhibitors in combination with T cell checkpoint modulating mAbs to CTLA-4, PD-1, and GITR. In each case, both efficacy and related PD aspects of improved immune activity/function were observed in these studies across a variety of murine models (Balachandran, Cavnar et al. 2011, Holmgaard, Zamarin et al. 2013, M. Mautino 2014, Wainwright, Chang et al. 2014). The Incyte IDO1 inhibitor (INCB204360, epacadostat) has been clinically tested in combination with a CTLA4 blocker (ipilimumab), but it is unclear that an effective dose was achieved due to dose-limited adverse events seen with the combination. In contrast recently released data for an on-going trial combining epacadostat with Merck's PD-1 mAb (pembrolizumab) demonstrated improved tolerability of the combination allowing for higher doses of the IDO1 inhibitor. There have been several clinical responses across various tumor types which is encouraging. However, it is not yet known if this combination is an improvement over the single agent activity of pembrolizumab (Gangadhar, Hamid et al. 2015). Similarly, Roche/Genentech are advancing NGL919/GDC-0919 in combination with both mAbs for PD-L1 (MPDL3280A, Atezo) and OX-40 following the recent completion of a phase 1a safety and PK/PD study in patients with advanced tumors.

IDO1 and Chronic Infections

IDO1 activity generates kynurenine pathway metabolites such as Kyn and 3-HAA that impair at least T cell, NK cell, and macrophage activity (Munn, Shafizadeh et al. 1999, Frumento, Rotondo et al. 2002) (Sekkai, Guittet et al. 1997, Favre, Mold et al. 2010). Kyn levels or the Kyn/Tryp ratio are elevated in the setting of chronic HIV infection (Byakwaga, Boum et al. 2014, Hunt, Sinclair et al. 2014, Tenorio, Zheng et al. 2014), HBV infection (Chen, Li et al. 2009), HCV infection (Larrea, Riezu-Boj et al. 2007, Asghar, Ashiq et al. 2015), and TB infection (Suzuki, Suda et al. 2012) and are associated with antigen-specific T cell dysfunction (Boasso, Herbeuval et al. 2007, Boasso, Hardy et al. 2008, Loughman and Hunstad 2012, Ito, Ando et al. 2014, Lepiller, Soulier et al. 2015). As such, it is thought that in these cases of chronic infection, IDO1-mediated inhibition of the pathogen-specific T cell response plays a role in the persistence of infection, and that inhibition of IDO1 may have a benefit in promoting clearance and resolution of infection.

IDO1 and Sepsis

IDO1 expression and activity are observed to be elevated during sepsis and the degree of Kyn or Kyn/Tryp elevation corresponded to increased disease severity, including mortality (Tattevin, Monnier et al. 2010, Darcy, Davis et al. 2011). In animal models, blockade of IDO1 or IDO1 genetic knockouts protected mice from lethal doses of LPS or from mortality in the cecal ligation/puncture model (Jung, Lee et al. 2009, Hoshi, Osawa et al. 2014). Sepsis is characterized by an immunosuppressive phase in severe cases (Hotchkiss, Monneret et al. 2013), potentially indicating a role for IDO1 as a mediator of immune dysfunction, and indicating that pharmacologic inhibition of IDO1 may provide a clinical benefit in sepsis.

IDO1 and Neurological Disorders

In addition to immunologic settings, IDO1 activity is also linked to disease in neurological settings (reviewed in Lovelace Neuropharmacology 2016 (Lovelace, Varney et al. 2016)). Kynurenine pathway metabolites such as 3-hydroxykynurenine and quinolinic acid are neurotoxic, but are balanced by alternative metabolites kynurenic acid or picolinic acid, which are neuroprotective. Neurodegenerative and psychiatric disorders in which kynurenine pathway metabolites have been demonstrated to be associated with disease include multiple sclerosis, motor neuron disorders such as amyotrophic lateral sclerosis, Huntington's disease, Parkinson's disease, Alzheimer's disease, major depressive disorder, schizophrenia, anorexia (Lovelace, Varney et al. 2016). Animal models of neurological disease have shown some impact of weak IDO1 inhibitors such as 1-methyltryptophan on disease, indicating that IDO1 inhibition may provide clinical benefit in prevention or treatment of neurological and psychiatric disorders.

It would therefore be an advance in the art to discover IDO inhibitors that effective the balance of the aforementioned properties as a disease modifying therapy in chronic HIV infections to decrease the incidence of non-AIDS morbidity/mortality; and/or a disease modifying therapy to prevent mortality in sepsis; and/or an immunotherapy to enhance the immune response to HIV, HBV, HCV and other chronic viral infections, chronic bacterial infections, chronic fungal infections, and to tumors; and/or for the treatment of depression or other neurological/neuropsychiatric disorders.

Asghar, K., M. T. Ashiq, B. Zulfiqar, A. Mahroo, K. Nasir and S. Murad (2015). "Indoleamine 2,3-dioxygenase expression and activity in patients with hepatitis C virus-induced liver cirrhosis." *Exp Ther Med* 9(3): 901-904.

Balachandran, V. P., M. J. Cavnar, S. Zeng, Z. M. Bamboat, L. M. Ocuin, H. Obaid, E. C. Sorenson, R. Popow, C. Ariyan, F. Rossi, P. Besmer, T. Guo, C. R. Antonescu, T. Taguchi, J. Yuan, J. D. Wolchok, J. P. Allison and R. P. Dematteo (2011). "Imatinib potentiates antitumor T cell responses in gastrointestinal stromal tumor through the inhibition of Ido." *Nature Medicine* 17(9): 1094-1100.

Beatty, G. L., P. J. O'Dwyer, J. Clark, J. G. Shi, R. C. Newton, R. Schaub, J. Maleski, L. Leopold and T. Gajewski (2013). "Phase I study of the safety, pharmacokinetics (PK), and pharmacodynamics (PD) of the oral inhibitor of indoleamine 2,3-dioxygenase (IDO1) INCB024360 in patients (pts) with advanced malignancies." *ASCO Meeting Abstracts* 31(15_suppl): 3025.

Boasso, A., A. W. Hardy, S. A. Anderson, M. J. Dolan and G. M. Shearer (2008). "HIV-induced type I interferon and tryptophan catabolism drive T cell dysfunction despite phenotypic activation." *PLoS One* 3(8): e2961.

Boasso, A., J. P. Herbeuval, A. W. Hardy, S. A. Anderson, M. J. Dolan, D. Fuchs and G. M. Shearer (2007). "HIV inhibits CD4+ T-cell proliferation by inducing indoleamine 2,3-dioxygenase in plasmacytoid dendritic cells." *Blood* 109(8): 3351-3359.

Boasso, A. and G. M. Shearer (2008). "Chronic innate immune activation as a cause of HIV-1 immunopathogenesis." *Clin Immunol* 126(3): 235-242.

Boasso, A., M. Vaccari, A. Hryniewicz, D. Fuchs, J. Nacsa, V. Cecchinato, J. Andersson, G. Franchini, G. M. Shearer and C. Chougnet (2007). "Regulatory T-cell markers, indoleamine 2,3-dioxygenase, and virus levels in spleen and gut during progressive simian immunodeficiency virus infection." *J Virol* 81(21): 11593-11603.

Byakwaga, H., Y. Boum, 2nd, Y. Huang, C. Muzoora, A. Kembabazi, S. D. Weiser, J. Bennett, H. Cao, J. E. Haberer, S. G. Deeks, D. R. Bangsberg, J. M. McCune, J. N. Martin and P. W. Hunt (2014). "The kynurenine pathway of tryptophan catabolism, CD4+ T-cell recovery, and mortality among HIV-infected Ugandans initiating antiretroviral therapy." *J Infect Dis* 210(3): 383-391.

Chen, Y. B., S. D. Li, Y. P. He, X. J. Shi, Y. Chen and J. P. Gong (2009). "Immunosuppressive effect of IDO on T cells in patients with chronic hepatitis B*." *Hepatol Res* 39(5): 463-468.

Darcy, C. J., J. S. Davis, T. Woodberry, Y. R. McNeil, D. P. Stephens, T. W. Yeo and N. M. Anstey (2011). "An observational cohort study of the kynurenine to tryptophan ratio in sepsis: association with impaired immune and microvascular function." *PLoS One* 6(6): e21185.

Deeks, S. G. (2011). "HIV infection, inflammation, immunosenescence, and aging." *Annu Rev Med* 62: 141-155.

Favre, D., S. Lederer, B. Kanwar, Z. M. Ma, S. Proll, Z. Kasakow, J. Mold, L. Swainson, J. D. Barbour, C. R. Baskin, R. Palermo, I. Pandrea, C. J. Miller, M. G. Katze and J. M. McCune (2009). "Critical loss of the balance between Th17 and T regulatory cell populations in pathogenic SIV infection." *PLoS Pathog* 5(2): e1000295.

Favre, D., J. Mold, P. W. Hunt, B. Kanwar, P. Loke, L. Seu, J. D. Barbour, M. M. Lowe, A. Jayawardene, F. Aweeka, Y. Huang, D. C. Douek, J. M. Brenchley, J. N. Martin, F. M. Hecht, S. G. Deeks and J. M. McCune (2010). "Tryptophan catabolism by indoleamine 2,3-dioxygenase 1 alters the balance of TH17 to regulatory T cells in HIV disease." *Sci Transl Med* 2(32): 32ra36.

Frumento, G., R. Rotondo, M. Tonetti, G. Damonte, U. Benatti and G. B. Ferrara (2002). "Tryptophan-derived catabolites are responsible for inhibition of T and natural killer cell proliferation induced by indoleamine 2,3-dioxygenase." *J Exp Med* 196(4): 459-468.

Gangadhar, T., O. Hamid, D. Smith, T. Bauer, J. Wasser, J. Luke, A. Balmanoukian, D. Kaufman, Y. Zhao, J. Maleski, L. Leopold and T. Gajewski (2015). "Preliminary results from a Phase I/I study of epacadostat (incb024360) in combination with pembrolizumab in patients with selected advanced cancers." *Journal for ImmunoTherapy of Cancer* 3(Suppl 2): O7.

Holmgaard, R. B., D. Zamarin, Y. Li, B. Gasmi, D. H. Munn, J. P. Allison, T. Merghoub and J. D. Wolchok (2015). "Tumor-Expressed IDO Recruits and Activates MDSCs in a Treg-Dependent Manner." *Cell Reports* 13(2): 412-424.

Holmgaard, R. B., D. Zamarin, D. H. Munn, J. D. Wolchok and J. P. Allison (2013). "Indoleamine 2,3-dioxygenase is a critical resistance mechanism in antitumor T cell immunotherapy targeting CTLA-4." *Journal of Experimental Medicine* 210(7): 1389-1402.

Hoshi, M., Y. Osawa, H. Ito, H. Ohtaki, T. Ando, M. Takamatsu, A. Hara, K. Saito and M. Seishima (2014). "Blockade of indoleamine 2,3-dioxygenase reduces mortality from peritonitis and sepsis in mice by regulating functions of CD11b+ peritoneal cells." *Infect Immun* 82(11): 4487-4495.

Hotchkiss, R. S., G. Monneret and D. Payen (2013). "Sepsis-induced immunosuppression: from cellular dysfunctions to immunotherapy." *Nat Rev Immunol* 13(12): 862-874.

Hunt, P. W., E. Sinclair, B. Rodriguez, C. Shive, B. Clagett, N. Funderburg, J. Robinson, Y. Huang, L. Epling, J. N. Martin, S. G. Deeks, C. L. Meinert, M. L. Van Natta, D. A. Jabs and M. M. Lederman (2014). "Gut epithelial barrier dysfunction and innate immune activation predict mortality in treated HIV infection." *J Infect Dis* 210(8): 1228-1238.

Ito, H., T. Ando, K. Ando, T. Ishikawa, K. Saito, H. Moriwaki and M. Seishima (2014). "Induction of hepatitis B virus surface antigen-specific cytotoxic T lymphocytes can be up-regulated by the inhibition of indoleamine 2, 3-dioxygenase activity." *Immunology* 142(4): 614-623.

Jung, I. D., M. G. Lee, J. H. Chang, J. S. Lee, Y. I. Jeong, C. M. Lee, W. S. Park, J. Han, S. K. Seo, S. Y. Lee and Y. M. Park (2009). "Blockade of indoleamine 2,3-dioxygenase protects mice against lipopolysaccharide-induced endotoxin shock." *J Immunol* 182(5): 3146-3154.

Larrea, E., J. I. Riezu-Boj, L. Gil-Guerrero, N. Casares, R. Aldabe, P. Sarobe, M. P. Civeira, J. L. Heeney, C. Rollier, B. Verstrepen, T. Wakita, F. Borras-Cuesta, J. J. Lasarte and J. Prieto (2007). "Upregulation of indoleamine 2,3-dioxygenase in hepatitis C virus infection." *J Virol* 81(7): 3662-3666.

Lepiller, Q., E. Soulier, Q. Li, M. Lambotin, J. Barths, D. Fuchs, F. Stoll-Keller, T. J. Liang and H. Barth (2015). "Antiviral and Immunoregulatory Effects of Indoleamine-2,3-Dioxygenase in Hepatitis C Virus Infection." *J Innate Immun* 7(5): 530-544.

Li, L., L. Huang, H. P. Lemos, M. Mautino and A. L. Mellor (2012). "Altered tryptophan metabolism as a paradigm for good and bad aspects of immune privilege in chronic inflammatory diseases." *Front Immunol* 3: 109.

Liu, X., N. Shin, H. K. Koblish, G. Yang, Q. Wang, K. Wang, L. Leffet, M. J. Hansbury, B. Thomas, M. Rupar, P. Waeltz, K. J. Bowman, P. Polam, R. B. Sparks, E. W. Yue, Y. Li, R. Wynn, J. S. Fridman, T. C. Burn, A. P. Combs, R. C. Newton and P. A. Scherle (2010). "Selective inhibition of IDO1 effectively regulates mediators of antitumor immunity." *Blood* 115(17): 3520-3530.

Loughman, J. A. and D. A. Hunstad (2012). "Induction of indoleamine 2,3-dioxygenase by uropathogenic bacteria attenuates innate responses to epithelial infection." *J Infect Dis* 205(12): 1830-1839.

Lovelace, M. D., B. Varney, G. Sundaram, M. J. Lennon, C. K. Lim, K. Jacobs, G. J. Guillemin and B. J. Brew (2016). "Recent evidence for an expanded role of the kynurenine pathway of tryptophan metabolism in neurological diseases." *Neuropharmacology*.

M. Mautino, C. J. L., N. Vahanian, J. Adams, C. Van Allen, M. D. Sharma, T. S. Johnson and D. H. Munn (2014). "Synergistic antitumor effects of combinatorial immune checkpoint inhibition with anti-PD-1/PD-L antibodies and the IDO pathway inhibitors NLG919 and indoximod in the context of active immunotherapy." April 2014 *AACR Meeting* Poster #5023.

Mattapallil, J. J., D. C. Douek, B. Hill, Y. Nishimura, M. Martin and M. Roederer (2005). "Massive infection and loss of memory CD4+ T cells in multiple tissues during acute SIV infection." *Nature* 434(7037): 1093-1097.

Mellor, A. L. and D. H. Munn (2004). "IDO expression by dendritic cells: Tolerance and tryptophan catabolism." *Nature Reviews Immunology* 4(10): 762-774.

Munn, D. H. (2011). "Indoleamine 2,3-dioxygenase, Tregs and cancer." *Current Medicinal Chemistry* 18(15): 2240-2246.

Munn, D. H., E. Shafizadeh, J. T. Attwood, I. Bondarev, A. Pashine and A. L. Mellor (1999). "Inhibition of T cell proliferation by macrophage tryptophan catabolism." *J Exp Med* 189(9): 1363-1372.

Pilotte, L., P. Larrieu, V. Stroobant, D. Colau, E. Dolušić, R. Frédérick, E. De Plaen, C. Uyttenhove, J. Wouters, B. Masereel and B. J. Van Den Eynde (2012). "Reversal of tumoral immune resistance by inhibition of tryptophan 2,3-dioxygenase." *Proceedings of the National Academy of Sciences of the United States of America* 109(7): 2497-2502.

Sekkai, D., O. Guittet, G. Lemaire, J. P. Tenu and M. Lepoivre (1997). "Inhibition of nitric oxide synthase expression and activity in macrophages by 3-hydroxyanthranilic acid, a tryptophan metabolite." *Arch Biochem Biophys* 340(1): 117-123.

Suzuki, Y., T. Suda, K. Asada, S. Miwa, M. Suzuki, M. Fujie, K. Furuhashi, Y. Nakamura, N. Inui, T. Shirai, H. Hayakawa, H. Nakamura and K. Chida (2012). "Serum indoleamine 2,3-dioxygenase activity predicts prognosis of pulmonary tuberculosis." *Clin Vaccine Immunol* 19(3): 436-442.

Tattevin, P., D. Monnier, O. Tribut, J. Dulong, N. Bescher, F. Mourcin, F. Uhel, Y. Le Tulzo and K. Tarte (2010). "Enhanced indoleamine 2,3-dioxygenase activity in patients with severe sepsis and septic shock." *J Infect Dis* 201(6): 956-966.

Tenorio, A. R., Y. Zheng, R. J. Bosch, S. Krishnan, B. Rodriguez, P. W. Hunt, J. Plants, A. Seth, C. C. Wilson, S. G. Deeks, M. M. Lederman and A. L. Landay (2014). "Soluble markers of inflammation and coagulation but not T-cell activation predict non-AIDS-defining morbid events during suppressive antiretroviral treatment." *J Infect Dis* 210(8): 1248-1259.

Wainwright, D. A., I. V. Balyasnikova, A. L. Chang, A. U. Ahmed, K.-S. Moon, B. Auffinger, A. L. Tobias, Y. Han and M. S. Lesniak (2012). "IDO Expression in Brain Tumors Increases the Recruitment of Regulatory T Cells and Negatively Impacts Survival." *Clinical Cancer Research* 18(22): 6110-6121.

Wainwright, D. A., A. L. Chang, M. Dey, I. V. Balyasnikova, C. K. Kim, A. Tobias, Y. Cheng, J. W. Kim, J. Qiao, L. Zhang, Y. Han and M. S. Lesniak (2014). "Durable therapeutic efficacy utilizing combinatorial blockade against IDO, CTLA-4, and PD-L1 in mice with brain tumors." *Clinical Cancer Research* 20(20): 5290-5301.

Yue, E. W., B. Douty, B. Wayland, M. Bower, X. Liu, L. Leffet, Q. Wang, K. J. Bowman, M. J. Hansbury, C. Liu, M. Wei, Y. Li, R. Wynn, T. C. Burn, H. K. Koblish, J. S. Fridman, B. Metcalf, P. A. Scherle and A. P. Combs (2009). "Discovery of potent competitive inhibitors of indoleamine 2,3-dioxygenase with in vivo pharmacodynamic activity and efficacy in a mouse melanoma model." *Journal of Medicinal Chemistry* 52(23): 7364-7367.

SUMMARY OF THE INVENTION

Briefly, in one aspect, the present invention discloses compounds of Formula I

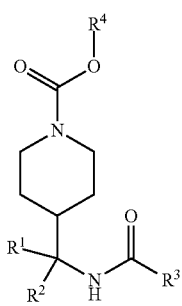

Formula I or a pharmaceutically acceptable salt thereof wherein:

$R^1$ and $R^2$ are independently H, $C_{1-6}$alkyl, $C_{3-6}$cycloalkyl, $C_{1-3}$alkyl-O—$C_{1-4}$alkylene-, HO—$C_{1-4}$alkylene, $C_{5-9}$aryl, 5-9 membered heteroaryl, or $R^1$ and $R^2$ together with the carbon to which they are bonded form a 3-6 membered cycloalkyl; and wherein $R^1$ and $R^2$ may optionally be substituted with 1 or 2 substituents selected from H, $C_{1-4}$alkyl, halogen, —O$C_{1-4}$alkyl, —COOH, NH—$C_{1-4}$alkyl, —NH$_2$, and OH;

$R^3$ is $CO_5$-aryl or 5 to 9 membered heteroaryl; and wherein $R^3$ and $R^4$ may optionally be substituted with 1-3 substituents independently selected from halogen, $C_{1-3}$alkyl, $C_{1-3}$haloalkyl, —O$C_{1-3}$alkyl, $C_{2-4}$alkenyl, $C_{2-4}$alkynyl CN, and —C(O)NH$_2$;

and wherein each aryl and each heteroaryl includes bicycles and each heteroaryl contains from 1 to 3 heteroatoms selected from O, N, and S;

$R^4$ is $C_{5-9}$-aryl or a 5 to 9 membered heteroaryl, wherein said aryl or heteroaryl may be linked to the rest of the compound with a $CH_2$; and wherein $R^3$ may optionally be substituted with 1-3 substituents independently selected from halogen, $C_{1-3}$alkyl, $C_{1-3}$haloalkyl, —O$C_{1-3}$alkyl, CN, and —C(O)NH$_2$;

and wherein each aryl and each heteroaryl includes bicycles and each heteroaryl contains from 1 to 3 heteroatoms selected from O, N, and S.

In another aspect, the present invention discloses a method for treating diseases or conditions that would benefit from inhibition of IDO.

In another aspect, the present invention discloses pharmaceutical compositions comprising a compound of Formula I or a pharmaceutically acceptable salt thereof.

In another aspect, the present invention provides a compound of Formula I or a pharmaceutically acceptable salt thereof for use in therapy.

In another aspect, the present invention provides a compound of Formula I or a pharmaceutically acceptable salt thereof for use in treating diseases or condition that would benefit from inhibition of IDO.

In another aspect, the present invention provides use of a compound of Formula I or a pharmaceutically acceptable salt thereof in the manufacture of a medicament for use in treating diseases or conditions that would benefit from inhibition of IDO.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

DETAILED DESCRIPTION OF REPRESENTATIVE EMBODIMENTS

Preferably one of $R^1$ and $R^2$ is H and the other is $C_{1-6}$alkyl, $C_{3-6}$cycloalkyl, $C_{1-3}$alkyl-O—$C_{1-4}$alkylene-, HO—$C_{1-4}$alkylene, phenyl, or pyridyl. When one of $R^1$ and $R^2$ is H, the preferred stereochemistry of the carbon to which they are bonded is as shown below. For illustrative purposes, $R^1$ has been designated as H.

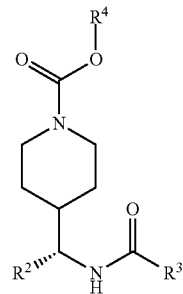

Preferably $R^3$ is thiophene, phenyl, indole, indazole, or thiadiazole; optionally substituted with one or two substituents independently selected from, halogen, $C_{1-3}$alkyl, $C_{1-3}$fluoroalkyl, —O$C_{1-3}$alkyl, $C_{2-4}$alkynyl, $C_{2-4}$alkenyl, CN, and —C(O)NH$_2$. More preferably $R^3$ is thiophene or phenyl optionally substituted with one or two substituents independently selected from, halogen and $CH_3$.

Preferably $R^4$ is phenyl, pyridyl, pyrimidine, quinoline, tetrahydroquinoline, indazole, or thiazole; optionally substituted with one or two substituents independently selected from, halogen, $C_{1-3}$alkyl, $C_{1-3}$fluoroalkyl, —O$C_{1-3}$alkyl, and CN. More preferably $R^4$ is phenyl, pyridyl, or pyrimidine optionally substituted with one or two substituents independently selected from, halogen, $CH_3$, $CF_3$, —O$CH_3$, and CN.

Preferred pharmaceutical compositions include unit dosage forms. Preferred unit dosage forms include tablets.

In particular, it is expected that the compounds and composition of this invention will be useful for prevention and/or treatment of HIV; including the prevention of the progression of AIDS and general immunosuppression. It is expected that in many cases such prevention and/or treatment will involve treating with the compounds of this invention in combination with at least one other drug thought to be useful for such prevention and/or treatment. For example, the IDO inhibitors of this invention may be used in combination with other immune therapies such as immune checkpoints (PD1, CTLA4, ICOS, etc.) and possibly in combination with growth factors or cytokine therapies (IL21, IL-7, etc.).

In is common practice in treatment of HIV to employ more than one effective agent. Therefore, in accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors. Examples of such additional agents are Dolutegravir, Bictegravir, and Cabotegravir.

It is also common practice in the oncology field to treat with more than one effective agent. Therefore, in accordance with another embodiment of the present invention, there is provided a method for preventing or treating cancer comprising administering to a human in need thereof a therapeutically effective amount of a compound of Formula I or a pharmaceutically acceptable salt thereof further comprising administration of at least one other agent effective for preventing or treating cancer. Such agents include, for example, anti-neoplastic agents, chemotherapeutic agents, hormonal agents, and antibody agents.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

In one embodiment, the pharmaceutical formulation containing a compound of Formula I or a salt thereof is a formulation adapted for oral or parenteral administration. In another embodiment, the formulation is a long-acting parenteral formulation. In a further embodiment, the formulation is a nano-particle formulation.

The present invention is directed to compounds, compositions and pharmaceutical compositions that have utility as novel treatments for immunosuppresion. While not wanting to be bound by any particular theory, it is thought that the present compounds are able to inhibit the enzyme that catalyzes the oxidative pyrrole ring cleavage reaction of I-Trp to N-formylkynurenine utilizing molecular oxygen or reactive oxygen species.

Therefore, in another embodiment of the present invention, there is provided a method for the prevention and/or treatment of HIV; including the prevention of the progression of AIDS and general immunosuppression.

EXAMPLES

The following examples serve to more fully describe the manner of making and using the above-described invention. It is understood that these examples in no way serve to limit the true scope of the invention, but rather are presented for illustrative purposes. In the examples and the synthetic schemes below, the following abbreviations have the following meanings. If an abbreviation is not defined, it has its generally accepted meaning.

CAN=acetonitrile
AIBN=azobisisobutyronitrile
aq.=aqueous
μL or uL=microliters
μM or uM=micromolar
NMR=nuclear magnetic resonance
Boc=tert-butoxycarbonyl
Br=broad
Cbz=Benzyloxycarbonyl
CDI=1,1'-carbonyldiimidazole
D=doublet
Δ=chemical shift
° C.=degrees celcius
DCM=dichloromethane
Dd=doublet of doublets
DHP=dihydropyran
DIAD=diisopropyl azodicarboxylate
DIEA or DIPEA=N,N-diisopropylethylamine
DMAP=4-(dimethylamino)pyridine
DMEM=Dulbeco's Modified Eagle's Medium
EtOAc=ethyl acetate
h or hr=hours
HATU=1-[Bis(dimethylamino)methylene]-1H-1,2,3-triazolo[4,5-b]pyridinium 3-oxid hexafluorophosphate
HCV=hepatitis C virus
HPLC=high performance liquid chromatography
Hz=hertz
IU=International Units
$IC_{50}$=inhibitory concentration at 50% inhibition
J=coupling constant (given in Hz unless otherwise indicated)

LCMS=liquid chromatography-mass spectrometry
M=multiplet
M=molar
M+H⁺=parent mass spectrum peak plus H⁺
MeOH=methanol
Mg=milligram
Min=minutes
mL=milliliter
mM=millimolar
Mmol=millimole
MS=mass spectrum
MTBE=methyl tert-butyl ether
N=normal
NFK=N-formylkynurenine
NBS=N-bromosuccinimide
Nm=nanomolar
PE=petroleum ether
Ppm=parts per million
q.s.=sufficient amount
S=singlet
RT=room temperature
Rf=retardation factor
sat.=saturated
T=triplet
TEA=triethylamine
TFA=trifluoroacetic acid
TFAA=trifluoroacetic anhydride
THF=tetrahydrofuran Equipment Description $^1$H NMR spectra were recorded on a Bruker Ascend 400 spectrometer or a Varian 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters ACQUITY UPLC with SQ Detectors using a Waters BEH C18, 2.1×50 mm, 1.7 μm using a gradient elution method.

Solvent A: 0.1% formic acid (FA) in water;
Solvent B: 0.1% FA in acetonitrile;
30% B for 0.5 min followed by 30-100% B over 2.5 min.

Example 37

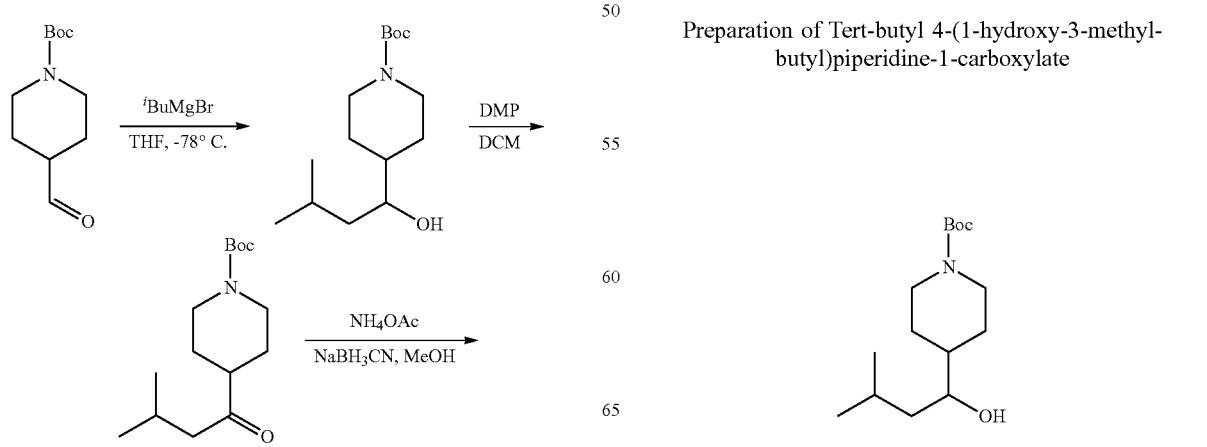

Preparation of Tert-butyl 4-(1-hydroxy-3-methyl-butyl)piperidine-1-carboxylate

At −78° C., to a solution of tert-butyl 4-formylpiperidine-1-carboxylate (2.5 g, 11.72 mmol) in THF (25 mL), was slowly added a solution of isobutylmagnesium bromide in ether (35.2 mL, 35.16 mmol). After stirred at r.t. overnight, the reaction was quenched with saturated NH₄Cl aq. solution and extracted with EtOAc. The organic layer was washed with brine, dried over Na₂SO₄, filtered and concentrated to give the crude product which was purified by flash chromatography (silica gel, 0-50% EtOAc in PE) to afford the title compound (2.24 g, 70% yield). LCMS (ESI) m/z calcd for $C_{15}H_{29}NO_3$: 271.21. Found: 272.63 (M+1)⁺.

Preparation of Tert-butyl 4-(3-methylbutanoyl)piperidine-1-carboxylate

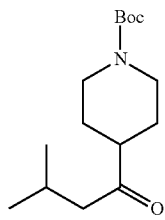 [SMILES: CC(C)CC(=O)C1CCN(C(=O)OC(C)(C)C)CC1]

To a solution of tert-butyl 4-(1-hydroxy-3-methylbutyl)piperidine-1-carboxylate (2.24 g, 8.25 mmol) in DCM (25 mL), was added DMP (6.99 g, 16.5 mmol) in portion wise. After stirred at r.t. for 2 h, the reaction was quenched with saturated NH₄Cl aq. solution and extracted with EtOAc. The organic layer was washed with brine, dried over Na₂SO₄, filtered and concentrated to give the crude product which was purified by flash chromatography (silica gel, 0-30% EtOAc in PE) to afford the title compound (1.55 g, 70% yield). LCMS (ESI) m/z calcd for $C_{15}H_{27}NO_3$: 269.20. Found: 270.44 (M+1)⁺.

Preparation of Tert-butyl 4-(1-amino-3-methylbutyl)piperidine-1-carboxylate

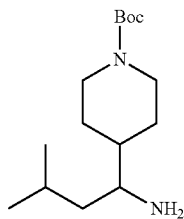

To a solution of tert-butyl 4-(3-methylbutanoyl)piperidine-1-carboxylate (1.55 g, 5.75 mmol) in MeOH (20 mL), was added NH₄OAc (8.86 g, 115 mmol) and NaBH₃CN (3.61 g, 57.5 mmol) successively. After stirred at r.t. overnight, the reaction was quenched with saturated NH₄Cl aq. solution and extracted with EtOAc. The organic layer was washed with brine, dried over Na₂SO₄, filtered and concentrated to afford the title compound (1.59 g, 100% yield), which was used in the following step without further purification. LCMS (ESI) m/z calcd for $C_{15}H_{30}N_2O_2$: 270.23. Found: 271.67 (M+1)⁺.

Preparation of Tert-butyl 4-(1-(4-fluorobenzamido)-3-methylbutyl)piperidine-1-carboxylate

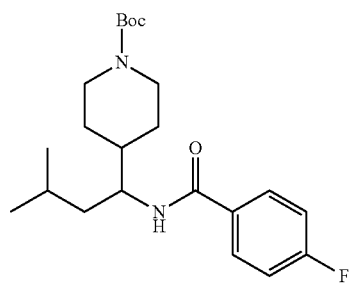

To a solution of tert-butyl 4-(1-amino-3-methylbutyl)piperidine-1-carboxylate (1.59 g, 5.89 mmol) in DMF (20 mL), was added 4-fluorobenzoic acid (825 mg, 5.89 mmol), DIPEA (3 mL, 17.68 mmol) and HATU (3.36 g, 8.84 mmol) successively. After stirred at r.t. for 3 h, the reaction was diluted with water and extracted with EtOAc. The organic layer was washed with brine, dried over Na₂SO₄, filtered and concentrated to give the crude product which was purified by flash chromatography (silica gel, 0-50% EtOAc in PE) to afford the title compound (1.9 g, 82% yield). LCMS (ESI) m/z calcd for $C_{22}H_{33}FN_2O_3$: 392.25. Found: 393.74 (M+1)⁺.

Preparation of 4-fluoro-N-(3-methyl-1-(piperidin-4-yl)butyl)benzamide

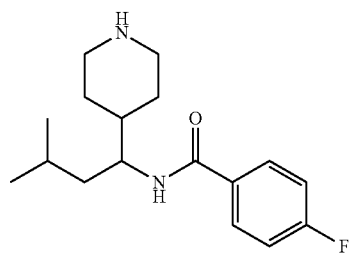

To a solution of tert-butyl 4-(1-(4-fluorobenzamido)-3-methylbutyl)piperidine-1-carboxylate (1.49 g, 3.8 mmol) in DCM (15 mL), was added 4 M HCl in dioxane (5 mL) dropwise. After stirred at r.t. for 2 h, the reaction mixture was concentrated to to afford the title compound (1.54 g, 100% yield), which was used in the following step without purification. LCMS (ESI) m/z calcd for $C_{17}H_{25}FN_2O$: 292.20. Found: 293.39 (M+1)⁺.

Preparation of Phenyl 4-(1-(4-fluorobenzamido)-3-methylbutyl)piperidine-1-carboxylate

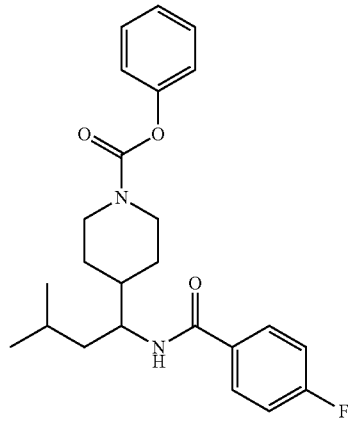

At 0° C., to a solution of 4-fluoro-N-(3-methyl-1-(piperidin-4-yl)butyl)benzamide (60 mg, 0.182 mmol) and DIPEA (94 mg, 0.728 mmol) in DCM (2 mL), was added phenyl carbonochloridate (43 mg, 0.273 mmol) drop wise. After stirred at r.t. for 2 h, the reaction was quenched with saturated NaHCO$_3$ aq. solution and extracted with EtOAc. The organic layer was washed with aq. NaHCO$_3$, brine and dried over Na$_2$SO$_4$. Solvent was removed under vacuum and the residue was purified by Gilson (C18, 10-50% MeCN in water with 0.1% formic acid) to afford the title compound (40 mg, 69%) as a white solid. $^1$H NMR (400 MHz, DMSO) δ 8.09 (d, J=9.2 Hz, 1H), 7.96-7.89 (m, 2H), 7.36 (t, J=7.9 Hz, 2H), 7.32-7.25 (m, 2H), 7.20 (t, J=7.4 Hz, 1H), 7.09 (d, J=7.6 Hz, 2H), 4.20-4.13 (m, 1H), 4.06-3.96 (m, 2H), 2.95 (d, J=11.8 Hz, 1H), 2.83-2.75 (m, 1H), 1.79-1.56 (m, 5H), 1.34-1.21 (m, 3H), 0.95-0.78 (m, 6H). LCMS (ESI) m/z calcd for C$_{24}$H$_{29}$FN$_2$O$_3$: 412.22. Found: 413.35 (M+1)$^+$.

Example 40

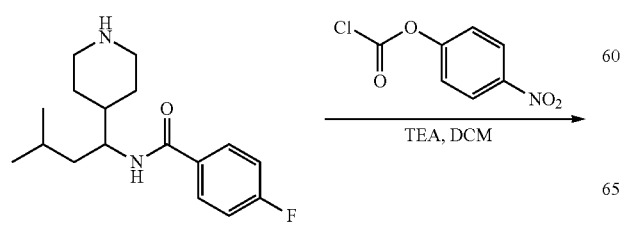

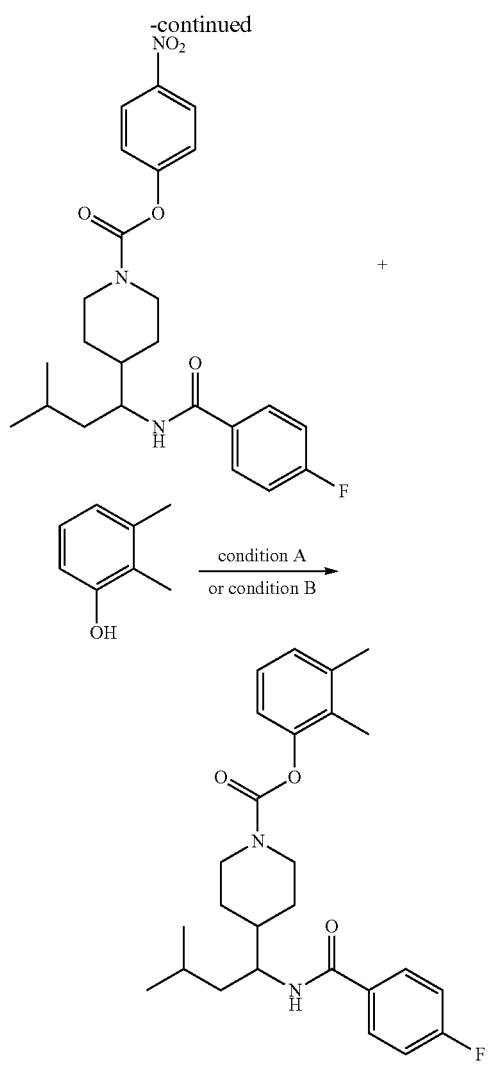

Preparation of 4-nitrophenyl 4-(1-(4-fluorobenzamido)-3-methylbutyl)piperidine-1-carboxylate

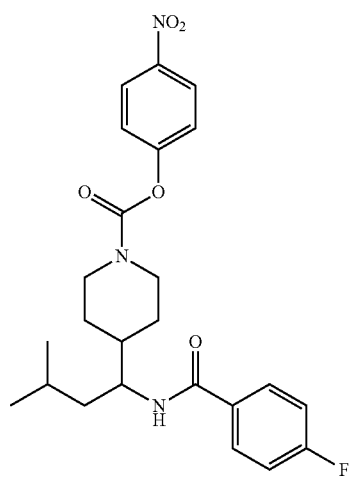 [SMILES: CC(C)CC(NC(=O)c1ccc(F)cc1)C1CCN(C(=O)Oc2ccc([N+](=O)[O-])cc2)CC1]

At 0° C., to a solution of 4-fluoro-N-(3-methyl-1-(piperidin-4-yl)butyl)benzamide (500 mg, 1.52 mmol) and TEA (1.1 mL, 7.62 mmol) in DCM (10 mL), was added 4-nitrophenyl carbonochloridate (338 mg, 1.68 mmol) drop wise. After stirred at r.t. for 2 h, the reaction was quenched with saturated NaHCO$_3$ aq. solution and extracted with EtOAc. The organic layer was washed with brine, dried over Na$_2$SO$_4$, filtered and concentrated to give the crude product which was purified by flash chromatography (silica gel, 0-30% EtOAc in PE) to afford the title compound (510 mg, 73% yield). LCMS (ESI) m/z calcd for C$_{24}$H$_{28}$FN$_3$O$_5$: 457.20. Found: 458.79 (M+1)$^+$.

Preparation of 2,3-dimethylphenyl 4-(1-(4-fluorobenzamido)-3-methylbutyl) Piperidine-1-carboxylate

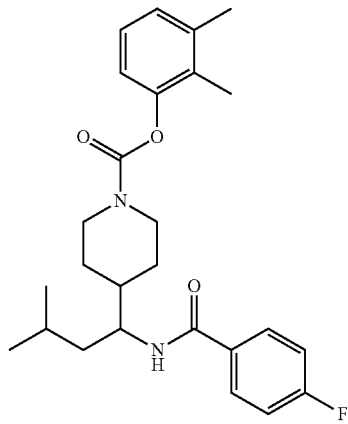 [SMILES: Cc1cccc(OC(=O)N2CCC(C(CC(C)C)NC(=O)c3ccc(F)cc3)CC2)c1C]

Condition A: A mixture of 4-nitrophenyl 4-(1-(4-fluorobenzamido)-3-methylbutyl) piperidine-1-carboxylate (120 mg, 0.262 mmol), 2,3-dimethylphenol (320 mg, 2.625 mmol), Na$_2$CO$_3$ (557 mg, 5.26 mmol), DMAP (48 mg, 0.393 mmol) and DMSO (3 mL) was heated to 80 overnight.

Condition B: A mixture of 4-nitrophenyl 4-(1-(4-fluorobenzamido)-3-methylbutyl) piperidine-1-carboxylate (120 mg, 0.262 mmol), 2,3-dimethylphenol (160 mg, 1.31 mmol), Cs$_2$CO$_3$ (427 mg, 1.31 mmol) and DMSO (3 mL) was heated to 140° C. for 2 hours by microwave.

The reaction mixture was partitioned between EtOAc/H$_2$O, and the layers were separated. The organic layer was washed with brine and dried over Na$_2$SO$_4$. Solvent was removed under vacuum and the residue was purified by Gilson (C18, 50-100% MeCN in water with 0.1% formic acid) to afford the title compound as a white solid. $^1$H NMR (400 MHz, DMSO) δ 8.09 (d, J=9.0 Hz, 1H), 7.97-7.89 (m, 2H), 7.34-7.26 (m, 2H), 7.09-6.98 (m, 2H), 6.84 (d, J=7.6 Hz, 1H), 4.26-4.13 (m, 1H), 4.09-3.93 (m, 2H), 3.04-2.92 (m, 1H), 2.86-2.73 (m, 1H), 2.23 (s, 3H), 1.97 (s, 3H), 1.80-1.52 (m, 5H), 1.34-1.16 (m, 3H), 0.94-0.78 (m, 6H). LCMS (ESI) m/z calcd for C$_{26}$H$_{33}$FN$_2$O$_3$: 440.25. Found: 441.26 (M+1)$^+$.

The following compounds were prepared according to the procedure described above using the appropriate materials.

Example 2

2-methylpyridin-3-yl 4-(3-methyl-1-(5-methylthiophene-2-carboxamido)butyl) Piperidine-1-carboxylate

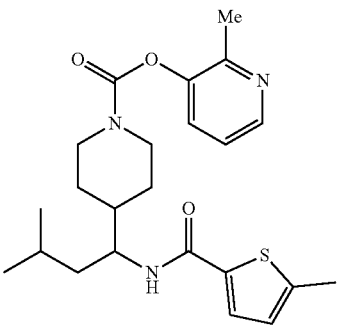 [SMILES: Cc1ccc(C(=O)NC(CC(C)C)C2CCN(C(=O)Oc3cccnc3C)CC2)s1]

$^1$H NMR (400 MHz, METHANOL-d$_4$) δ ppm 8.27 (d, J=4.7 Hz, 1H) 7.53 (d, J=3.3 Hz, 2H) 7.18-7.37 (m, 1H) 6.81 (d, J=3.5 Hz, 1H) 4.26-4.47 (m, 1H) 4.11-4.23 (m, 1H) 3.95-4.08 (m, 1H) 2.97-3.20 (m, 1H) 2.74-2.97 (m, 1H) 2.51 (s, 3H) 2.37 (d, J=14.4 Hz, 3H) 1.51-1.95 (m, 5H) 1.22-1.47 (m, 3H) 0.94 (dd, J=10.1, 6.5 Hz, 6H). LCMS m/z calcd for C23H31N3O3S: 429.5. Found: 430.3 (M+1)$^+$.

Example 3

2,4-dimethylpyridin-3-yl 4-(1-(4-chlorobenzamido)-3-methylbutyl)piperidine-1-carboxylate

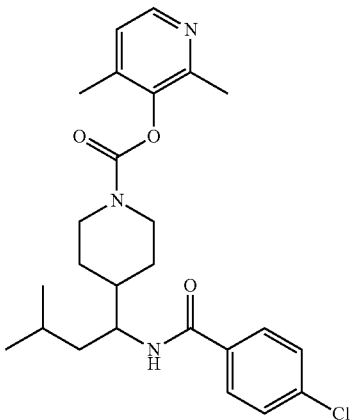 [SMILES: Cc1ccnc(C)c1OC(=O)N1CCC(C(CC(C)C)NC(=O)c2ccc(Cl)cc2)CC1]

$^1$H NMR (400 MHz, METHANOL-d$_4$) δ ppm 8.12 (d, J=4.9 Hz, 1H) 7.80 (d, J=8.4 Hz, 2H) 7.48 (d, J=8.4 Hz, 2H) 7.16 (d, J=3.9 Hz, 1H) 4.29-4.50 (m, 1H) 4.01-4.26 (m, 2H) 2.99-3.19 (m, 1H) 2.74-2.99 (m, 1H) 2.32 (d, J=12.7 Hz, 3H) 2.18 (d, J=10.5 Hz, 3H) 1.71-1.97 (m, 3H) 1.54-1.71 (m, 2H) 1.20-1.51 (m, 3H) 0.84-1.01 (m, 6H) LCMS m/z calcd for C25H32ClN3O3: 457.99 Found: 458.7 (M+1)$^+$.

Example 4

2-methylpyridin-3-yl 4-(1-(5-chlorothiophene-2-carboxamido)-3-methylbutyl) Piperidine-1-carboxylate

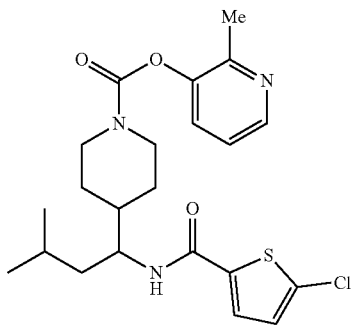 [SMILES: Cc1ncccc1OC(=O)N1CCC(C(CC(C)C)NC(=O)c2ccc(Cl)s2)CC1]

$^1$H NMR (400 MHz, METHANOL-d$_4$) δ ppm 8.27 (d, J=4.7 Hz, 1H) 7.58 (d, J=3.9 Hz, 1H) 7.52 (d, J=8.0 Hz, 1H) 7.30 (dd, J=7.7, 5.2 Hz, 1H) 7.03 (d, J=3.7 Hz, 1H) 4.29-4.46 (m, 1H) 4.13-4.25 (m, 1H) 3.96-4.10 (m, 1H) 2.96-3.16 (m, 1H) 2.79-2.96 (m, 1H) 2.38 (d, J=11.7 Hz, 3H) 1.51-1.93 (m, 5H) 1.21-1.48 (m, 3H) 0.94 (dd, J=11.9, 6.4 Hz, 6H).

LCMS m/z calcd for C22H28ClN3O3S: 449.99 Found: 450.2 (M+1)$^+$.

Example 5

2-cyanopyridin-3-yl 4-(1-(4-chlorobenzamido)-3-methylbutyl)piperidine-1-carboxylate

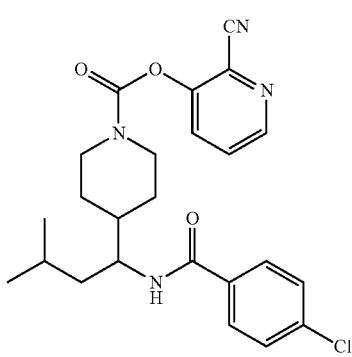 [SMILES: CC(C)CC(NC(=O)c1ccc(Cl)cc1)C1CCN(C(=O)Oc2cccnc2C#N)CC1]

$^1$H NMR (400 MHz, METHANOL-d$_4$) δ ppm 8.54 (d, J=4.3 Hz, 1H) 7.89 (d, J=8.6 Hz, 1H) 7.79 (d, J=8.2 Hz, 2H) 7.71 (dd, J=8.4, 4.7 Hz, 1H) 7.47 (d, J=8.4 Hz, 2H) 4.33-4.47 (m, 1H) 4.05-4.27 (m, 2H) 3.03-3.19 (m, 1H) 2.83-3.02 (m, 1H) 1.72-1.95 (m, 3H) 1.55-1.72 (m, 2H) 1.31-1.55 (m, 3H) 0.95 (t, J=6.3 Hz, 6H). LCMS m/z calcd for C24H27ClN4O3: 454.18 Found: 455.23 (M+1)$^+$.

Example 6

2-methylpyridin-3-yl 4-(1-(4-chlorobenzamido)-3-methylbutyl)piperidine-1-carboxylate

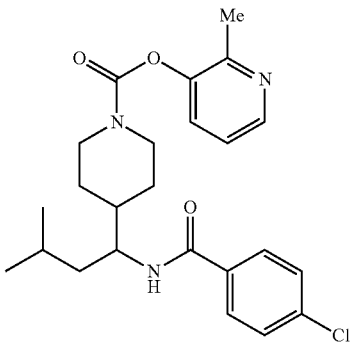

$^1$H NMR (400 MHz, METHANOL-d$_4$) δ ppm 8.27 (d, J=4.3 Hz, 1H) 7.80 (d, J=8.4 Hz, 2H) 7.41-7.60 (m, 3H) 7.23-7.37 (m, 1H) 4.28-4.48 (m, 1H) 4.15-4.25 (m, 1H) 4.06-4.15 (m, 1H) 2.98-3.16 (m, 1H) 2.79-2.95 (m, 1H) 2.38 (d, J=10.7 Hz, 3H) 1.69-1.97 (m, 2H) 1.62 (d, J=13.5 Hz, 2H) 1.23-1.48 (m, 4H) 0.95 (t, J=6.9 Hz, 6H) LCMS m/z calcd for C24H30ClN3O3: 443.97 Found: 444.26 (M+1)$^+$.

Example 10

2-methoxypyridin-3-yl 4-(1-(4-chlorobenzamido)-3-methylbutyl)piperidine-1-carboxylate

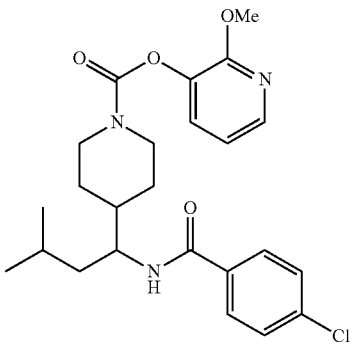 [SMILES: COc1ncccc1OC(=O)N1CCC(C(CC(C)C)NC(=O)c2ccc(Cl)cc2)CC1]

$^1$H NMR (400 MHz, METHANOL-d$_4$) δ ppm 7.97 (d, J=4.5 Hz, 1H) 7.81 (d, J=8.4 Hz, 2H) 7.48 (d, J=8.4 Hz, 2H) 7.41 (d, J=7.6 Hz, 1H) 6.95 (dd, J=7.5, 5.2 Hz, 1H) 4.25-4.38 (m, 1H) 4.04-4.22 (m, 2H) 3.87 (d, J=15.0 Hz, 3H) 2.94-3.11 (m, 1H) 2.78-2.94 (m, 1H) 1.52-1.93 (m, 5H) 1.25-1.48 (m, 3H) 0.95 (t, J=6.8 Hz, 6H) LCMS m/z calcd for C24H30ClN3O4: 459.97 Found: 460.34 (M+1)$^+$.

Example 11

2-chloro-3-fluorophenyl 4-(1-(4-fluorobenzamido)-3-methylbutyl)piperidine-1-carboxylate

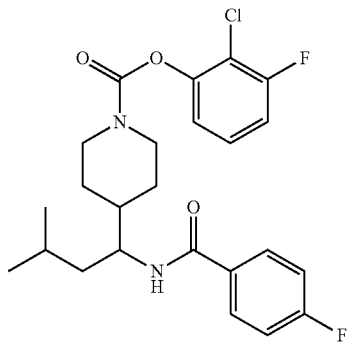 [SMILES: CC(C)CC(NC(=O)c1ccc(F)cc1)C1CCN(C(=O)Oc2cccc(F)c2Cl)CC1]

¹H NMR (400 MHz, METHANOL-d₄) δ ppm 7.87 (dd, J=7.6, 5.7 Hz, 2H) 7.27-7.42 (m, 1H) 7.10-7.26 (m, 3H) 7.07 (d, J=7.6 Hz, 1H) 4.36 (d, J=11.3 Hz, 1H) 4.03-4.25 (m, 2H) 3.06 (d, J=11.9 Hz, 1H) 2.90 (d, J=11.5 Hz, 1H) 1.70-1.97 (m, 3H) 1.54-1.70 (m, 2H) 1.23-1.54 (m, 3H) 0.95 (t, J=6.3 Hz, 6H)

LCMS m/z calcd for C24H27ClF2N2O3: 464.93 Found: 465.29 (M+1)⁺.

Example 15

4,6-dimethylpyrimidin-5-yl 4-(1-(4-chlorobenzamido)-3-methylbutyl)piperidine-1-carboxylate

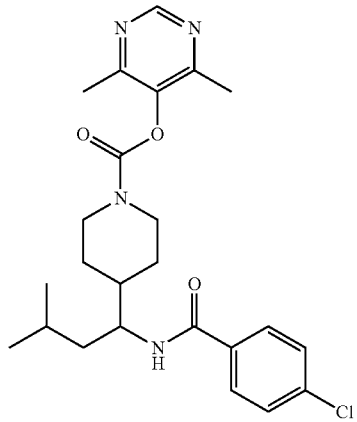 [SMILES: Cc1ncnc(C)c1OC(=O)N1CCC(C(CC(C)C)NC(=O)c2ccc(Cl)cc2)CC1]

¹H NMR (400 MHz, METHANOL-d₄) δ ppm 8.70 (s, 1H) 7.80 (d, J=8.6 Hz, 2H) 7.48 (d, J=8.6 Hz, 2H) 4.29-4.49 (m, 1H) 3.99-4.25 (m, 2H) 3.00-3.21 (m, 1H) 2.82-3.03 (m, 1H) 2.37 (s, 3H) 2.34 (s, 3H) 1.71-1.97 (m, 3H) 1.54-1.72 (m, 2H) 1.21-1.48 (m, 3H) 0.95 (t, J=6.9 Hz, 6H)

LCMS m/z calcd for C24H31ClN4O3: 458.98 Found: 459.31 (M+1)⁺.

Example 18

2-methylpyridin-3-yl 4-(1-(4-fluorobenzamido)-3-methylbutyl)piperidine-1-carboxylate

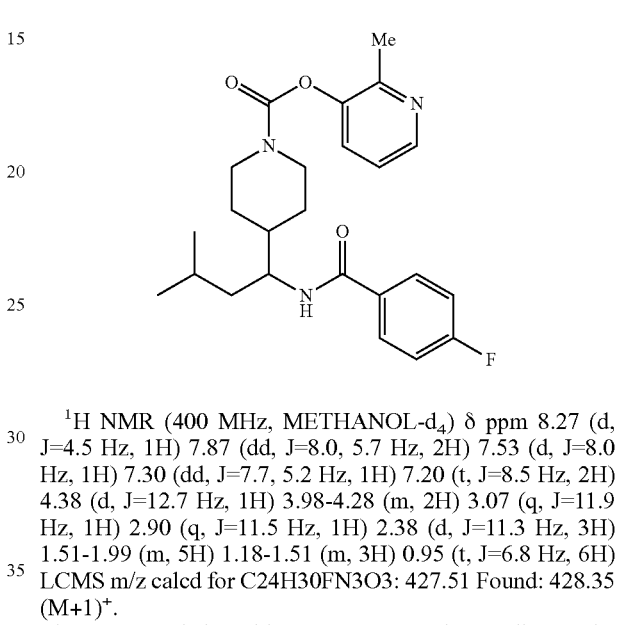

¹H NMR (400 MHz, METHANOL-d₄) δ ppm 8.27 (d, J=4.5 Hz, 1H) 7.87 (dd, J=8.0, 5.7 Hz, 2H) 7.53 (d, J=8.0 Hz, 1H) 7.30 (dd, J=7.7, 5.2 Hz, 1H) 7.20 (t, J=8.5 Hz, 2H) 4.38 (d, J=12.7 Hz, 1H) 3.98-4.28 (m, 2H) 3.07 (q, J=11.9 Hz, 1H) 2.90 (q, J=11.5 Hz, 1H) 2.38 (d, J=11.3 Hz, 3H) 1.51-1.99 (m, 5H) 1.18-1.51 (m, 3H) 0.95 (t, J=6.8 Hz, 6H)

LCMS m/z calcd for C24H30FN3O3: 427.51 Found: 428.35 (M+1)⁺.

The compounds in Table 1 were prepared according to the above procedures using appropriate materials.

TABLE 1

| Example | Structure | Synthesized using conditions | Exact mass | M + 1 observed |
|---|---|---|---|---|
| 44 | 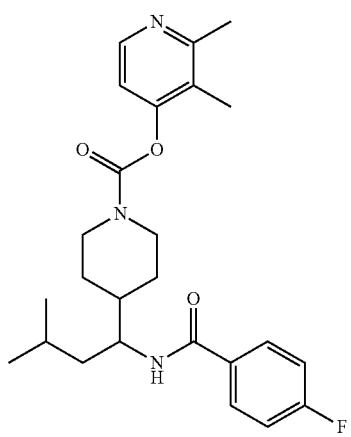 [SMILES: Cc1nccc(OC(=O)N2CCC(C(CC(C)C)NC(=O)c3ccc(F)cc3)CC2)c1C] | A | 441.24 | 442.28 |

TABLE 1-continued
| Example | Structure | Synthesized using conditions | Exact mass | M + 1 observed |
|---------|-----------|------------------------------|------------|----------------|
| 79 | 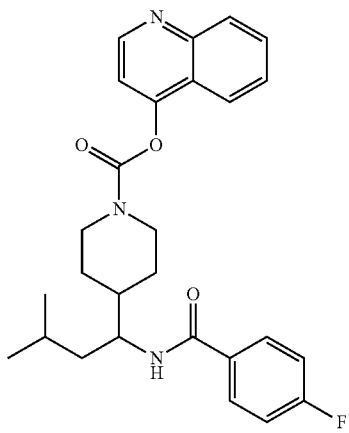 [SMILES: CC(C)CC(NC(=O)c1ccc(F)cc1)C1CCN(C(=O)Oc2ccnc3ccccc23)CC1] | A | 463.23 | 464.29 |
| 55 | 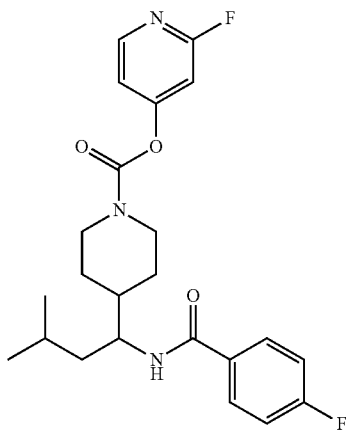 [SMILES: CC(C)CC(NC(=O)c1ccc(F)cc1)C1CCN(C(=O)Oc2ccnc(F)c2)CC1] | A | 431.20 | 432.28 |
| 22 | 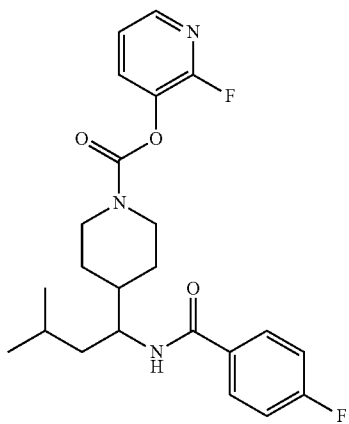 [SMILES: CC(C)CC(NC(=O)c1ccc(F)cc1)C1CCN(C(=O)Oc2cccnc2F)CC1] | A | 431.20 | 432.29 |

TABLE 1-continued
| Example | Structure | Synthesized using conditions | Exact mass | M + 1 observed |
|---------|-----------|------------------------------|------------|----------------|
| 48 | 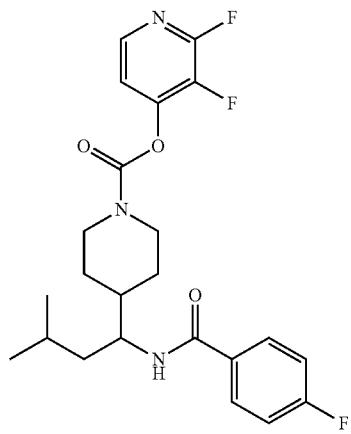 [SMILES: CC(C)CC(NC(=O)c1ccc(F)cc1)C1CCN(C(=O)Oc2ccnc(F)c2F)CC1] | A | 449.19 | 450.54 |
| 50 | 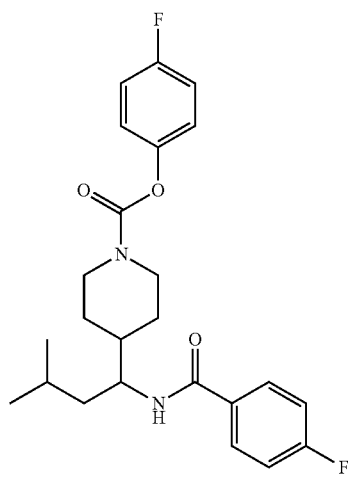 [SMILES: CC(C)CC(NC(=O)c1ccc(F)cc1)C1CCN(C(=O)Oc2ccc(F)cc2)CC1] | A | 430.21 | 431.22 |
| 40 | 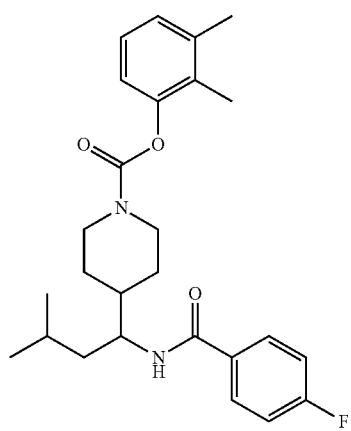 [SMILES: Cc1cccc(OC(=O)N2CCC(C(CC(C)C)NC(=O)c3ccc(F)cc3)CC2)c1C] | A | 440.25 | 441.26 |

TABLE 1-continued
| Example | Structure | Synthesized using conditions | Exact mass | M + 1 observed |
|---------|-----------|------------------------------|------------|----------------|
| 9 | 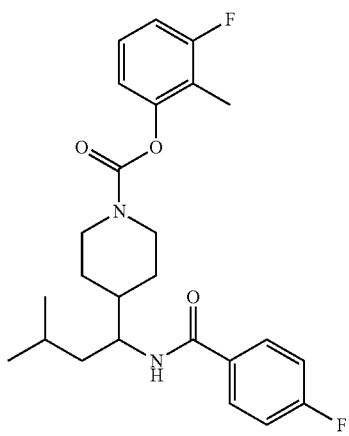 [SMILES: Cc1c(F)cccc1OC(=O)N1CCC(C(CC(C)C)NC(=O)c2ccc(F)cc2)CC1] | A | 444.22 | 445.25 |
| 54 | 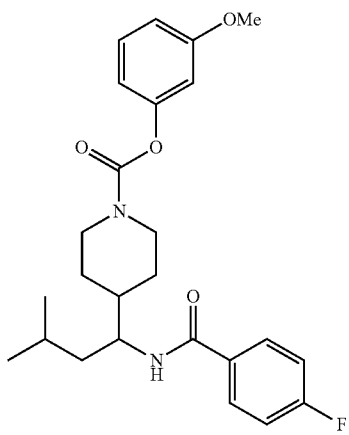 [SMILES: COc1cccc(OC(=O)N2CCC(C(CC(C)C)NC(=O)c3ccc(F)cc3)CC2)c1] | A | 442.23 | 443.23 |
| 59 | 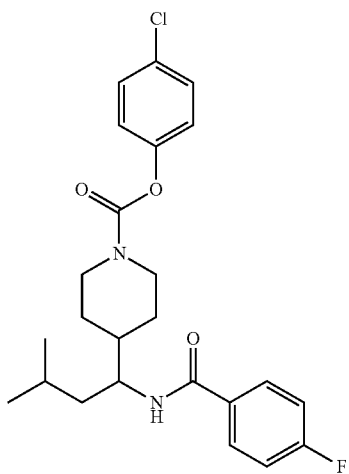 [SMILES: CC(C)CC(NC(=O)c1ccc(F)cc1)C1CCN(C(=O)Oc2ccc(Cl)cc2)CC1] | A | 446.18 | 449.17 |

TABLE 1-continued

| Example | Structure | Synthesized using conditions | Exact mass | M + 1 observed |
|---------|-----------|------------------------------|------------|----------------|
| 60 | 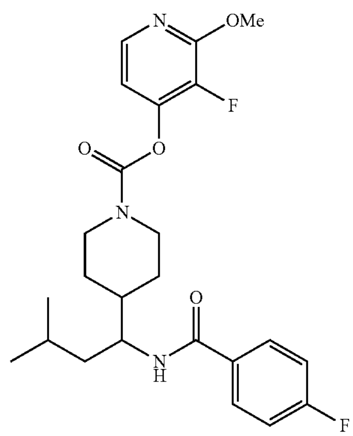 [SMILES: COc1nccc(OC(=O)N2CCC(C(CC(C)C)NC(=O)c3ccc(F)cc3)CC2)c1F] | B | 461.21 | 462.30 |
| 47 | 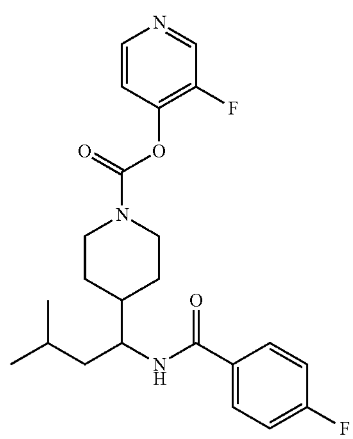 [SMILES: CC(C)CC(NC(=O)c1ccc(F)cc1)C1CCN(C(=O)Oc2ccncc2F)CC1] | A | 431.20 | 432.43 |
| 45 | 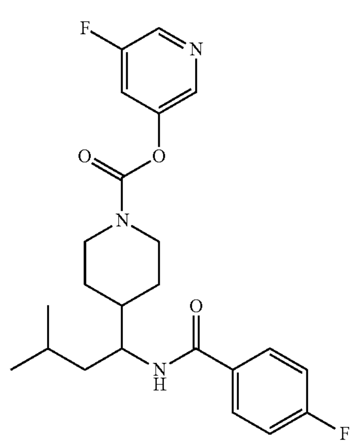 [SMILES: CC(C)CC(NC(=O)c1ccc(F)cc1)C1CCN(C(=O)Oc2cncc(F)c2)CC1] | A | 431.20 | 432.38 |

TABLE 1-continued

| Example | Structure | Synthesized using conditions | Exact mass | M + 1 observed |
|---------|-----------|------------------------------|-----------|----------------|
| 51 | 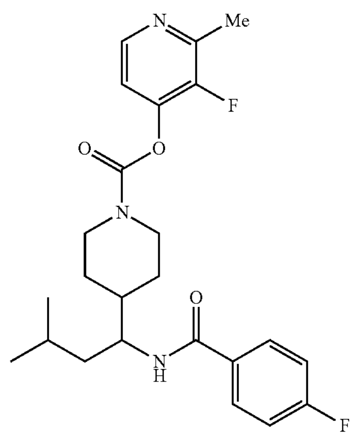 [SMILES: Cc1nccc(OC(=O)N2CCC(C(CC(C)C)NC(=O)c3ccc(F)cc3)CC2)c1F] | B | 445.22 | 446.25 |
| 28 | 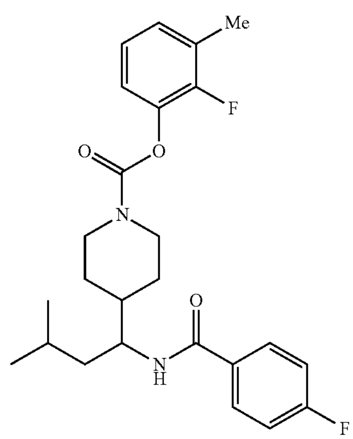 [SMILES: Cc1cccc(OC(=O)N2CCC(C(CC(C)C)NC(=O)c3ccc(F)cc3)CC2)c1F] | A | 444.22 | 445.51 |
| 13 | 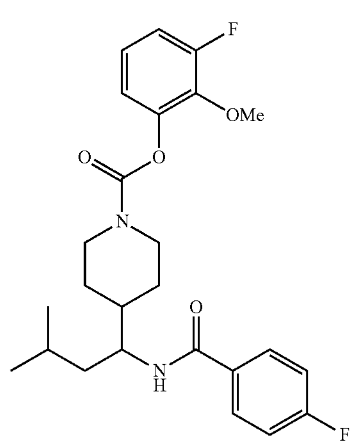 [SMILES: COc1c(F)cccc1OC(=O)N1CCC(C(CC(C)C)NC(=O)c2ccc(F)cc2)CC1] | A | 460.22 | 461.35 |

TABLE 1-continued

| Example | Structure | Synthesized using conditions | Exact mass | M + 1 observed |
|---------|-----------|------------------------------|------------|----------------|
| 12 | 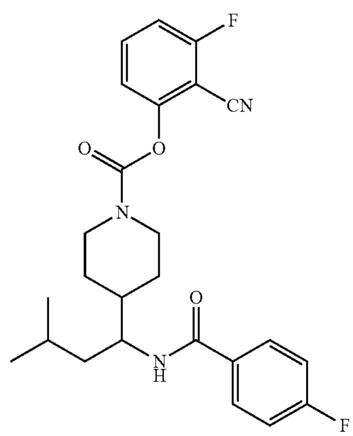 [SMILES: CC(C)CC(NC(=O)c1ccc(F)cc1)C1CCN(C(=O)Oc2cccc(F)c2C#N)CC1] | A | 455.20 | 456.40 |
| 41 | 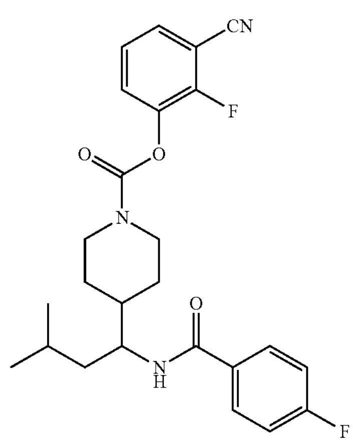 [SMILES: CC(C)CC(NC(=O)c1ccc(F)cc1)C1CCN(C(=O)Oc2cccc(C#N)c2F)CC1] | B | 455.20 | 456.54 |
| 29 | 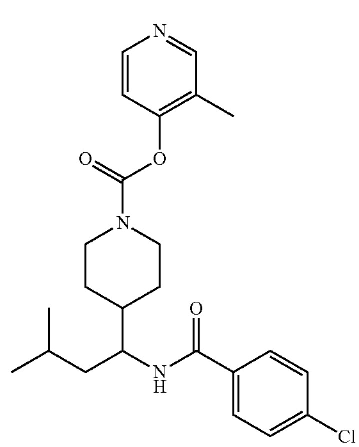 [SMILES: Cc1cnccc1OC(=O)N1CCC(C(CC(C)C)NC(=O)c2ccc(Cl)cc2)CC1] | A | 443.20 | 444.24 |

TABLE 1-continued
| Example | Structure | Synthesized using conditions | Exact mass | M + 1 observed |
|---------|-----------|------------------------------|------------|----------------|
| 30 | 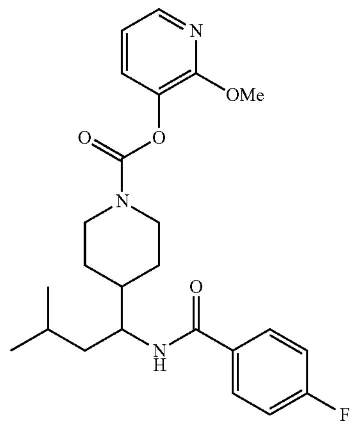 [SMILES: COc1ncccc1OC(=O)N1CCC(C(CC(C)C)NC(=O)c2ccc(F)cc2)CC1] | A | 443.22 | 444.28 |
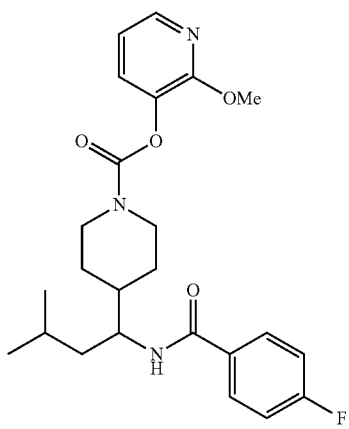
| 34 | | A | 471.23 | 472.19 |
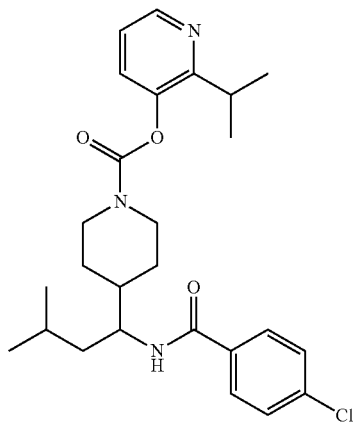 [SMILES: CC(C)CC(NC(=O)c1ccc(Cl)cc1)C1CCN(C(=O)Oc2cccnc2C(C)C)CC1]
| 35 | | A | 457.21 | 458.27 |
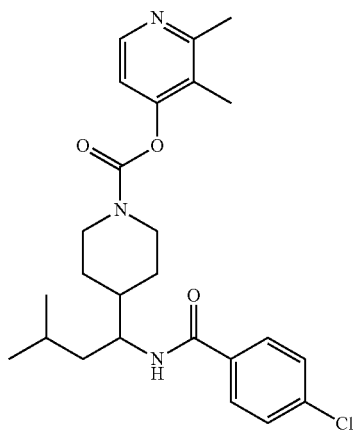 [SMILES: Cc1nccc(OC(=O)N2CCC(C(CC(C)C)NC(=O)c3ccc(Cl)cc3)CC2)c1C]

TABLE 1-continued

| Example | Structure | Synthesized using conditions | Exact mass | M + 1 observed |
|---|---|---|---|---|
| 108 | 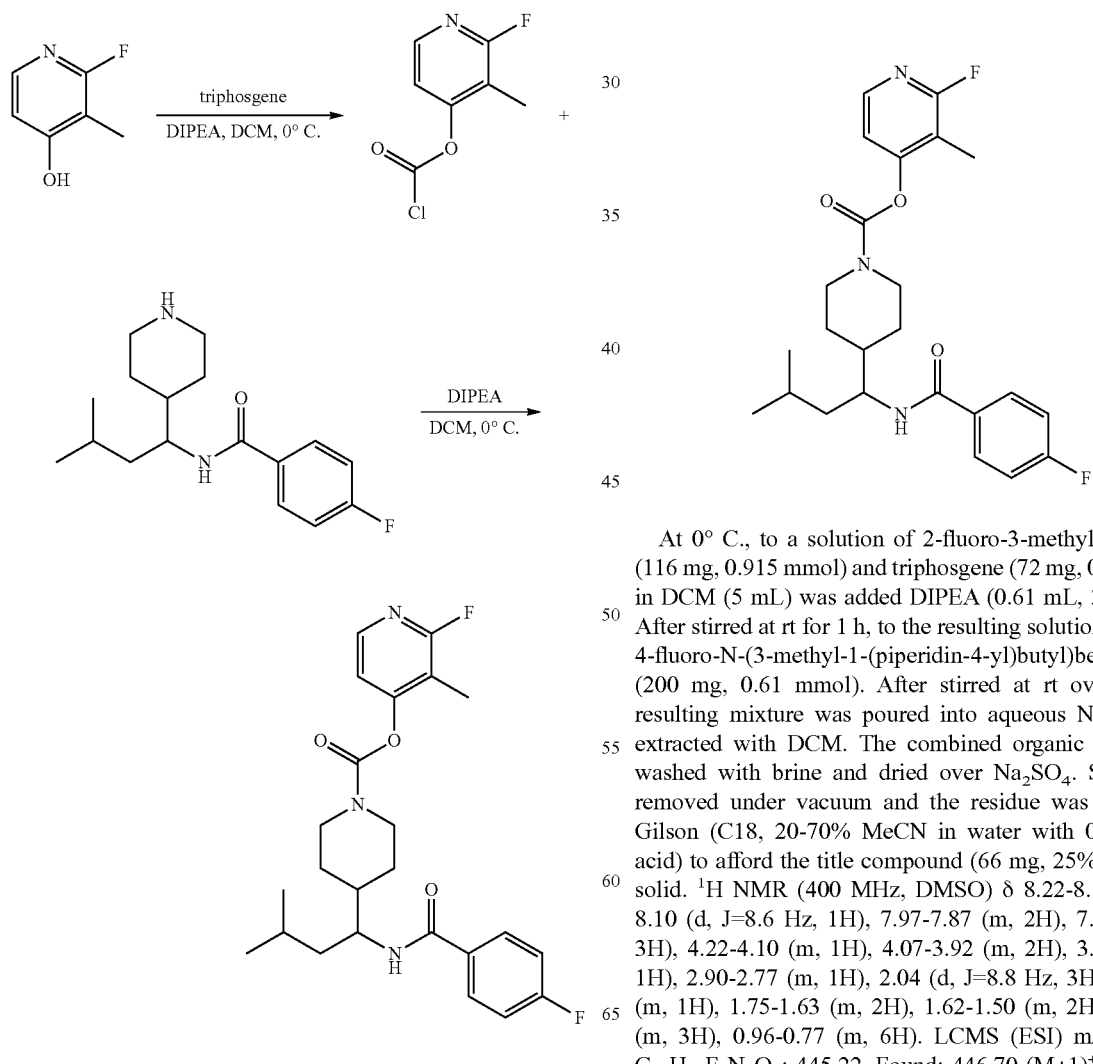 | A | 468.98 | 469.39 |

Example 33

Preparation of 2-fluoro-3-methylpyridin-4-yl 4-(1-(4-fluorobenzamido)-3-methyl butyl)piperidine-1-carboxylate At 0° C., to a solution of 2-fluoro-3-methylpyridin-4-ol (116 mg, 0.915 mmol) and triphosgene (72 mg, 0.242 mmol) in DCM (5 mL) was added DIPEA (0.61 mL, 3.65 mmol). After stirred at rt for 1 h, to the resulting solution was added 4-fluoro-N-(3-methyl-1-(piperidin-4-yl)butyl)benzamide (200 mg, 0.61 mmol). After stirred at rt overnight, the resulting mixture was poured into aqueous $NaHCO_3$ and extracted with DCM. The combined organic layers were washed with brine and dried over $Na_2SO_4$. Solvent was removed under vacuum and the residue was purified by Gilson (C18, 20-70% MeCN in water with 0.1% formic acid) to afford the title compound (66 mg, 25%) as a white solid. $^1$H NMR (400 MHz, DMSO) δ 8.22-8.14 (m, 1H), 8.10 (d, J=8.6 Hz, 1H), 7.97-7.87 (m, 2H), 7.35-7.20 (m, 3H), 4.22-4.10 (m, 1H), 4.07-3.92 (m, 2H), 3.07-2.95 (m, 1H), 2.90-2.77 (m, 1H), 2.04 (d, J=8.8 Hz, 3H), 1.83-1.75 (m, 1H), 1.75-1.63 (m, 2H), 1.62-1.50 (m, 2H), 1.35-1.15 (m, 3H), 0.96-0.77 (m, 6H). LCMS (ESI) m/z calcd for $C_{24}H_{29}F_2N_3O_3$: 445.22. Found: 446.70 (M+1)$^+$.

Example 39

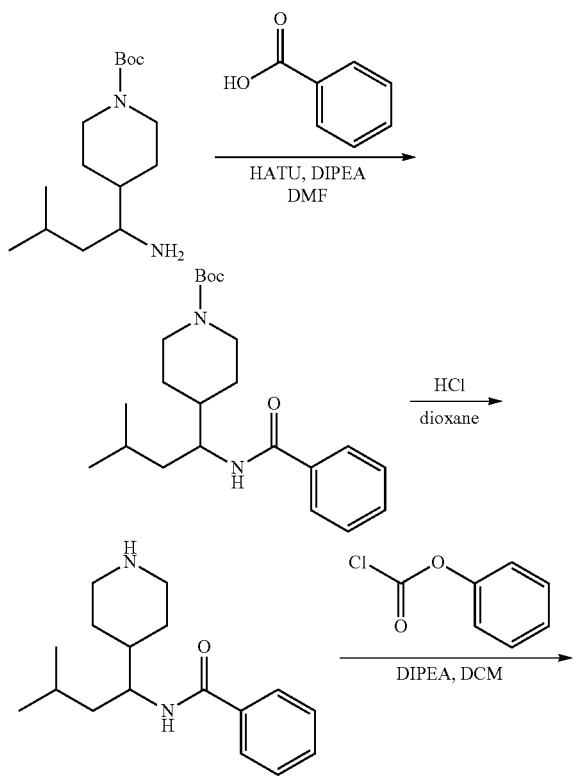

Preparation of Tert-butyl 4-(1-benzamido-3-methylbutyl)piperidine-1-carboxylate

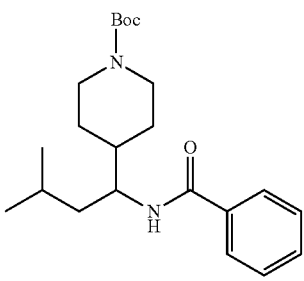 [SMILES: CC(C)CC(NC(=O)c1ccccc1)C1CCN(C(=O)OC(C)(C)C)CC1]

To a solution of tert-butyl 4-(1-amino-3-methylbutyl)piperidine-1-carboxylate (200 mg, 0.74 mmol) in DMF (2 mL), was added benzoic acid (100 mg, 0.82 mmol), DIPEA (0.4 mL, 2.22 mmol) and HATU (422 mg, 1.11 mmol) successively. After stirred at r.t. for 3 h, the reaction was diluted with water and extracted with EtOAc. The organic layer was washed with brine, dried over $Na_2SO_4$, filtered and concentrated to give the crude product which was purified by flash chromatography (silica gel, 0-50% EtOAc in PE) to afford the title compound (183 mg, 66% yield). LCMS (ESI) m/z calcd for $C_{22}H_{34}N_2O_3$: 374.26. Found: 375.34 $(M+1)^+$.

Preparation of N-(3-methyl-1-(piperidin-4-yl)butyl)benzamide

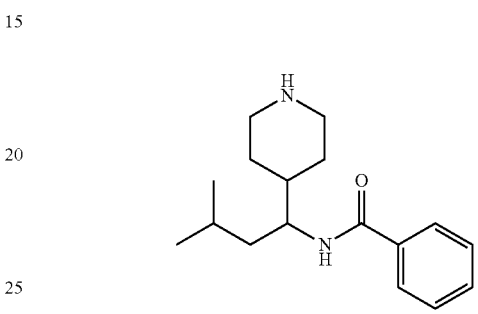

To a solution of tert-butyl 4-(1-benzamido-3-methylbutyl)piperidine-1-carboxylate (183 mg, 0.49 mmol) in DCM (2 mL), was added 4 M HCl in dioxane (4 mL) dropwise. After stirred at r.t. for 1 h, the reaction mixture was concentrated to to afford the title compound (166 mg, 100% yield), which was used in the following step without purification. LCMS (ESI) m/z calcd for $C_{17}H_{26}N_2O$: 274.20. Found: 275.43 $(M+1)^+$.

Preparation of Phenyl 4-(1-benzamido-3-methylbutyl)piperidine-1-carboxylate

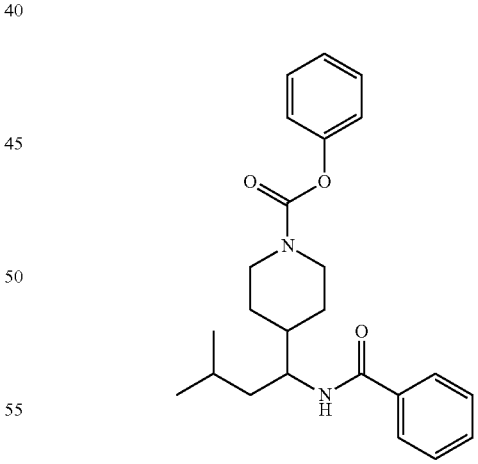

At 0° C., to a solution of N-(3-methyl-1-(piperidin-4-yl)butyl)benzamide (166 mg, 0.6 mmol) and DIPEA (0.32 mL, 1.8 mmol) in DCM (3 mL), was added phenyl carbonochloridate (0.12 mL, 0.9 mmol) drop wise. After stirred at r.t. for 2 h, the reaction was quenched with saturated $NaHCO_3$ aq. solution and extracted with EtOAc. The organic layer was washed with brine and dried over $Na_2SO_4$. Solvent was removed under vacuum and the residue was purified by Gilson (C18, 50-100% MeCN in water with 0.1% formic acid) to afford the title compound (103 mg, 43%) as a white solid. ¹H NMR (400 MHz, DMSO) δ 8.06 (d, J=9.1 Hz, 1H), 7.90-7.81 (m, 2H), 7.56-7.49 (m, 1H), 7.49-7.42 (m, 2H), 7.36 (t, J=7.8 Hz, 2H), 7.20 (t, J=7.4 Hz, 1H), 7.09 (d, J=7.8 Hz, 2H), 4.26-4.11 (m, 1H), 4.10-3.94 (m, 2H), 3.05-2.75 (m, 2H), 1.74-1.51 (m, 4H), 1.38-1.10 (m, 4H), 0.96-0.77 (m, 6H). LCMS (ESI) m/z calcd for $C_{24}H_{30}N_2O_3$: 394.23. Found: 395.36 (M+1)⁺.

Example 26

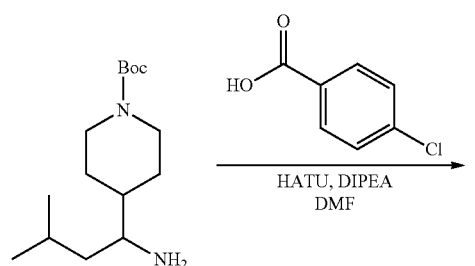

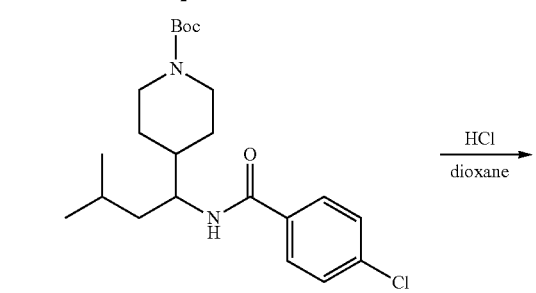

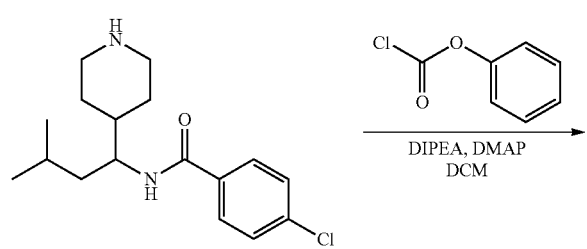

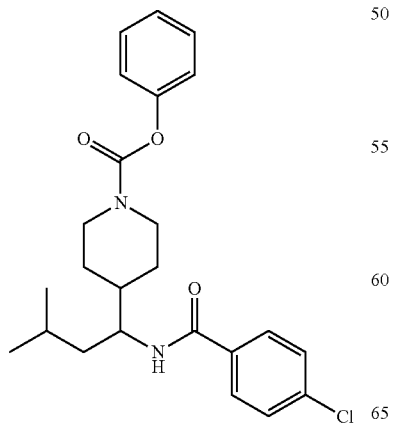

Preparation of Tert-butyl 4-(1-(4-chlorobenzamido)-3-methylbutyl)piperidine-1-carboxylate

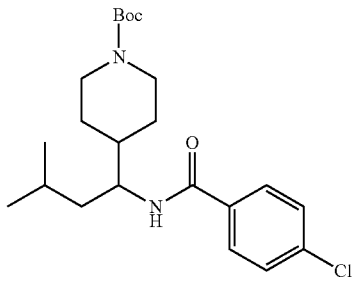 [SMILES: CC(C)CC(NC(=O)c1ccc(Cl)cc1)C1CCN(C(=O)OC(C)(C)C)CC1]

To a solution of tert-butyl 4-(1-amino-3-methylbutyl)piperidine-1-carboxylate (200 mg, 0.74 mmol) in DMF (2 mL), was added 4-chlorobenzoic acid (130 mg, 0.82 mmol), DIPEA (0.4 mL, 2.22 mmol) and HATU (422 mg, 1.11 mmol) successively. After stirred at r.t. for 3 h, the reaction was diluted with water and extracted with EtOAc. The organic layer was washed with brine, dried over $Na_2SO_4$, filtered and concentrated to give the crude product which was purified by flash chromatography (silica gel, 0-50% EtOAc in PE) to afford the title compound (205 mg, 68% yield). LCMS (ESI) m/z calcd for $C_{22}H_{33}ClN_2O_3$: 408.22. Found: 409.27/411.27 (M/M+2)⁺.

Preparation of 4-chloro-N-(3-methyl-1-(piperidin-4-yl)butyl)benzamide

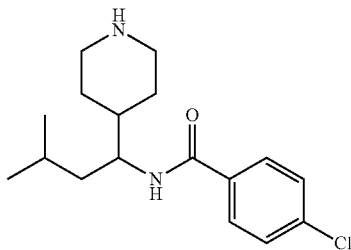 [SMILES: CC(C)CC(NC(=O)c1ccc(Cl)cc1)C1CCNCC1]

To a solution of tert-butyl tert-butyl 4-(1-(4-chlorobenzamido)-3-methylbutyl)piperidine-1-carboxylate (205 mg, 0.50 mmol) in DCM (2 mL), was added 4 M HCl in dioxane (4 mL) dropwise. After stirred at r.t. for 2 h, the reaction mixture was concentrated to to afford the title compound (180 mg, 100% yield), which was used in the following step without purification. LCMS (ESI) m/z calcd for $C_{17}H_{25}ClN_2O$: 308.17. Found: 309.22/311.26 (M/M+2)⁺.

Preparation of Phenyl 4-(1-(4-chlorobenzamido)-3-methylbutyl)piperidine-1-carboxylate

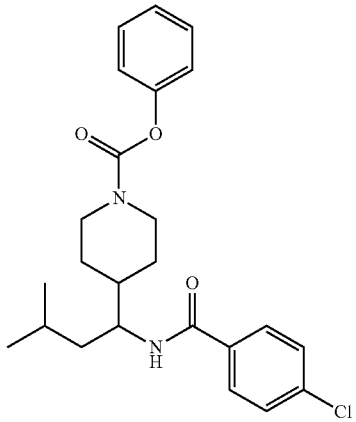 [SMILES: CC(C)CC(NC(=O)c1ccc(Cl)cc1)C1CCN(C(=O)Oc2ccccc2)CC1]

At 0° C., to a solution of 4-chloro-N-(3-methyl-1-(piperidin-4-yl)butyl)benzamide (143 mg, 0.46 mmol), DIPEA (0.24 mL, 1.38 mmol) and DMAP (3 mg, 0.023 mmol) in DCM (2 mL), was added phenyl carbonochloridate (0.09 mL, 0.70 mmol) drop wise. After stirred at r.t. for 2 h, the reaction was quenched with saturated NaHCO$_3$ aq. solution and extracted with EtOAc. The organic layer was washed with aq. NaHCO$_3$, brine and dried over Na$_2$SO$_4$. Solvent was removed under vacuum and the residue was purified by Gilson (C18, 10-50% MeCN in water with 0.1% formic acid) to afford the title compound (112 mg, 57% yield) as a white solid. $^1$H NMR (400 MHz, DMSO) δ 8.15 (d, J=8.9 Hz, 1H), 7.88 (d, J=8.5 Hz, 2H), 7.54 (d, J=8.5 Hz, 2H), 7.36 (t, J=7.7 Hz, 2H), 7.20 (t, J=7.3 Hz, 1H), 7.09 (d, J=7.7 Hz, 2H), 4.28-4.13 (m, 1H), 4.13-3.96 (m, 2H), 3.01-2.79 (m, 2H), 1.74-1.53 (m, 4H), 1.32-1.21 (m, 4H), 0.95-0.79 (m, 6H). LCMS (ESI) m/z calcd for C$_{24}$H$_{29}$ClN$_2$O$_3$: 428.19. Found: 429.19/431.18 (M/M+2)$^+$.

Example 16

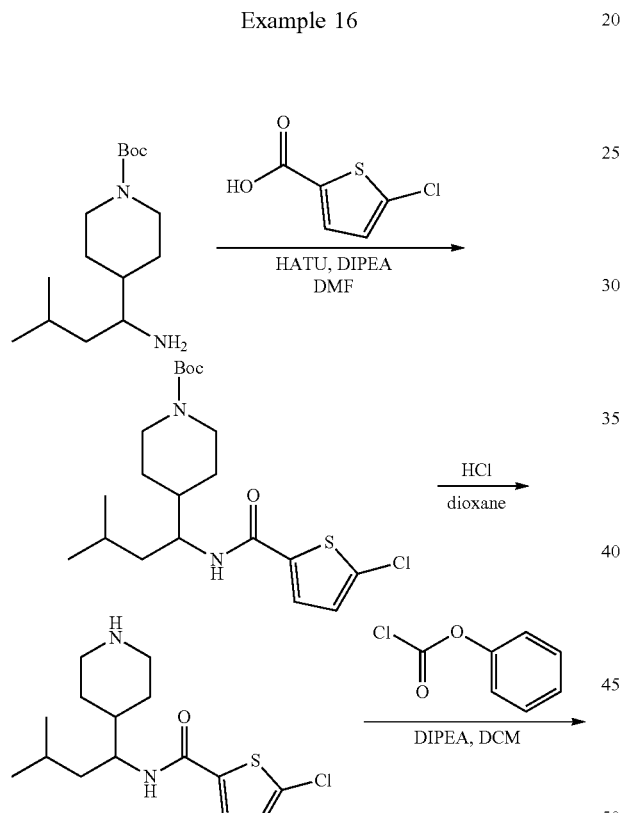

Preparation of Tert-butyl 4-(1-(5-chlorothiophene-2-carboxamido)-3-methylbutyl) Piperidine-1-carboxylate

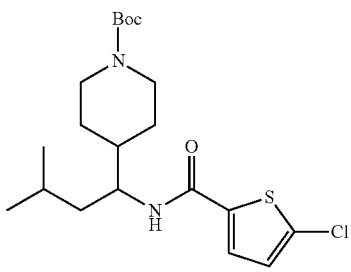 [SMILES: CC(C)CC(NC(=O)c1ccc(Cl)s1)C1CCN(C(=O)OC(C)(C)C)CC1]

To a solution of tert-butyl 4-(1-amino-3-methylbutyl) piperidine-1-carboxylate (374 mg, 1.38 mmol) in DMF (5 mL), was added 5-chlorothiophene-2-carboxylic acid (225 mg, 1.38 mmol), DIPEA (0.69 mL, 4.13 mmol) and HATU (632 mg, 1.66 mmol) successively. After stirred at r.t. for 3 h, the reaction was diluted with water and extracted with EtOAc. The organic layer was washed with brine, dried over Na$_2$SO$_4$, filtered and concentrated to give the crude product which was purified by flash chromatography (silica gel, 0-30% EtOAc in PE) to afford the title compound (543 mg, 94% yield). LCMS (ESI) m/z calcd for C$_{20}$H$_{31}$ClN$_2$O$_3$S: 414.17. Found: 415.29/417.28 (M/M+2)$^+$.

Preparation of 5-chloro-N-(3-methyl-1-(piperidin-4-yl)butyl)thiophene-2-carboxamide

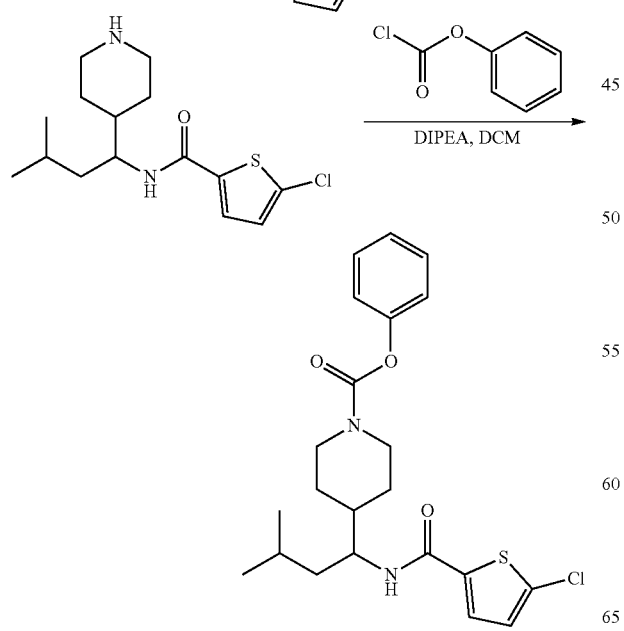

To a solution of tert-butyl 4-(1-(5-chlorothiophene-2-carboxamido)-3-methylbutyl) piperidine-1-carboxylate (543 mg, 1.31 mmol) in DCM (5 mL), was added 4 M HCl in dioxane (5 mL). After stirred at r.t. for 2 h, the reaction mixture was concentrated to afford the title compound (460 mg, 100% yield), which was used in the following step without purification. LCMS (ESI) m/z calcd for C$_{15}$H$_{23}$ClN$_2$OS: 314.12. Found: 315.27/317.26 (M/M+2)$^+$.

47

Preparation of Phenyl 4-(1-(5-chlorothiophene-2-carboxamido)-3-methylbutyl) Piperidine-1-carboxylate

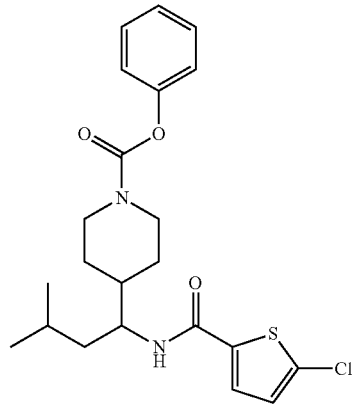 [SMILES: CC(C)CC(NC(=O)c1ccc(Cl)s1)C1CCN(C(=O)Oc2ccccc2)CC1]

At 0° C., to a solution of 5-chloro-N-(3-methyl-1-(piperidin-4-yl)butyl)thiophene-2-carboxamide (129 mg, 0.37 mmol) and DIPEA (0.29 mL, 1.85 mmol) in DCM (3 mL), was added phenyl carbonochloridate (87 mg, 0.555 mmol) drop wise. After stirred at r.t. for 2 h, the reaction was quenched with saturated NaHCO$_3$ aq. solution and extracted with EtOAc. The organic layer was washed with aq. NaHCO$_3$, brine and dried over Na$_2$SO$_4$. Solvent was removed under vacuum and the residue was purified by Gilson (C18, 10-60% MeCN in water with 0.1% formic acid) to afford the title compound (45 mg, 28% yield) as a white solid. $^1$H NMR (400 MHz, DMSO) δ 8.16 (d, J=9.1 Hz, 1H), 7.73 (d, J=4.1 Hz, 1H), 7.36 (t, J=7.9 Hz, 2H), 7.24-7.16 (m, 2H), 7.09 (d, J=7.7 Hz, 2H), 4.23-4.12 (m, 1H), 4.09-3.98 (m, 1H), 3.94-3.85 (m, 1H), 3.05-2.91 (m, 1H), 2.86-2.75 (m, 1H), 1.75-1.52 (m, 4H), 1.34-1.18 (m, 4H), 0.89 (d, J=6.5 Hz, 3H), 0.85 (d, J=6.4 Hz, 3H). LCMS (ESI) m/z calcd for C$_{22}$H$_{27}$ClN$_2$O$_3$S: 434.14. Found: 435.16/437.14 (M/M+2)$^+$.

Example 52

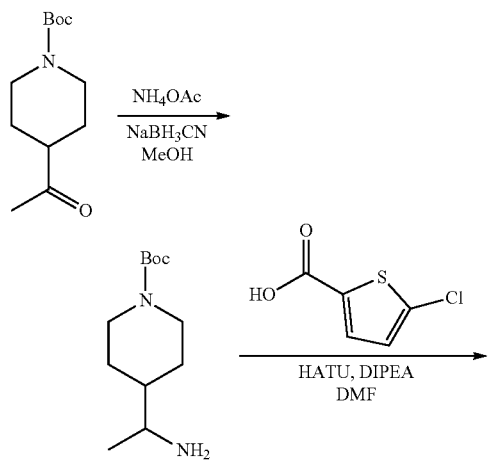

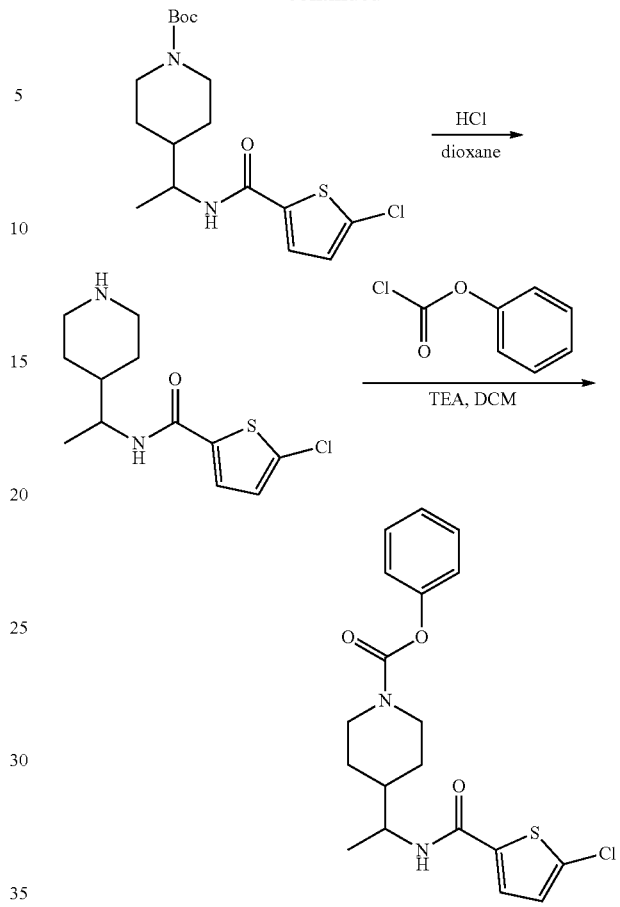

Preparation of Tert-butyl 4-(1-aminoethyl)piperidine-1-carboxylate

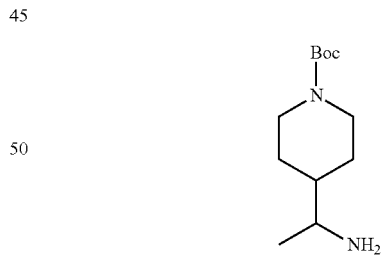

To a solution of tert-butyl 4-acetylpiperidine-1-carboxylate (620 mg, 2.73 mmol) in MeOH (10 mL), was added NH$_4$OAc (4.2 g, 54.55 mmol), and NaBH$_3$CN (1.71 g, 27.28 mmol) successively. After stirred at r.t. overnight, the reaction was diluted with water and extracted with DCM/$^i$PrOH. The organic layer was washed with brine, dried over Na$_2$SO$_4$, filtered and concentrated to give the crude product which was purified by flash chromatography (silica gel, 0-20% EtOAc in PE) to afford the title compound (550 mg, 88% yield). LCMS (ESI) m/z calcd for C$_{12}$H$_{24}$N$_2$O$_2$: 228.18. Found: 229.27 (M+1)$^+$.

Preparation of Tert-butyl 4-(1-(5-chlorothiophene-2-carboxamido)ethyl)piperidine-1-carboxylate

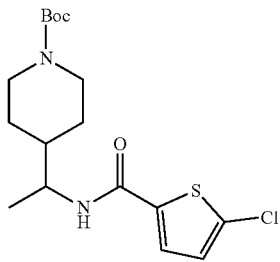 [SMILES: CC(NC(=O)c1ccc(Cl)s1)C1CCN(C(=O)OC(C)(C)C)CC1]

To a solution of tert-butyl 4-(1-aminoethyl)piperidine-1-carboxylate (550 mg, 2.41 mmol) in DMF (6 mL), was added 5-chlorothiophene-2-carboxylic acid (392 mg, 2.41 mmol), DIPEA (1.9 mL, 12.10 mmol) and HATU (1.01 g, 2.65 mmol) successively. After stirred at r.t. for 3 h, the reaction was diluted with water and extracted with EtOAc. The organic layer was washed with brine, dried over $Na_2SO_4$, filtered and concentrated to give the crude product which was purified by flash chromatography (silica gel, 0-30% EtOAc in PE) to afford the title compound (637 mg, 71% yield). LCMS (ESI) m/z calcd for $C_{17}H_{25}ClN_2O_3S$: 372.13. Found: 373.20/375.22 (M/M+2)$^+$.

Preparation of 5-chloro-N-(1-(piperidin-4-yl)ethyl)thiophene-2-carboxamide

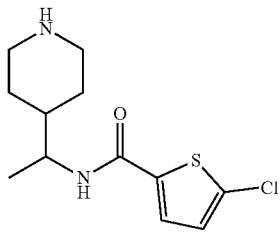 [SMILES: CC(NC(=O)c1ccc(Cl)s1)C1CCNCC1]

To a solution of tert-butyl 4-(1-(5-chlorothiophene-2-carboxamido)ethyl)piperidine-1-carboxylate (637 mg, 1.71 mmol) in DCM (4 mL), was added 4 M HCl in dioxane (6 mL) dropwise. After stirred at r.t. for 2 h, the reaction mixture was concentrated to to afford the title compound (529 mg, 100% yield), which was used in the following step without purification. LCMS (ESI) m/z calcd for $C_{12}H_{17}ClN_2OS$: 272.08. Found: 273.13/275.12 (M/M+2)$^+$.

Preparation of Phenyl 4-(1-(5-chlorothiophene-2-carboxamido)ethyl)piperidine-1-carboxylate

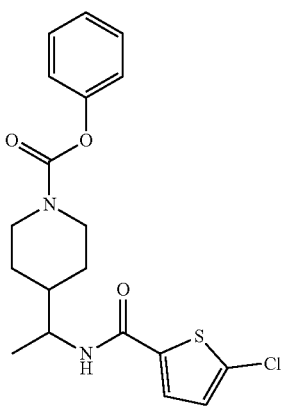

At 0° C., to a solution of 5-chloro-N-(1-(piperidin-4-yl)ethyl)thiophene-2-carboxamide (170 mg, 0.552 mmol) and TEA (0.39 mL, 2.76 mmol) in DCM (5 mL), was added phenyl carbonochloridate (95 mg, 0.607 mmol) drop wise. After stirred at r.t. for 2 h, the reaction was quenched with saturated $NaHCO_3$ aq. solution and extracted with EtOAc. The organic layer was washed with brine, dried over $Na_2SO_4$, filtered and concentrated to give the crude product which was purified by flash chromatography (silica gel, 0-20% EtOAc in PE) to afford the title compound (87 mg, 40% yield). $^1$H NMR (400 MHz, DMSO) δ 8.31 (d, J=8.6 Hz, 1H), 7.72 (d, J=4.1 Hz, 1H), 7.40-7.34 (m, 2H), 7.23-7.16 (m, 2H), 7.12-7.07 (m, 2H), 4.24-4.13 (m, 1H), 4.10-3.99 (m, 1H), 3.90-3.80 (m, 1H), 3.04-2.89 (m, 1H), 2.88-2.75 (m, 1H), 1.78-1.60 (m, 3H), 1.26-1.17 (m, 2H), 1.15 (d, J=6.8 Hz, 3H). LCMS (ESI) m/z calcd for $C_{19}H_{21}ClN_2O_3S$: 392.10. Found: 393.20/395.19 (M/M+2)$^+$.

Example 46

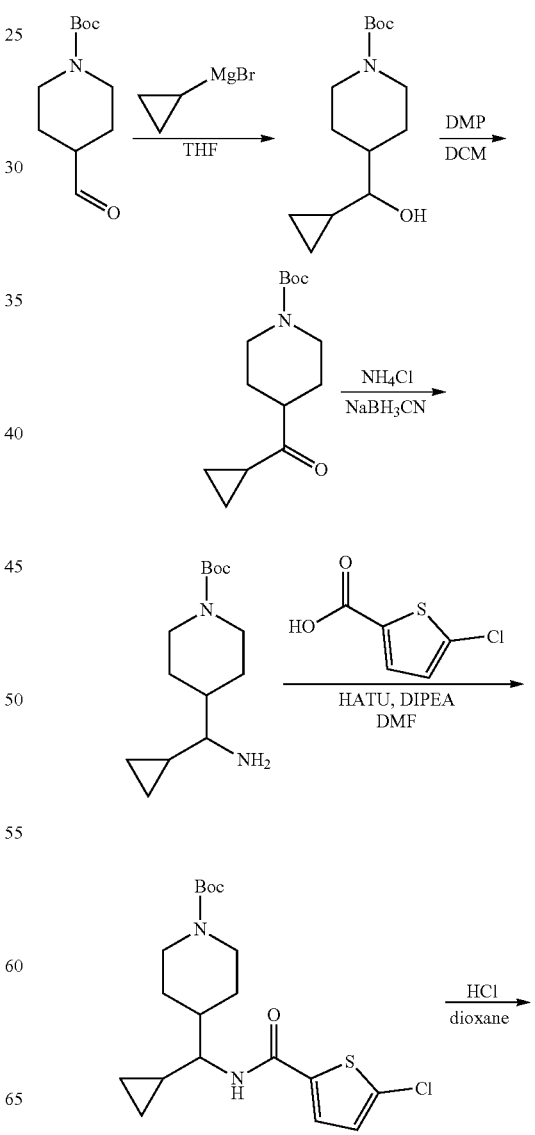

-continued

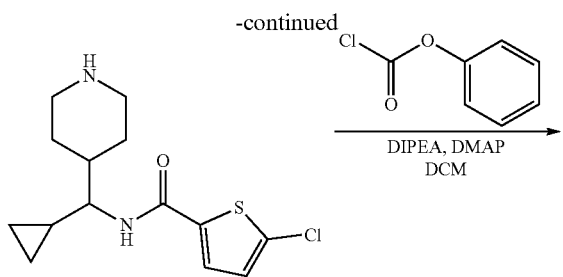

Preparation of Tert-butyl 4-(cyclopropyl(hydroxy)methyl)piperidine-1-carboxylate

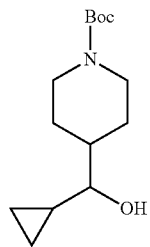 [SMILES: CC(C)(C)OC(=O)N1CCC(C(O)C2CC2)CC1]

At −78° C., to a solution of tert-butyl 4-formylpiperidine-1-carboxylate (2.0 g, 9.38 mmol) in THF (40 mL), was slowly added a solution of cyclopropylmagnesium bromide in THF (11.3 mL, 11.3 mmol). After stirred at r.t. overnight, the reaction was quenched with saturated NH$_4$Cl aq. solution and extracted with EtOAc. The organic layer was washed with brine, dried over Na$_2$SO$_4$, filtered and concentrated to give the crude product which was purified by flash chromatography (silica gel, 0-30% EtOAc in PE) to afford the title compound (1.2 g, 50% yield). LCMS (ESI) m/z calcd for C$_{14}$H$_{25}$NO$_3$: 255.18. Found: 256.46 (M+1)$^+$.

Preparation of Tert-butyl 4-(cyclopropanecarbonyl)piperidine-1-carboxylate

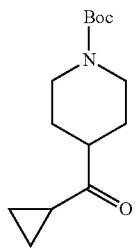 [SMILES: CC(C)(C)OC(=O)N1CCC(C(=O)C2CC2)CC1]

To a solution of tert-butyl 4-(cyclopropyl(hydroxy)methyl)piperidine-1-carboxylate (1.2 g, 4.71 mmol) in DCM (15 mL), was slowly added DMP (2.20 g, 5.18 mmol) in portion wise. After stirred at r.t. for 2 h, the reaction was quenched with saturated NH$_4$Cl aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (1.1 g, 92% yield). LCMS (ESI) m/z calcd for C$_{14}$H$_{23}$NO$_3$: 253.17. Found: 254.36 (M+1)$^+$.

Preparation of Tert-butyl 4-(amino(cyclopropyl)methyl)piperidine-1-carboxylate

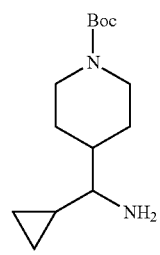 [SMILES: CC(C)(C)OC(=O)N1CCC(C(N)C2CC2)CC1]

To a solution of tert-butyl 4-(cyclopropanecarbonyl)piperidine-1-carboxylate (300 mg, 1.18 mmol) in MeOH (5 mL), was added NH$_4$OAc (1.82 g, 23.6 mmol) and NaBH$_3$CN (742 mg, 11.8 mmol) successively. After stirred at r.t. overnight, the reaction was quenched with saturated NH$_4$Cl aq. solution and extracted with EtOAc. The organic layer was washed with brine, dried over Na$_2$SO$_4$, filtered and concentrated to give the crude product, which was purified by flash chromatography (silica gel, 0-20% EtOAc in PE) to afford the title compound (265 mg, 88% yield). LCMS (ESI) m/z calcd for C$_{14}$H$_{26}$N$_2$O$_2$: 254.20. Found: 255.47 (M+1)$^+$.

Preparation of Tert-butyl 4-((5-chlorothiophene-2-carboxamido)(cyclopropyl) Methyl)piperidine-1-carboxylate

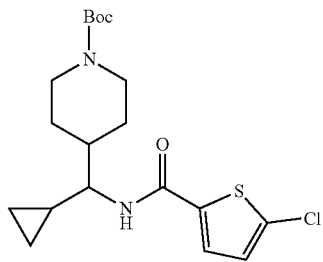 [SMILES: CC(C)(C)OC(=O)N1CCC(C(NC(=O)c2ccc(Cl)s2)C2CC2)CC1]

To a solution of tert-butyl 4-(amino(cyclopropyl)methyl)piperidine-1-carboxylate (130 mg, 0.51 mmol) in DMF (3 mL), was added 5-chlorothiophene-2-carboxylic acid (83 mg, 0.51 mmol), DIPEA (0.40 mL, 2.55 mmol) and HATU (213 mg, 0.56 mmol) successively. After stirred at r.t. for 3 h, the reaction was diluted with water and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (140 mg, 69% yield). LCMS (ESI) m/z calcd for $C_{19}H_{27}ClN_2O_3S$: 398.14. Found: 399.20/401.19 (M/M+2)$^+$.

Preparation of 5-chloro-N-(cyclopropyl(piperidin-4-yl)methyl)thiophene-2-carboxamide

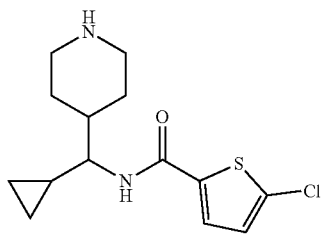 [SMILES: O=C(NC(C1CCNCC1)C1CC1)c1ccc(Cl)s1]

To a solution of tert-butyl 4-((5-chlorothiophene-2-carboxamido)(cyclopropyl) methyl)piperidine-1-carboxylate (140 mg, 0.35 mmol) in DCM (2 mL), was added 4 M HCl in dioxane (3 mL) dropwise. After stirred at r.t. for 2 h, the reaction mixture was concentrated to to afford the title compound (118 mg, 100% yield), which was used in the following step without purification. LCMS (ESI) m/z calcd for $C_{14}H_{19}ClN_2OS$: 298.09. Found: 299.20/301.17 (M/M+2)$^+$.

Preparation of Phenyl 4-((5-chlorothiophene-2-carboxamido)(cyclopropyl) Methyl)piperidine-1-carboxylate

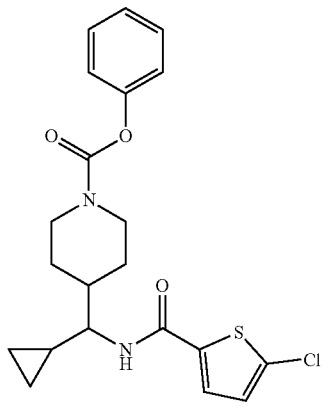 [SMILES: O=C(NC(C1CC1)C1CCN(C(=O)Oc2ccccc2)CC1)c1ccc(Cl)s1]

At 0° C., to a solution of 5-chloro-N-(cyclopropyl(piperidin-4-yl)methyl)thiophene-2-carboxamide (118 mg, 0.35 mmol), DIPEA (0.20 mL, 1.22 mmol) and DMAP (2.6 mg, 0.021 mmol) in DCM (2 mL), was added phenyl carbonochloridate (64 mg, 0.45 mmol) drop wise. After stirred at r.t. for 2 h, the reaction was quenched with saturated NaHCO$_3$ aq. solution and extracted with EtOAc. The organic layer was washed with brine, dried over Na$_2$SO$_4$, filtered and concentrated to give the crude product which was purified by flash chromatography (silica gel, 0-20% EtOAc in PE) to afford the title compound (52 mg, 35% yield). $^1$H NMR (400 MHz, DMSO) δ 8.42 (d, J=8.9 Hz, 1H), 7.74 (d, J=4.1 Hz, 1H), 7.42-7.32 (m, 2H), 7.25-7.16 (m, 2H), 7.13-7.05 (m, 2H), 4.26-4.13 (m, 1H), 4.11-3.95 (m, 1H), 3.21-3.09 (m, 1H), 3.06-2.91 (m, 1H), 2.88-2.72 (m, 1H), 1.98-1.72 (m, 3H), 1.41-1.14 (m, 2H), 1.06-0.94 (m, 1H), 0.66-0.54 (m, 1H), 0.43-0.29 (m, 2H), 0.22-0.13 (m, 1H). LCMS (ESI) m/z calcd for $C_{21}H_{23}ClN_2O_3S$: 418.11. Found: 419.15/421.19 (M/M+2)$^+$.

Example 27

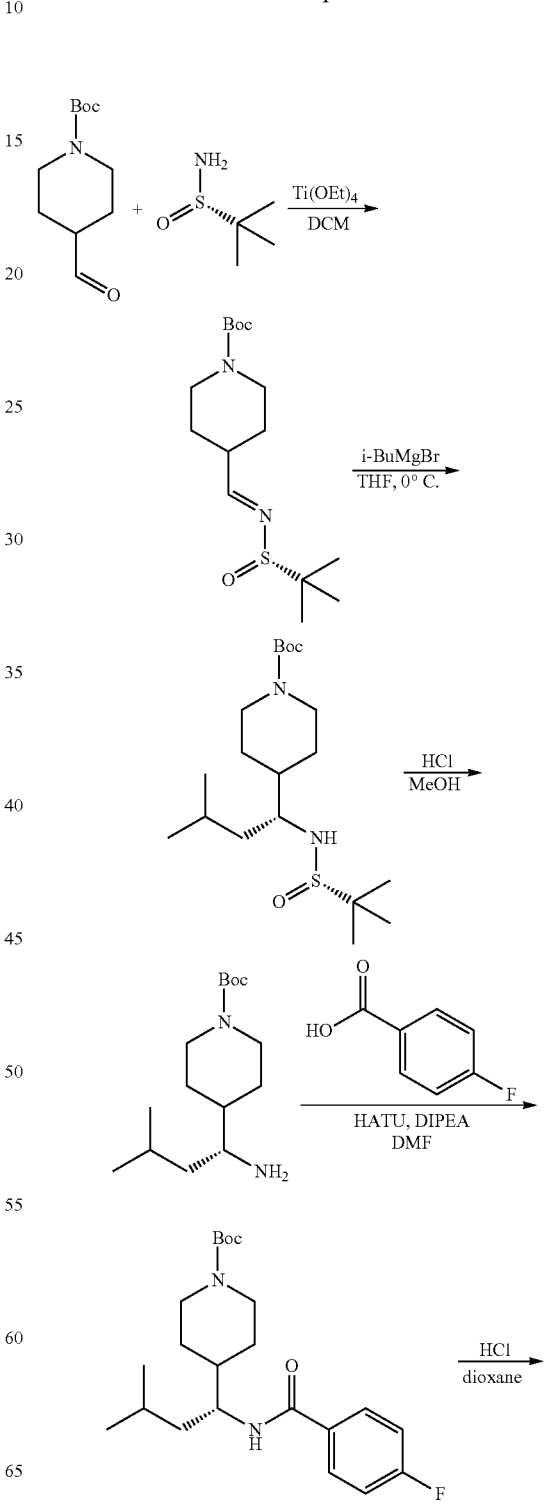

Preparation of Tert-butyl 4-((R)-1-(((S)-tert-butylsulfinyl)amino)-3-methylbutyl) Piperidine-1-carboxylate

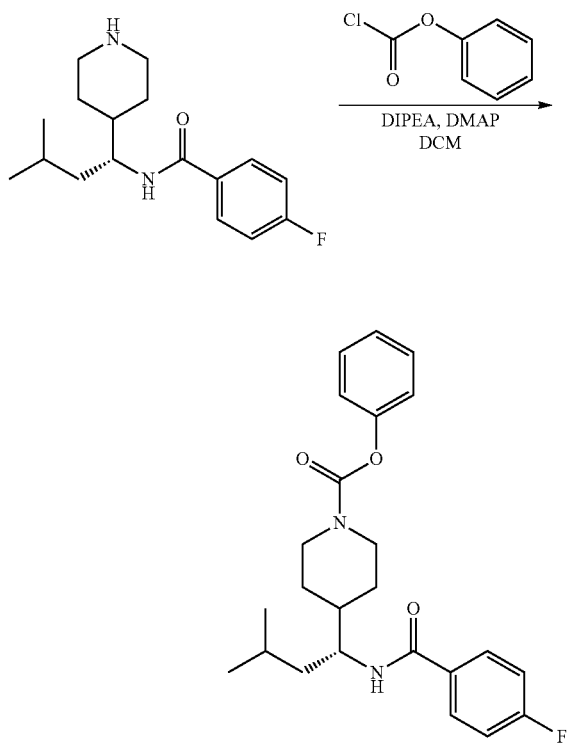

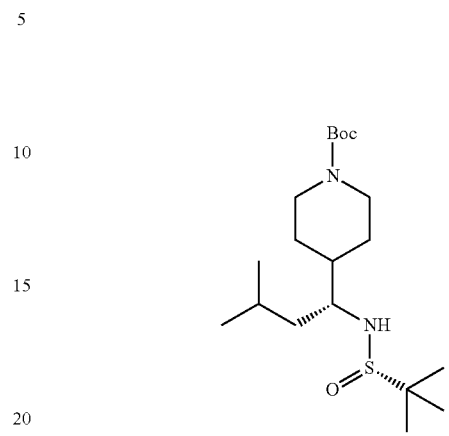

Preparation of Tert-butyl (S,E)-4-(((tert-butylsulfinyl)imino)methyl)piperidine-1-carboxylate A solution of tert-butyl 4-formylpiperidine-1-carboxylate (4.0 g, 18.8 mmol), (S)-2-methylpropane-2-sulfinamide (3.4 g, 28.1 mmol) and titanium tetraethoxide (8.6 g, 37.5 mmol) in DCM (40 ml) was stirred overnight before brine (20 ml) was added. The suspension was filtered through celite and the filtrate extracted with DCM. The organic layer was washed with brine, dried over $Na_2SO_4$, filtered and concentrated to give the crude product which was purified by flash chromatography (silica gel, 0-30% EtOAc in PE) to afford the title compound (5.1 g, 86% yield). LCMS (ESI) m/z calcd for $C_{15}H_{28}N_2O_3S$: 316.18. Found: 317.28 (M+1)$^+$.

At 0° C., to a solution of (S,E)-tert-butyl 4-{{tertbutylsulfinyiimino) methyl)piperidine-1-carboxylate (2.6 g, 8.2 mmol) in THF (60 mL) under nitrogen atmosphere, was added $^{t}$BuMgBr (21 ml, 41.0 mmol) (2M in THF) drop wise and the reaction stirred for 2 h at this temperature. The reaction was carefully quenched via the addition of saturated aqueous $NH_4Cl$. The solid were broken up by the addition of 1N HCl. The layers were separated and the aqueous phase was extracted with DCM. The combined organic layer was washed with brine, dried over $Na_2SO_4$, filtered and concentrated to give the crude product which was purified by flash chromatography (silica gel, 0-30% EtOAc in PE) to afford the title compound (2.6 g, 84% yield). LCMS (ESI) m/z calcd for $C_{19}H_{38}N_2O_3S$: 374.26. Found: 375.67 (M+1)$^+$.

Preparation of Tert-butyl (R)-4-(1-amino-3-methylbutyl)piperidine-1-carboxylate

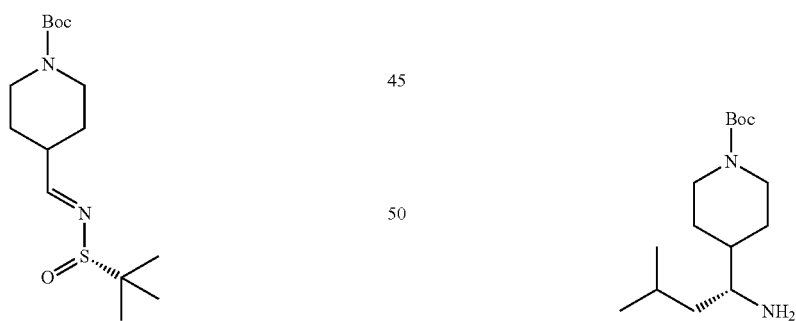

To tert-butyl 4-((R)-1-(((S)-tert-butylsulfinyl)amino)-3-methylbutyl)piperidine-1-carboxylate (2.0 g, 5.34 mmol) was added 0.4 M HCl in MeOH (14.7 mL, 5.87 mmol). After stirred at r.t. for 1 h, LCMS showed the reaction was complete. The reaction mixture was quenched with saturated aq. $NaHCO_3$ and extracted with DCM (×3). The combined organic layers were washed with brine and dried over $Na_2SO_4$. Solvent was removed under vacuum to afford the title compound (983 mg, 68%) as a viscous pale oil, which was used in the following step directly. LCMS (ESI) m/z calcd for $C_{15}H_{30}N_2O_2$: 270.23. Found: 271.34 (M+1)$^+$.

Preparation of Tert-butyl (R)-4-(1-(4-fluorobenzamido)-3-methylbutyl)piperidine-1-carboxylate

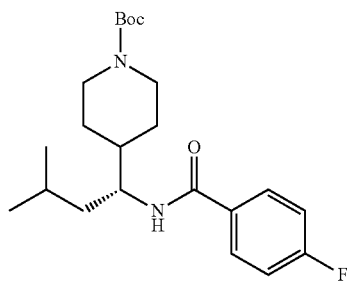 [SMILES: CC(C)C[C@@H](NC(=O)c1ccc(F)cc1)C1CCN(C(=O)OC(C)(C)C)CC1]

To a stirred solution of tert-butyl (R)-4-(1-amino-3-methylbutyl)piperidine-1-carboxylate (300 mg, 1.11 mmol) and 4-fluorobenzoic acid (155 mg, 1.11 mmol) in DMF (5 mL) under was added DIPEA (0.40 mL, 2.22 mmol) followed by HATU (506 mg, 1.33 mmol). After stirred at r.t. overnight, the reaction mixture was quenched with brine and the resulting mixture was extracted with DCM (×3). The combined organic layers were dried over $Na_2SO_4$. Solvent was removed under vacuum and the residue was purified by flash chromatography (silica gel, 0~70% ethyl acetate in petroleum ether) to afford the title compound (410 mg, 94%) as a pale solid. LCMS (ESI) m/z calcd for $C_{22}H_{33}FN_2O_3$: 392.25. Found: 393.64 (M+1)+.

Preparation of (R)-4-fluoro-N-(3-methyl-1-(piperidin-4-yl)butyl)benzamide

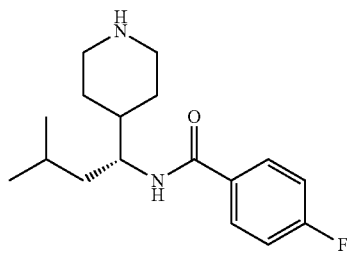 [SMILES: CC(C)C[C@@H](NC(=O)c1ccc(F)cc1)C1CCNCC1]

To a solution of tert-butyl (R)-4-(1-(4-fluorobenzamido)-3-methylbutyl)piperidine-1-carboxylate (410 mg, 1.04 mmol) in DCM (4.0 mL) was added 4 M HCl in dioxane (10 mL). After stirred at r.t. for 1 h, the reaction mixture was concentrated under vacuum to afford the title compound (280 mg, 92%) as a HCl salt, which was used in the following step directly. LCMS (ESI) m/z calcd for $C_{17}H_{25}FN_2O$: 292.20. Found: 293.32 (M+1)+.

Preparation of Phenyl (R)-4-(1-(4-fluorobenzamido)-3-methylbutyl)piperidine-1-carboxylate

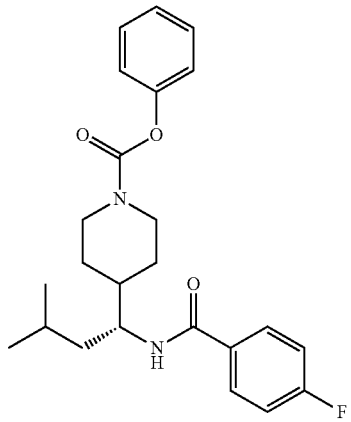

At 0° C., to a stirred solution of (R)-4-fluoro-N-(3-methyl-1-(piperidin-4-yl)butyl)benzamide (290 mg, 0.88 mmol) and DMAP (6.0 mg, 0.044 mmol) in DCM (5 mL) was added DIPEA (0.6 mL, 3.53 mmol) followed by phenyl carbonochloridate (207 mg, 1.32 mmol) drop wise. After stirred at r.t. for 2 h, the reaction mixture was partitioned between $DCM/H_2O$, and the layers were separated. The organic layer was washed with aq. $NaHCO_3$, brine and dried over $Na_2SO_4$. Solvent was removed under vacuum and the residue was purified by Gilson (C18, 10-70% MeCN in water with 0.1% formic acid) to afford the title compound (204 mg, 50%) as a white solid. $^1$H NMR (400 MHz, DMSO) δ 8.09 (d, J=9.0 Hz, 1H), 7.97-7.89 (m, 2H), 7.40-7.33 (m, 2H), 7.33-7.25 (m, 2H), 7.23-7.17 (m, 1H), 7.09 (d, J=7.6 Hz, 2H), 4.23-4.11 (m, 1H), 4.09-3.94 (m, 2H), 3.00-2.75 (m, 2H), 1.79-1.52 (m, 5H), 1.35-1.17 (m, 3H), 0.93-0.81 (m, 6H). LCMS (ESI) m/z calcd for $C_{24}H_{29}FN_2O_3$: 412.22. Found: 413.28 (M+1)+.

The following compounds were synthesized following the procedure described for examples 27 and 40 using appropriate materials.

Example 104

(R)-2-methylpyridin-3-yl 4-(1-(4-chlorobenzamido)-3-methylbutyl)piperidine-1-carboxylate

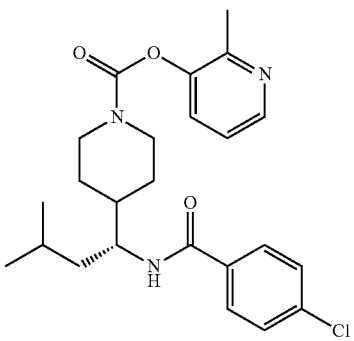 [SMILES: Cc1ncccc1OC(=O)N1CCC([C@@H](CC(C)C)NC(=O)c2ccc(Cl)cc2)CC1]

$^1$H NMR (400 MHz, METHANOL-d$_4$) δ ppm 8.26 (d, J=4.3 Hz, 1H) 7.79 (d, J=8.4 Hz, 2H) 7.44-7.55 (m, 3H)

7.25-7.33 (m, 1H) 4.30-4.44 (m, 1H) 4.03-4.23 (m, 2H) 2.96-3.16 (m, 1H) 2.76-2.96 (m, 1H) 2.38 (br. s., 3H) 1.68-1.92 (m, 3H) 1.51-1.68 (m, 2H) 1.22-1.47 (m, 3H) 0.93 (t, J=6.9 Hz, 6H) LCMS (ESI) m/z calcd for C24H30ClN3O3: 443.97 Found: 444.28 (M+1)+.

Example 105

(R)-2-methoxypyridin-3-yl 4-(1-(4-chlorobenzamido)-3-methylbutyl)piperidine-1-carboxylate

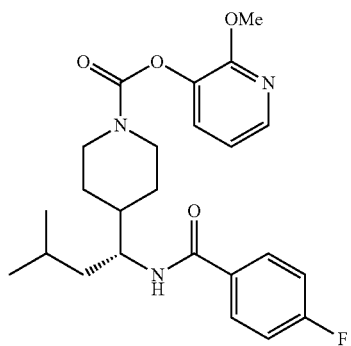 [SMILES: COc1ncccc1OC(=O)N1CCC([C@@H](CC(C)C)NC(=O)c2ccc(F)cc2)CC1]

$^1$H NMR (400 MHz, METHANOL-d$_4$) δ ppm 7.95 (d, J=4.7 Hz, 1H) 7.87 (dd, J=8.0, 5.7 Hz, 2H) 7.40 (d, J=7.6 Hz, 1H) 7.18 (t, J=8.6 Hz, 2H) 6.94 (dd, J=7.3, 5.4 Hz, 1H) 4.24-4.38 (m, 1H) 4.04-4.20 (m, 2H) 3.86 (d, J=15.8 Hz, 3H) 2.93-3.09 (m, 1H) 2.76-2.93 (m, 1H) 1.68-1.90 (m, 3H) 1.54-1.68 (m, 2H) 1.22-1.48 (m, 3H) 0.88-1.02 (m, 6H)

LCMS (ESI) m/z calcd for C24H30FN3O: 443.51 Found: 444.28 (M+1)+.

Example 106

(R)-3-fluoro-2-methoxyphenyl 4-(1-(4-fluorobenzamido)-3-methylbutyl)piperidine-1-carboxylate

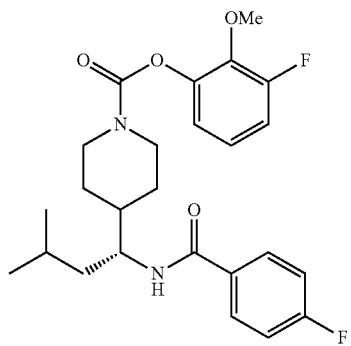 [SMILES: COc1c(F)cccc1OC(=O)N1CCC([C@@H](CC(C)C)NC(=O)c2ccc(F)cc2)CC1]

$^1$H NMR (400 MHz, METHANOL-d$_4$) δ ppm 7.86 (dd, J=8.4, 5.5 Hz, 2H) 7.19 (t, J=8.7 Hz, 2H) 6.94-7.07 (m, 2H) 6.88 (d, J=4.9 Hz, 1H) 4.24-4.41 (m, 1H) 3.97-4.23 (m, 2H) 3.81 (d, J=9.4 Hz, 3H) 2.94-3.13 (m, 1H) 2.72-2.93 (m, 1H) 1.71-1.94 (m, 3H) 1.53-1.70 (m, 2H) 1.21-1.50 (m, 3H) 0.94 (d, J=13.3 Hz, 6H)

LCMS (ESI) m/z calcd for C25H30F2N2O4: 460.51 Found: 461.29 (M+1)+.

Example 107

(R)-4,6-dimethylpyrimidin-5-yl 4-(1-(4-chlorobenzamido)-3-methylbutyl)piperidine-1-carboxylate

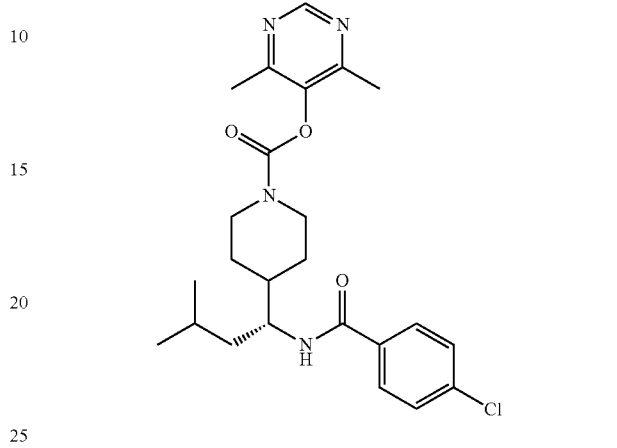

$^1$H NMR (400 MHz, METHANOL-d$_4$) δ ppm 8.70 (s, 1H) 7.79 (d, J=8.6 Hz, 2H) 7.48 (d, J=8.6 Hz, 2H) 4.28-4.47 (m, 1H) 4.00-4.24 (m, 2H) 3.02-3.19 (m, 1H) 2.84-3.01 (m, 1H) 2.36 (s, 3H) 2.33 (s, 3H) 1.71-1.95 (m, 3H) 1.54-1.70 (m, 2H) 1.26-1.48 (m, 3H) 0.84-1.04 (m, 6H).

LCMS (ESI) m/z calcd for C24H31ClN4O3: 458.98 Found: 459.32 (M+1)+.

Example 8

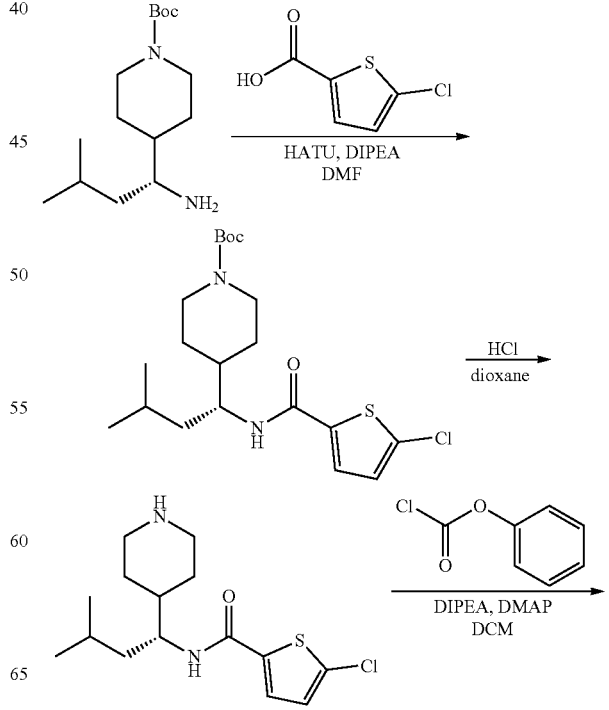

-continued

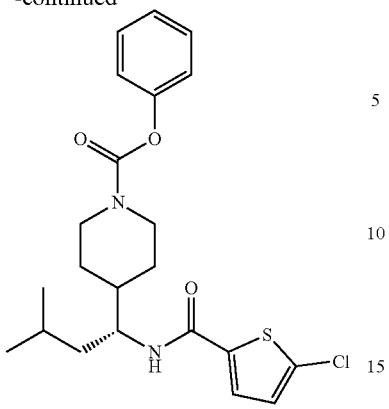

Preparation of Tert-butyl (R)-4-(1-(5-chlorothiophene-2-carboxamido)-3-methylbutyl)piperidine-1-carboxylate

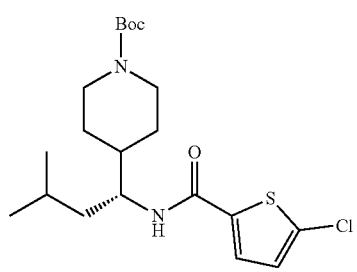 [SMILES: CC(C)C[C@@H](NC(=O)c1ccc(Cl)s1)C1CCN(C(=O)OC(C)(C)C)CC1]

To a stirred solution of tert-butyl (R)-4-(1-amino-3-methylbutyl)piperidine-1-carboxylate (300 mg, 1.11 mmol) and 5-chlorothiophene-2-carboxylic acid (198 mg, 1.22 mmol) in DMF (5 mL) under was added DIPEA (300 mg, 2.22 mmol) followed by HATU (630 mg, 1.66 mmol). After stirred at r.t. overnight, the reaction mixture was quenched with brine and the resulting mixture was extracted with DCM (×3). The combined organic layers were dried over Na$_2$SO$_4$. Solvent was removed under vacuum and the residue was purified by flash chromatography (silica gel, 0~70% ethyl acetate in petroleum ether) to afford the title compound (410 mg, 89%)) as a pale solid. LCMS (ESI) m/z calcd for C$_{20}$H$_{31}$ClN$_2$O$_3$S: 414.17. Found: 415.25/417.26 (M/M+2)$^+$.

Preparation of (R)-5-chloro-N-(3-methyl-1-(piperidin-4-yl)butyl)thiophene-2-carboxamide

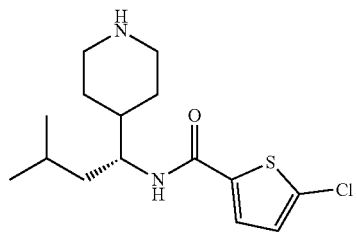 [SMILES: CC(C)C[C@@H](NC(=O)c1ccc(Cl)s1)C1CCNCC1]

To a solution of tert-butyl (R)-4-(1-(5-chlorothiophene-2-carboxamido)-3-methylbutyl)piperidine-1-carboxylate (300 mg, 0.72 mmol) in DCM (3.0 mL) was added 4 M HCl in dioxane (10 mL). After stirred at r.t. for 1 h, the reaction mixture was concentrated under vacuum to afford the title compound (253 mg, 100% yield) as a HCl salt, which was used in the following step directly. LCMS (ESI) m/z calcd for C$_{15}$H$_{23}$ClN$_2$OS: 314.12. Found: 315.25/317.22 (M/M+2)$^+$.

Preparation of Phenyl (R)-4-(1-(5-chlorothiophene-2-carboxamido)-3-methylbutyl) Piperidine-1-carboxylate

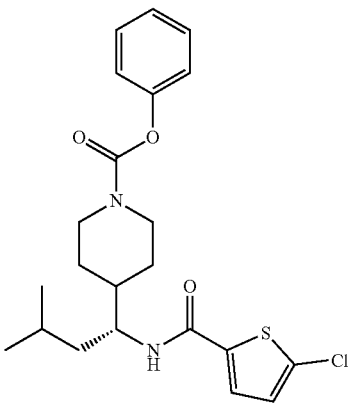 [SMILES: CC(C)C[C@@H](NC(=O)c1ccc(Cl)s1)C1CCN(C(=O)Oc2ccccc2)CC1]

At 0° C., to a stirred solution of (R)-5-chloro-N-(3-methyl-1-(piperidin-4-yl)butyl)thiophene-2-carboxamide (200 mg, 0.57 mmol) and DMAP (3 mg, 0.029 mmol) in DCM (5 mL) was added DIPEA (294 mg, 2.28 mmol) followed by phenyl carbonochloridate (134 mg, 0.85 mmol) drop wise. After stirred at r.t. for 2 h, the reaction mixture was partitioned between DCM/H$_2$O, and the layers were separated. The organic layer was washed with aq. NaHCO$_3$, brine and dried over Na$_2$SO$_4$. Solvent was removed under vacuum and the residue was purified by Gilson (C18, 10-70% MeCN in water with 0.1% formic acid) to afford the title compound (171 mg, 63%) as a white solid. $^1$H NMR (400 MHz, DMSO) δ 8.17 (d, J=9.1 Hz, 1H), 7.73 (d, J=4.1 Hz, 1H), 7.41-7.31 (m, 2H), 7.24-7.15 (m, 2H), 7.09 (d, 2H), 4.23-4.11 (m, 1H), 4.10-3.98 (m, 1H), 3.95-3.84 (m, 1H), 2.99-2.74 (m, 2H), 1.79-1.48 (m, 5H), 1.36-1.15 (m, 3H), 0.94-0.80 (m, 6H). LCMS (ESI) m/z calcd for C$_{22}$H$_{27}$ClN$_2$O$_3$S: 434.14. Found: 435.23/437.21 (M+1)$^+$.
The following compound was synthesized following the procedure described for examples 8 using appropriate materials.

Example 109

(R)-phenyl 4-(1-(1H-indazole-7-carboxamido)-3-methylbutyl)piperidine-1-carboxylate

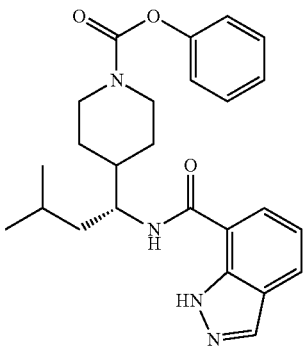 [SMILES: CC(C)C[C@@H](NC(=O)c1cccc2cn[nH]c12)C1CCN(C(=O)Oc2ccccc2)CC1]

¹H NMR (400 MHz, METHANOL-d₄) δ ppm 8.11 (s, 1H) 7.96 (d, J=8.0 Hz, 1H) 7.89 (d, J=7.2 Hz, 1H) 7.29-7.38 (m, 2H) 7.12-7.29 (m, 2H) 6.99-7.09 (m, 2H) 4.28-4.40 (m, 1H) 4.10-4.26 (m, 2H) 2.92-3.09 (m, 1H) 2.74-2.92 (m, 1H) 1.80-1.97 (m, 2H) 1.55-1.80 (m, 3H) 1.26-1.53 (m, 3H) 0.96 (d, J=6.2 Hz, 6H).

LCMS (ESI) m/z calcd for C₂₅H₃₀N₄O₃: 434.23. Found: 435.36 (M+1)⁺.

Example 21

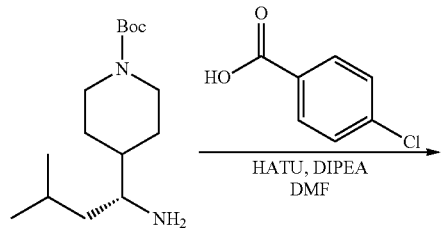

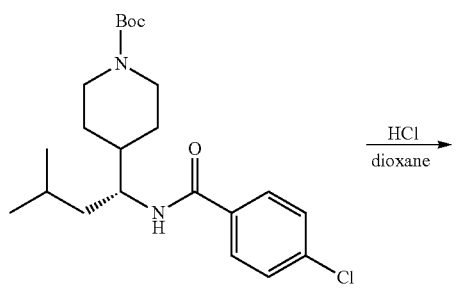

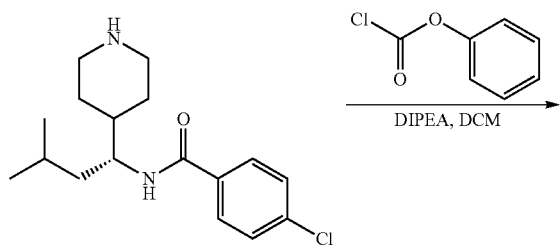

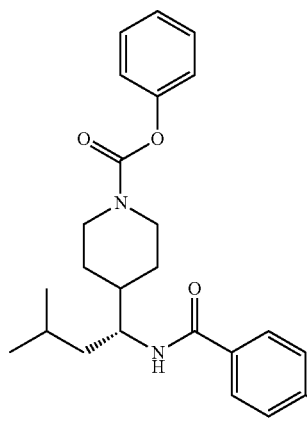

Preparation of Tert-butyl (R)-4-(1-(4-chlorobenzamido)-3-methylbutyl)piperidine-1-carboxylate

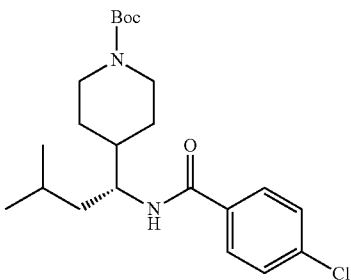 [SMILES: CC(C)C[C@@H](NC(=O)c1ccc(Cl)cc1)C1CCN(C(=O)OC(C)(C)C)CC1]

To a stirred solution of tert-butyl (R)-4-(1-amino-3-methylbutyl)piperidine-1-carboxylate (180 mg, 0.67 mmol) and 4-chlorobenzoic acid (104 mg, 0.67 mmol) in DMF (3 mL) was added DIPEA (0.30 mL, 1.33 mmol) followed by HATU (380 mg, 0.998 mmol). After stirred at r.t. overnight, the reaction mixture was quenched with brine and the resulting mixture was extracted with DCM (×3). The combined organic layers were dried over Na₂SO₄. Solvent was removed under vacuum and the residue was purified by flash chromatography (silica gel, 0~70% ethyl acetate in petroleum ether) to afford the title compound (240 mg, 87%) as a pale solid. LCMS (ESI) m/z calcd for C₂₂H₃₃ClN₂O₃: 408.22. Found: 409.62/411.62 (M/M+2)⁺.

Preparation of (R)-4-chloro-N-(3-methyl-1-(piperidin-4-yl)butyl)benzamide

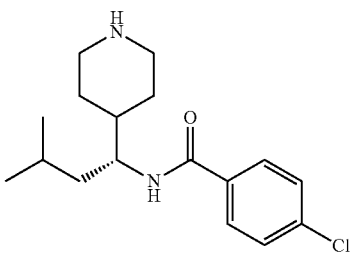 [SMILES: CC(C)C[C@@H](NC(=O)c1ccc(Cl)cc1)C1CCNCC1]

To a solution of tert-butyl (R)-4-(1-(4-chlorobenzamido)-3-methylbutyl)piperidine-1-carboxylate (240 mg, 0.59 mmol) in DCM (2.0 mL) was added 4 M HCl in dioxane (3 mL). After stirred at r.t. for 1 h, the reaction mixture was concentrated under vacuum to afford the title compound (190 mg, quantitative yield) as a HCl salt, which was used in the following step directly. LCMS (ESI) m/z calcd for C₁₇H₂₅ClN₂O: 308.17. Found: 309.67/311.31 (M/M+2)⁺.

Preparation of Phenyl (R)-4-(1-(4-chlorobenzamido)-3-methylbutyl)piperidine-1-carboxylate

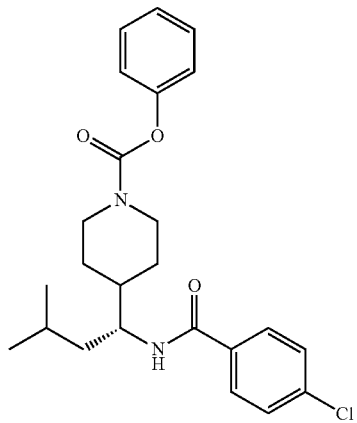 [SMILES: CC(C)C[C@@H](NC(=O)c1ccc(Cl)cc1)C1CCN(C(=O)Oc2ccccc2)CC1]

At 0° C., to a stirred solution of (R)-4-chloro-N-(3-methyl-1-(piperidin-4-yl)butyl)benzamide (130 mg, 0.38 mmol) and DMAP (6.0 mg, 0.05 mmol) in DCM (5 mL) was added DIPEA (0.3 mL, 1.51 mmol) followed by phenyl carbonochloridate (89 mg, 0.565 mmol) drop wise. After stirred at r.t. for 2 h, the reaction mixture was partitioned between DCM/H$_2$O, and the layers were separated. The organic layer was washed with aq. NaHCO$_3$, brine and dried over Na$_2$SO$_4$. Solvent was removed under vacuum and the residue was purified by Gilson (C18, 10-70% MeCN in water with 0.1% formic acid) to afford the title compound (111 mg, 69%) as a white solid. $^1$H NMR (400 MHz, DMSO) δ 8.15 (d, J=9.1 Hz, 1H), 7.93-7.84 (m, 2H), 7.58-7.51 (m, 2H), 7.41-7.32 (m, 2H), 7.20 (t, J=7.4 Hz, 1H), 7.09 (d, J=7.6 Hz, 2H), 4.24-4.12 (m, 1H), 4.09-3.94 (m, 2H), 3.02-2.88 (m, 1H), 2.87-2.74 (m, 1H), 1.80-1.53 (m, 5H), 1.35-1.17 (m, 3H), 0.93-0.81 (m, 6H). LCMS (ESI) m/z calcd for C$_{24}$H$_{29}$ClN$_2$O$_3$: 428.19. Found: 429.22/431.21 (M/M+2)$^+$.

Example 69

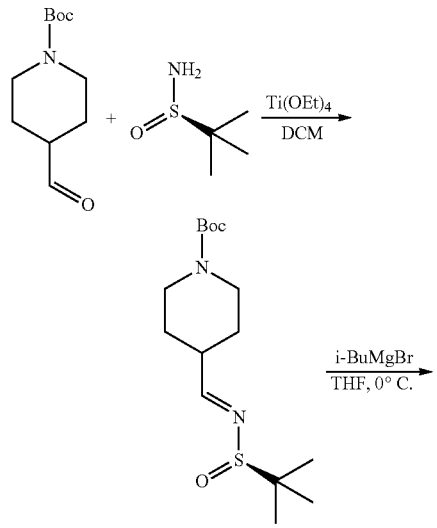

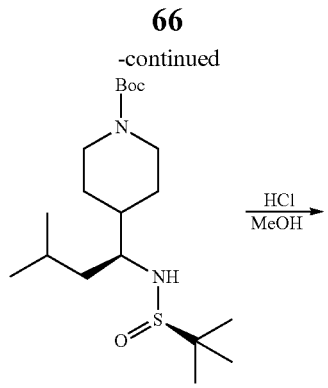

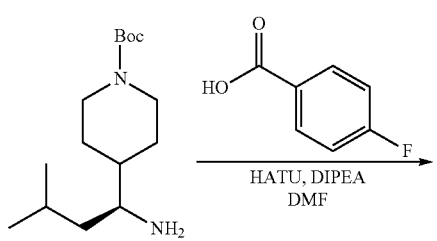

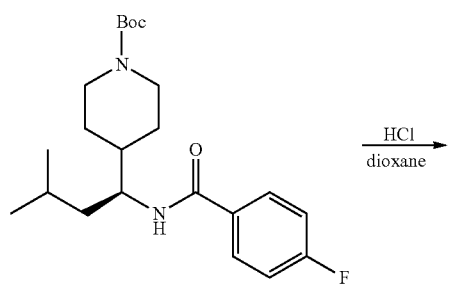

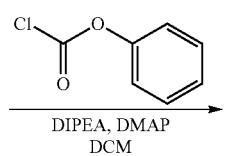

Preparation of Tert-butyl (R,E)-4-(((tert-butylsulfinyl)imino)methyl)piperidine-1-carboxylate

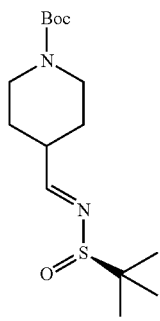 [SMILES: CC(C)(C)OC(=O)N1CCC(/C=N/[S@](=O)C(C)(C)C)CC1]

A solution of tert-butyl 4-formylpiperidine-1-carboxylate (4.0 g, 18.75 mmol), (R)-2-methylpropane-2-sulfinamide (2.73 g, 22.5 mmol) and titanium tetraethoxide (8.6 g, 37.5 mmol) in DCM (40 ml) was stirred overnight before brine (30 ml) was added. The suspension was filtered through celite and the filtrate extracted with DCM. The organic layer was washed with brine, dried over $Na_2SO_4$, filtered and concentrated to give the crude product which was purified by flash chromatography (silica gel, 0-30% EtOAc in PE) to afford the title compound (4.8 g, 81% yield). LCMS (ESI) m/z calcd for $C_{15}H_{28}N_2O_3S$: 316.18. Found: 317.37 $(M+1)^+$.

Preparation of Tert-butyl 4-((S)-1-(((R)-tert-butylsulfinyl)amino)-3-methylbutyl) Piperidine-1-carboxylate

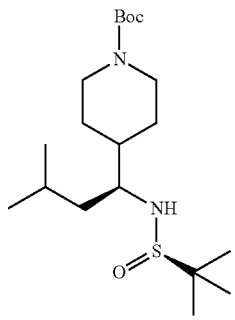 [SMILES: CC(C)C[C@H](N[S@](=O)C(C)(C)C)C1CCN(C(=O)OC(C)(C)C)CC1]

At 0° C., to a solution of (R,E)-4-(((tert-butylsulfinyl)imino)methyl)piperidine-1-carboxylate (2.4 g, 7.59 mmol) in THF (50 mL) under nitrogen atmosphere, was added $^i$BuMgBr (19.0 ml, 38.0 mmol) (2 M in THF) drop wise and the reaction stirred for 2 h at this temperature. The reaction was carefully quenched via the addition of saturated aqueous $NH_4Cl$. The solid were broken up by the addition of 1N HCl. The layers were separated and the aqueous phase was extracted with DCM. The combined organic layer was washed with brine, dried over $Na_2SO_4$, filtered and concentrated to give the crude product which was purified by flash chromatography (silica gel, 0-30% EtOAc in PE) to afford the title compound (1.48 g, 52% yield). LCMS (ESI) m/z calcd for $C_{19}H_{38}N_2O_3S$: 374.26. Found: 375.38 $(M+1)^+$.

Preparation of Tert-butyl (S)-4-(1-amino-3-methylbutyl)piperidine-1-carboxylate

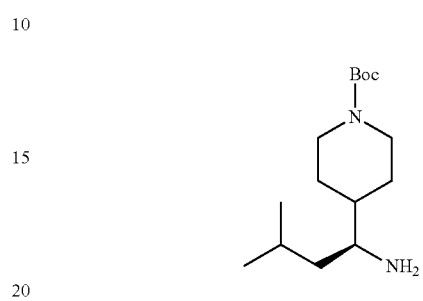

To tert-butyl 4-((S)-1-(((R)-tert-butylsulfinyl)amino)-3-methylbutyl)piperidine-1-carboxylate (1.48 g, 3.95 mmol) was added 0.4 M HCl in MeOH (10.9 mL, 4.35 mmol). After stirred at r.t. for 1 h, LCMS showed the reaction was complete. The reaction mixture was quenched with saturated aq. $NaHCO_3$ and extracted with DCM. The combined organic layers were washed with brine and dried over $Na_2SO_4$. Solvent was removed under vacuum to afford the title compound (612 mg, 57%) as a pale oil, which was used in the following step directly. LCMS (ESI) m/z calcd for $C_{15}H_{30}N_2O_2$: 270.23. Found: 271.29 $(M+1)^+$.

Preparation of Tert-butyl (S)-4-(1-(4-fluorobenzamido)-3-methylbutyl)piperidine-1-carboxylate

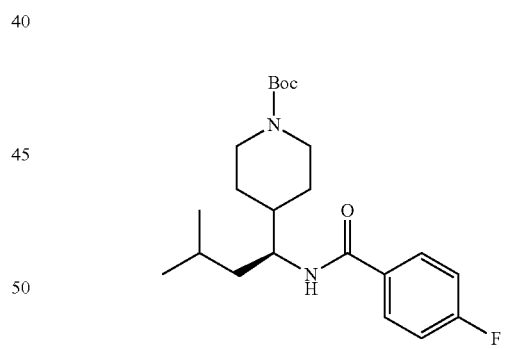

To a stirred solution of tert-butyl (S)-4-(1-amino-3-methylbutyl)piperidine-1-carboxylate (350 mg, 1.30 mmol) and 4-fluorobenzoic acid (210 mg, 1.42 mmol) in DMF (5 mL) under was added DIPEA (350 mg, 2.59 mmol) followed by HATU (772 mg, 1.94 mmol). After stirred at r.t. overnight, the reaction mixture was quenched with brine and the resulting mixture was extracted with DCM (×3). The combined organic layers were dried over $Na_2SO_4$. Solvent was removed under vacuum and the residue was purified by flash chromatography (silica gel, 0~70% ethyl acetate in petroleum ether) to afford the title compound (390 mg, 77%)) as a pale solid. LCMS (ESI) m/z calcd for $C_{22}H_{33}FN_2O_3$: 392.25. Found: 393.35 $(M+1)^+$.

Preparation of (S)-4-fluoro-N-(3-methyl-1-(piperidin-4-yl)butyl)benzamide

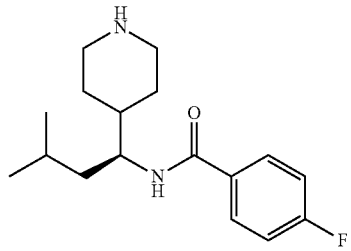 [SMILES: CC(C)C[C@H](NC(=O)c1ccc(F)cc1)C1CCNCC1]

To a solution of tert-butyl (S)-4-(1-(4-fluorobenzamido)-3-methylbutyl)piperidine-1-carboxylate (390 mg, 0.994 mmol) in DCM (2.0 mL) was added 4 M HCl in dioxane (8 mL). After stirred at r.t. for 1 h, the reaction mixture was concentrated under vacuum to afford the title compound (300 mg, quantitative) as a HCl salt, which was used in the following step directly. LCMS (ESI) m/z calcd for $C_{17}H_{25}FN_2O$: 292.20. Found: 293.14 $(M+1)^+$.

Preparation of Phenyl (S)-4-(1-(4-fluorobenzamido)-3-methylbutyl)piperidine-1-carboxylate

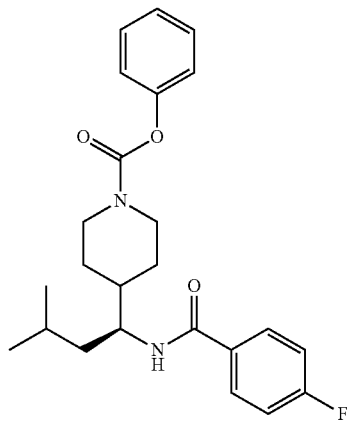 [SMILES: CC(C)C[C@H](NC(=O)c1ccc(F)cc1)C1CCN(C(=O)Oc2ccccc2)CC1]

At 0° C., to a stirred solution of (S)-4-fluoro-N-(3-methyl-1-(piperidin-4-yl)butyl)benzamide (290 mg, 0.88 mmol) and DMAP (6 mg, 0.044 mmol) in DCM (5 mL) was added DIPEA (0.6 mL, 3.53 mmol) followed by phenyl carbonochloridate (207 mg, 1.32 mmol) drop wise. After stirred at r.t. for 2 h, the reaction mixture was partitioned between DCM/H$_2$O, and the layers were separated. The organic layer was washed with aq. NaHCO$_3$, brine and dried over Na$_2$SO$_4$. Solvent was removed under vacuum and the residue was purified by Gilson (C18, 10-50% MeCN in water with 0.1% formic acid) to afford the title compound (91 mg, 54%) as a white solid. $^1$H NMR (400 MHz, DMSO) δ 8.09 (d, J=9.1 Hz, 1H), 7.98-7.89 (m, 2H), 7.40-7.33 (m, 2H), 7.32-7.25 (m, 2H), 7.23-7.16 (m, 1H), 7.09 (d, J=7.7 Hz, 2H), 4.24-4.12 (m, 1H), 4.08-3.92 (m, 2H), 3.00-2.74 (m, 2H), 1.79-1.52 (m, 5H), 1.34-1.16 (m, 3H), 0.93-0.82 (m, 6H). LCMS (ESI) m/z calcd for $C_{24}H_{29}FN_2O_3$: 412.22. Found: 413.31 $(M+1)^+$.

Example 58

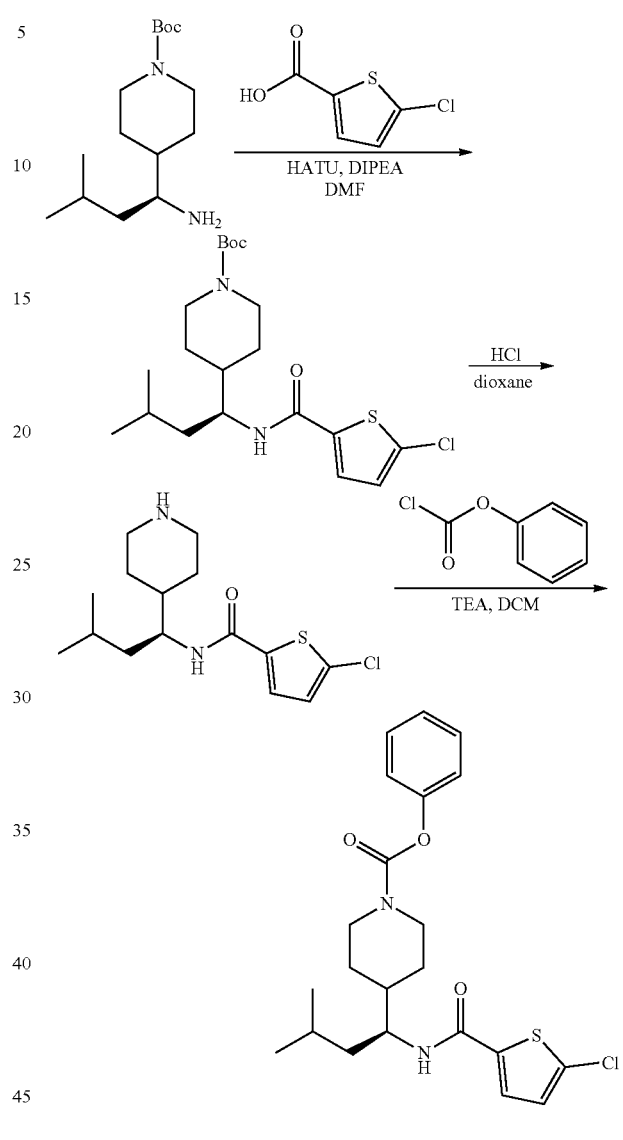

Preparation of Tert-butyl (S)-4-(1-(5-chlorothiophene-2-carboxamido)-3-methylbutyl)piperidine-1-carboxylate

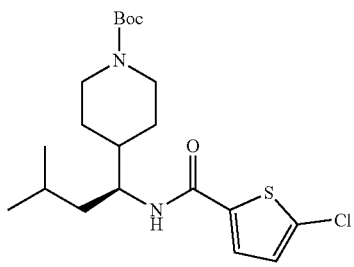 [SMILES: CC(C)C[C@H](NC(=O)c1ccc(Cl)s1)C1CCN(C(=O)OC(C)(C)C)CC1]

To a stirred solution of tert-butyl (S)-4-(1-amino-3-methylbutyl)piperidine-1-carboxylate (200 mg, 0.74 mmol) and 5-chlorothiophene-2-carboxylic acid (132 mg, 0.81 mmol) in DMF (5 mL) under was added DIPEA (382 mg, 2.96 mmol) followed by HATU (630 mg, 1.66 mmol). After stirred at r.t. overnight, the reaction mixture was quenched with brine and the resulting mixture was extracted with DCM (×3). The combined organic layers were dried over $Na_2SO_4$. Solvent was removed under vacuum and the residue was purified by flash chromatography (silica gel, 0~70% ethyl acetate in petroleum ether) to afford the title compound (280 mg, 91%) as a pale solid. LCMS (ESI) m/z calcd for $C_{20}H_{31}ClN_2O_3S$: 414.17. Found: 415.23/417.22 (M/M+2)$^+$.

Preparation of (S)-5-chloro-N-(3-methyl-1-(piperidin-4-yl)butyl)thiophene-2-carboxamide

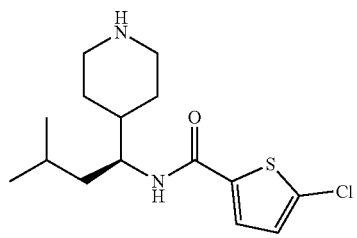 [SMILES: CC(C)C[C@H](NC(=O)c1ccc(Cl)s1)C1CCNCC1]

To a solution of tert-butyl (S)-4-(1-(5-chlorothiophene-2-carboxamido)-3-methylbutyl)piperidine-1-carboxylate (280 mg, 0.676 mmol) in DCM (2.0 mL) was added 4 M HCl in dioxane (5.0 mL). After stirred at r.t. for 1 h, the reaction mixture was concentrated under vacuum to afford the title compound (200 mg, 94%) as a HCl salt, which was used in the following step directly. LCMS (ESI) m/z calcd for $C_{15}H_{23}ClN_2OS$: 314.12. Found: 315.23/317.21 (M/M+2)$^+$.

Preparation of Phenyl (S)-4-(1-(5-chlorothiophene-2-carboxamido)-3-ethylbutyl) Piperidine-1-carboxylate

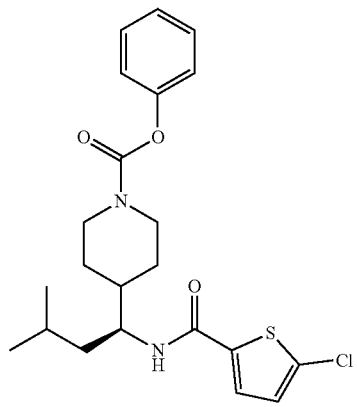 [SMILES: CC(C)C[C@H](NC(=O)c1ccc(Cl)s1)C1CCN(C(=O)Oc2ccccc2)CC1]

At 0° C., to a stirred solution of (S)-5-chloro-N-(3-methyl-1-(piperidin-4-yl)butyl)thiophene-2-carboxamide (200 mg, 0.569 mmol) and DMAP (3 mg, 0.029 mmol) in DCM (3 mL) was added DIPEA (294 mg, 2.77 mmol) followed by phenyl carbonochloridate (134 mg, 0.85 mmol) drop wise. After stirred at r.t. for 2 h, the reaction mixture was partitioned between DCM/$H_2O$, and the layers were separated. The organic layer was washed with aq. $NaHCO_3$, brine and dried over $Na_2SO_4$. Solvent was removed under vacuum and the residue was purified by Gilson (C18, 10-60% MeCN in water with 0.1% formic acid) to afford the title compound (182 mg, 66%) as a white solid. $^1$H NMR (400 MHz, DMSO) δ 8.16 (d, J=9.1 Hz, 1H), 7.73 (d, J=4.1 Hz, 1H), 7.42-7.32 (m, 2H), 7.24-7.15 (m, 2H), 7.09 (d, J=7.7 Hz, 2H), 4.23-4.12 (m, 1H), 4.09-3.97 (m, 1H), 3.94-3.85 (m, 1H), 2.99-2.75 (m, 2H), 1.77-1.49 (m, 5H), 1.34-1.16 (m, 3H), 0.95-0.80 (m, 6H). LCMS (ESI) m/z calcd for $C_{22}H_{27}ClN_2O_3S$: 434.14. Found: 435.24/437.22 (M/M+2)$^+$.

Example 38

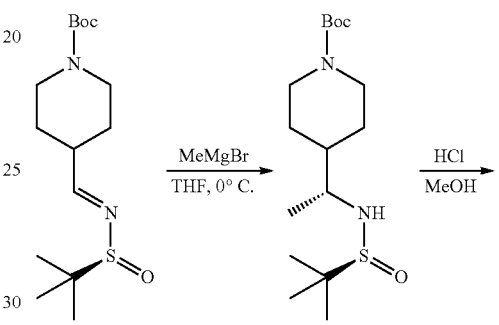

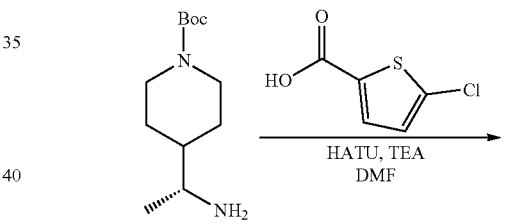

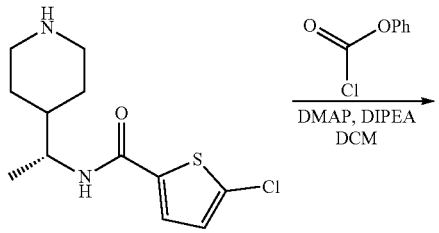

-continued

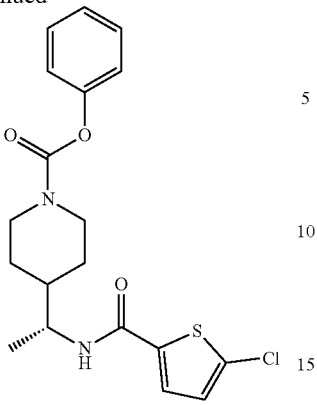

Preparation of Tert-butyl 4-((R)-1-(((S)-tert-butylsulfinyl)amino)ethyl)piperidine-1-carboxylate

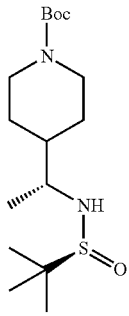

At 0° C., to a stirred solution of tert-butyl (S,E)-4-(((tert-butylsulfinyl)imino)methyl) piperidine-1-carboxylate (1.50 g, 4.74 mmol) in THF (15 mL) under nitrogen atmosphere was added 3.0 M methylmagnesium bromide in THF (3.16 mL, 9.48 mmol) dropwise. After stirred for 30 min, the reaction mixture was quenched with saturated aq. NH₄Cl and the mixture was extracted with ethylacetate. The organic layer was washed with brine and dried over Na₂SO₄. Solvent was removed under vacuum and the residue was purified by flash chromatography (silica gel, 0-50% ethyl acetate in petroleum ether) to afford a diastereomeric mixture (1.2 g), which was further purified by Gilson (C18, 5-40% MeCN in water with 0.1% formic acid) to afford the title compound (600 mg, 38%) as a colorless oil. LCMS (ESI) m/z calcd for $C_{16}H_{32}N_2O_3S$: 332.21. Found: 333.24 (M+1)⁺.

Preparation of Tert-butyl (R)-4-(1-aminoethyl)piperidine-1-carboxylate

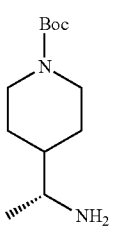

To tert-butyl 4-((R)-1-(((S)-tert-butylsulfinyl)amino)ethyl)piperidine-1-carboxylate (200 mg, 0.60 mmol) was added 0.4 M HCl in MeOH (1.7 mL, 0.68 mmol). After stirred at r.t. for 1 h, LCMS showed the reaction was complete. The reaction mixture was quenched with saturated aq. NaHCO₃ and extracted with DCM (×3). The combined organic layers were washed with brine and dried over Na₂SO₄. Solvent was removed under vacuum to afford the title compound (128 mg, 94%) as a viscous pale oil, which was used in the following step directly. LCMS (ESI) m/z calcd for $C_{12}H_{24}N_2O_2$: 228.18. Found: 251.31 (M+1)⁺.

Preparation of Tert-butyl (R)-4-(1-(5-chlorothiophene-2-carboxamido)ethyl) Piperidine-1-carboxylate

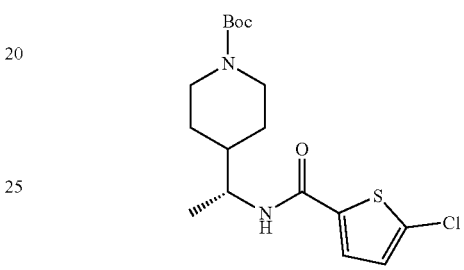

To a stirred solution of tert-butyl (R)-4-(1-aminoethyl)piperidine-1-carboxylate (128 mg, 0.56 mmol) and 5-chlorothiophene-2-carboxylic acid (100 mg, 0.62 mmol) in DMF (2 mL) under was added TEA (0.39 mL, 2.8 mmol) followed by HATU (100 mg, 0.62 mmol). After stirred at r.t. overnight, the reaction mixture was quenched with brine and the resulting mixture was extracted with DCM (×3). The combined organic layers were dried over Na₂SO₄. Solvent was removed under vacuum and the residue was purified by flash chromatography (silica gel, 0~70% ethyl acetate in petroleum ether) to afford the title compound (160 mg, 77%)) as a pale solid. LCMS (ESI) m/z calcd for $C_{17}H_{25}ClN_2O_3S$: 372.13. Found: 373.35/375.30 (M/M+2)⁺.

Preparation of (R)-5-chloro-N-(1-(piperidin-4-yl)ethyl)thiophene-2-carboxamide

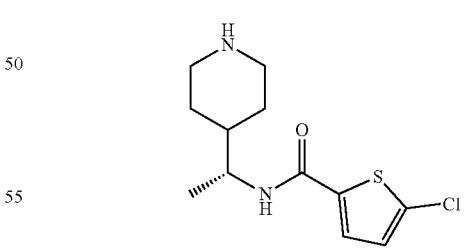

To a solution of tert-butyl (R)-4-(1-(5-chlorothiophene-2-carboxamido)ethyl)piperidine-1-carboxylate (160 mg, 0.43 mmol) in DCM (1.0 mL) was added 4 M HCl in dioxane (2.0 mL). After stirred at r.t. for 1 h, the reaction mixture was concentrated under vacuum to afford the title compound (133 mg, 100% yield) as a HCl salt, which was used in the following step directly. LCMS (ESI) m/z calcd for $C_{12}H_{17}ClN_2OS$: 272.08. Found: 273.20/275.18 (M/M+2)⁺.

Preparation of Phenyl (R)-4-(1-(5-chlorothiophene-2-carboxamido)ethyl)piperidine-1-carboxylate

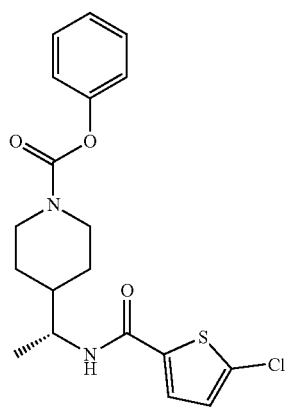 [SMILES: C[C@@H](NC(=O)c1ccc(Cl)s1)C1CCN(C(=O)Oc2ccccc2)CC1]

At 0° C., to a stirred solution of (R)-5-chloro-N-(1-(piperidin-4-yl)ethyl)thiophene-2-carboxamide (0.43 mmol) and DMAP (3.5 mg, 0.029 mmol) in DCM (3 mL) was added DIPEA (0.41 mL, 2.33 mmol) followed by phenyl carbonochloridate (136 mg, 0.87 mmol) drop wise. After stirred at r.t. for 2 h, the reaction mixture was partitioned between DCM/H$_2$O, and the layers were separated. The organic layer was washed with aq. NaHCO$_3$, brine and dried over Na$_2$SO$_4$. Solvent was removed under vacuum and the residue was purified by Gilson (C18, 10-50% MeCN in water with 0.1% formic acid) to afford the title compound (91 mg, 54%) as a white solid. $^1$H NMR (400 MHz, DMSO) δ 8.31 (d, J=8.6 Hz, 1H), 7.71 (d, J=4.1 Hz, 1H), 7.42-7.33 (m, 2H), 7.24-7.16 (m, 2H), 7.13-7.05 (m, 2H), 4.23-4.14 (m, 1H), 4.09-4.01 (m, 1H), 3.89-3.81 (m, 1H), 3.00-2.91 (m, 1H), 2.85-2.75 (m, 1H), 1.79-1.70 (m, 2H), 1.68-1.61 (m, 1H), 1.30-1.17 (m, 2H), 1.15 (d, J=6.8 Hz, 3H). LCMS (ESI) m/z calcd for C$_{19}$H$_{21}$ClN$_2$O$_3$S: 392.10. Found: 393.11/395.11 (M/M+2)$^+$.

Example 36

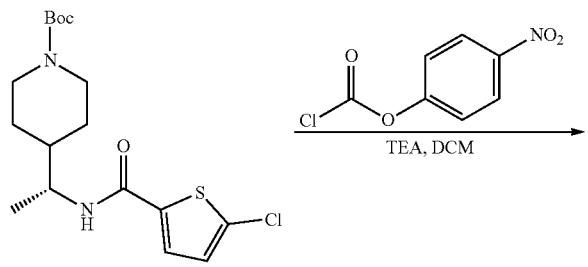

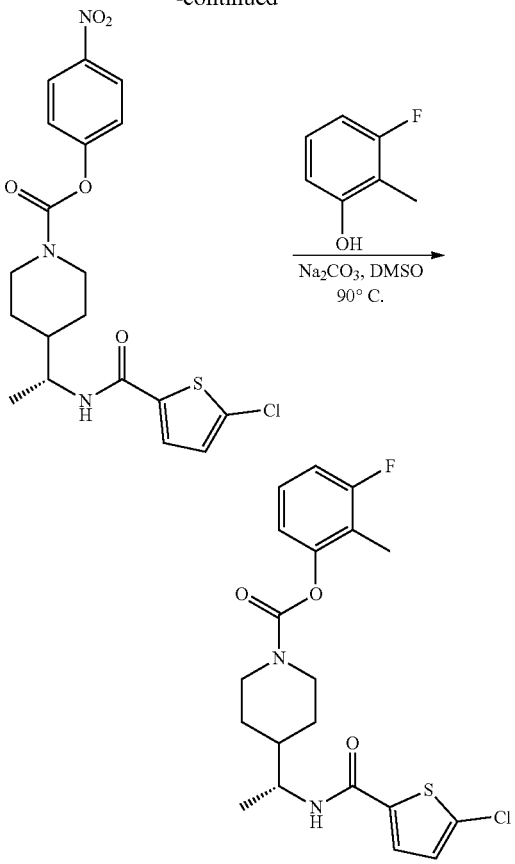

Preparation of 4-nitrophenyl (R)-4-(1-(5-chlorothiophene-2-carboxamido)ethyl) Piperidine-1-carboxylate

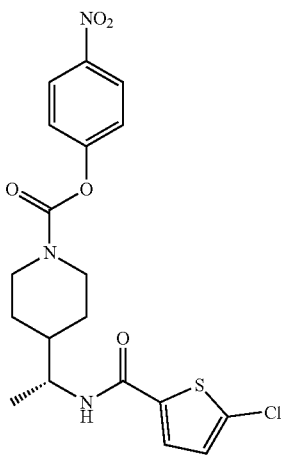 [SMILES: C[C@@H](NC(=O)c1ccc(Cl)s1)C1CCN(C(=O)Oc2ccc([N+](=O)[O-])cc2)CC1]

At 0° C., to a solution of 4-fluoro-N-(3-methyl-1-(piperidin-4-yl)butyl)benzamide (239 mg, 0.773 mmol) and TEA (0.54 mL, 3.86 mmol) in DCM (3 mL), was added 4-nitrophenyl carbonochloridate (171 mg, 0.85 mmol) drop wise. After stirred at r.t. for 2 h, the reaction was quenched with saturated NaHCO$_3$ aq. solution and extracted with EtOAc. The organic layer was washed with brine, dried over Na₂SO₄, filtered and concentrated to give the crude product which was purified by flash chromatography (silica gel, 0-30% EtOAc in PE) to afford the title compound (260 mg, 77% yield). LCMS (ESI) m/z calcd for C₁₉H₂₀ClN₃O₅S: 437.08. Found: 438.28/440.16 (M/M+2)⁺.

Preparation of 3-fluoro-2-methylphenyl (R)-4-(1-(5-chlorothiophene-2-carboxamido) ethyl)piperidine-1-carboxylate

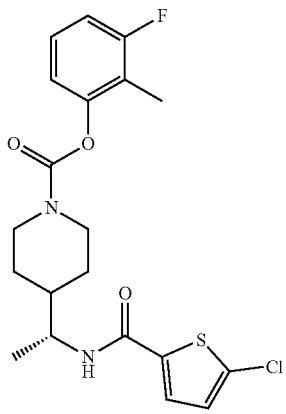 [SMILES: Cc1c(F)cccc1OC(=O)N1CCC([C@@H](C)NC(=O)c2ccc(Cl)s2)CC1]

A mixture of 4-nitrophenyl (R)-4-(1-(5-chlorothiophene-2-carboxamido)ethyl)piperidine-1-carboxylate (100 mg, 0.228 mmol), 3-fluoro-2-methylphenol (288 mg, 2.28 mmol), Na₂CO₃ (48 mg, 0.46 mmol), DMAP (4.8 mg, 0.039 mmol) and DMSO (2 mL) was heated to 90° C. for 3 days. The reaction mixture was partitioned between EtOAc/H₂O, and the layers were separated. The organic layer was washed with brine and dried over Na₂SO₄. Solvent was removed under vacuum and the residue was purified by Gilson (C18, 50-100% MeCN in water with 0.1% formic acid) to afford the title compound as a white solid. ¹H NMR (400 MHz, DMSO) δ 8.32 (d, J=7.7 Hz, 1H), 7.71 (d, J=4.0 Hz, 1H), 7.30-7.15 (m, 2H), 7.06 (t, J=8.7 Hz, 1H), 6.94 (d, J=8.1 Hz, 1H), 4.27-4.14 (m, 1H), 4.10-3.98 (m, 1H), 3.91-3.79 (m, 1H), 3.09-2.94 (m, 1H), 2.90-2.75 (m, 1H), 2.02 (s, 3H), 1.84-1.71 (m, 2H), 1.70-1.61 (m, 1H), 1.31-1.16 (m, 2H), 1.15 (d, J=6.7 Hz, 3H). LCMS (ESI) m/z calcd for C₂₀H₂₂ClFN₂O₃S: 424.10. Found: 425.32/427.25 (M/M+2)⁺.

Example 95

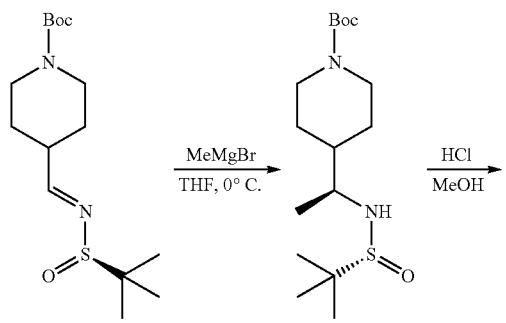

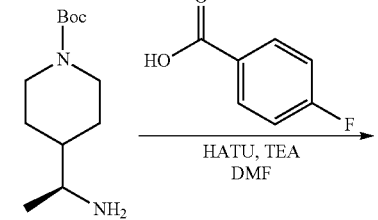

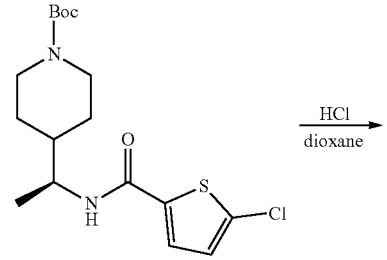

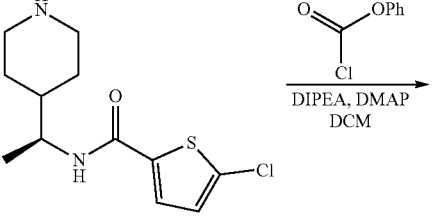

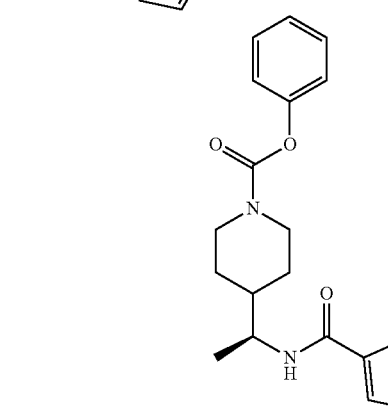

Preparation of Tert-butyl 4-((S)-1-(((R)-tert-butylsulfinyl)amino)ethyl)piperidine-1-carboxylate

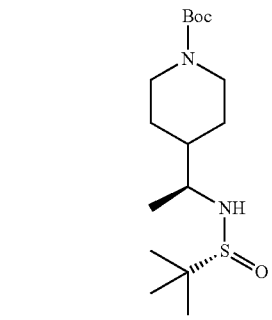 [SMILES: C[C@H](N[S@](=O)C(C)(C)C)C1CCN(C(=O)OC(C)(C)C)CC1]

At 0° C., to a stirred solution of tert-butyl (R,E)-4-(((tert-butylsulfinyl)imino) methyl) piperidine-1-carboxylate (1.50 g, 4.74 mmol) in THF (15 mL) under nitrogen atmosphere was added 3.0 M methylmagnesium bromide in THF (3.16 mL, 9.48 mmol) dropwise. After stirred for 30 min, the reaction mixture was quenched with saturated aq. NH$_4$Cl and the mixture was extracted with ethylacetate. The organic layer was washed with brine and dried over Na$_2$SO$_4$. Solvent was removed under vacuum and the residue was purified by flash chromatography (silica gel, 0-50% ethyl acetate in petroleum ether) to afford a diastereomeric mixture, which was further purified by Gilson (C18, 5-40% MeCN in water with 0.1% formic acid) to afford the major isomer (950 mg, 60% yield) as a colorless oil. LCMS (ESI) m/z calcd for C$_{16}$H$_{32}$N$_2$O$_3$S: 332.21. Found: 333.31 (M+1)$^+$.

Preparation of Tert-butyl (S)-4-(1-aminoethyl)piperidine-1-carboxylate

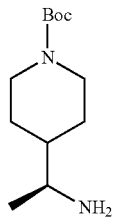

To tert-butyl 4-((S)-1-(((R)-tert-butylsulfinyl)amino) ethyl)piperidine-1-carboxylate (200 mg, 0.60 mmol) was added 0.4 M HCl in MeOH (1.7 mL, 0.68 mmol). After stirred at r.t. for 1 h, LCMS showed the reaction was complete. The reaction mixture was quenched with saturated aq. NaHCO$_3$ and extracted with DCM (×3). The combined organic layers were washed with brine and dried over Na$_2$SO$_4$. Solvent was removed under vacuum to afford the title compound (128 mg, 94%) as a viscous pale oil, which was used in the following step directly. LCMS (ESI) m/z calcd for C$_{12}$H$_{24}$N$_2$O$_2$: 228.18. Found: 229.41 (M+1)$^+$.

Preparation of Tert-butyl (S)-4-(1-(5-chlorothiophene-2-carboxamido)ethyl) Piperidine-1-carboxylate

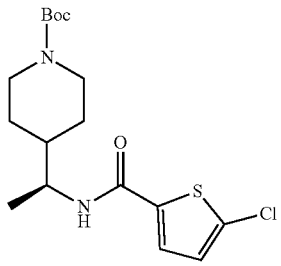 [SMILES: C[C@H](NC(=O)c1ccc(Cl)s1)C1CCN(C(=O)OC(C)(C)C)CC1]

To a stirred solution of tert-butyl (S)-4-(1-aminoethyl) piperidine-1-carboxylate (128 mg, 0.56 mmol) and 5-chlorothiophene-2-carboxylic acid (100 mg, 0.62 mmol) in DMF (2 mL) under was added TEA (0.39 mL, 2.8 mmol) followed by HATU (100 mg, 0.62 mmol). After stirred at r.t. overnight, the reaction mixture was quenched with brine and the resulting mixture was extracted with DCM (×3). The combined organic layers were dried over Na$_2$SO$_4$. Solvent was removed under vacuum and the residue was purified by flash chromatography (silica gel, 0~70% ethyl acetate in petroleum ether) to afford the title compound (160 mg, 77%) as a pale solid. LCMS (ESI) m/z calcd for C$_{17}$H$_{25}$ClN$_2$O$_3$S: 372.13. Found: 373.34/375.27 (M/M+2)$^+$.

Preparation of (S)-5-chloro-N-(1-(piperidin-4-yl) ethyl)thiophene-2-carboxamide

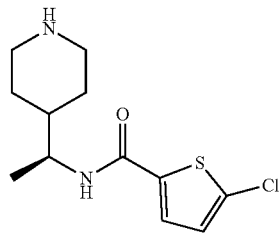 [SMILES: C[C@H](NC(=O)c1ccc(Cl)s1)C1CCNCC1]

To a solution of tert-butyl (S)-4-(1-(5-chlorothiophene-2-carboxamido)ethyl)piperidine-1-carboxylate (160 mg, 0.43 mmol) in DCM (1.0 mL) was added 4 M HCl in dioxane (2.0 mL). After stirred at r.t. for 1 h, the reaction mixture was concentrated under vacuum to afford the title compound as a HCl salt, which was used in the following step directly. LCMS (ESI) m/z calcd for C$_{12}$H$_{17}$ClN$_2$OS: 272.08. Found: 273.15/275.19 (M/M+2)$^+$.

Preparation of Phenyl (S)-4-(1-(5-chlorothiophene-2-carboxamido)ethyl)piperidine-1-carboxylate

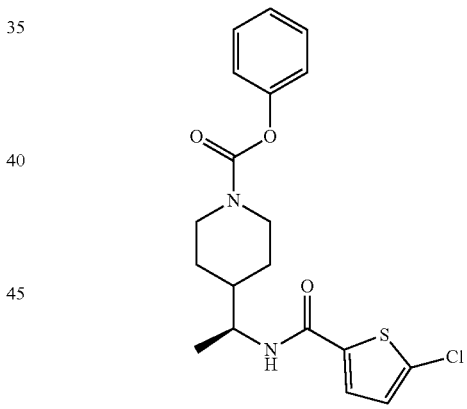

At 0° C., to a stirred solution of (S)-5-chloro-N-(1-(piperidin-4-yl)ethyl)thiophene-2-carboxamide (0.43 mmol) and DMAP (3.5 mg, 0.029 mmol) in DCM (3 mL) was added DIPEA (0.41 mL, 2.33 mmol) followed by phenyl carbonochloridate (136 mg, 0.87 mmol) drop wise. After stirred at r.t. for 2 h, the reaction mixture was partitioned between DCM/H$_2$O, and the layers were separated. The organic layer was washed with aq. NaHCO$_3$, brine and dried over Na$_2$SO$_4$. Solvent was removed under vacuum and the residue was purified by Gilson (C18, 10-50% MeCN in water with 0.1% formic acid) to afford the title compound (91 mg, 54%) as a white solid. $^1$H NMR (400 MHz, DMSO) δ 8.31 (d, J=8.6 Hz, 1H), 7.72 (d, J=4.1 Hz, 1H), 7.41-7.33 (m, 2H), 7.24-7.16 (m, 2H), 7.13-7.06 (m, 2H), 4.27-4.12 (m, 1H), 4.11-3.98 (m, 1H), 3.90-3.80 (m, 1H), 3.03-2.90 (m, 1H), 2.87-2.74 (m, 1H), 1.81-1.70 (m, 2H), 1.70-1.60

(m, 1H), 1.27-1.16 (m, 2H), 1.15 (d, J=6.8 Hz, 3H). LCMS (ESI) m/z calcd for $C_{19}H_{21}ClN_2O_3S$: 392.10. Found: 393.11/395.11 $(M/M+2)^+$.

Example 23

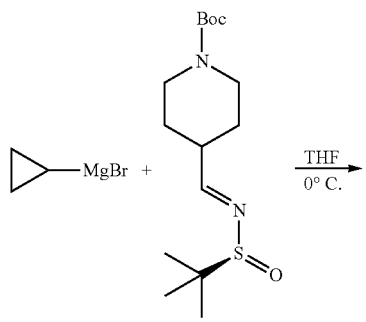

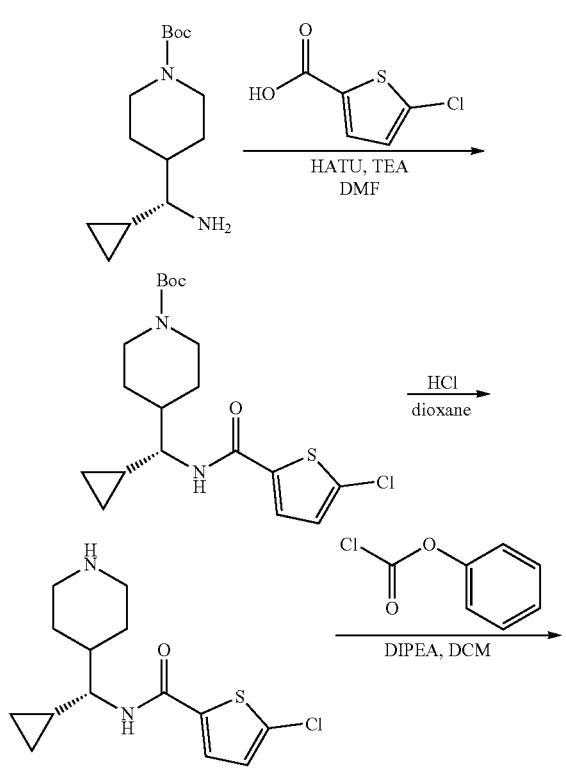

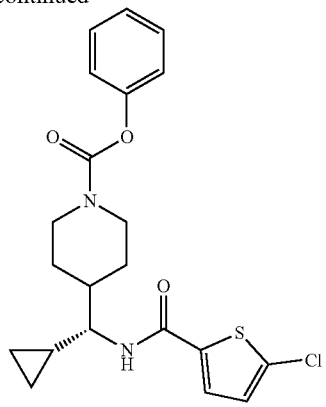

Preparation of Tert-butyl 4-((R)-(((S)-tert-butylsulfinyl)amino)(cyclopropyl)methyl) Piperidine-1-carboxylate At 0° C., to a stirred solution of tert-butyl (S,E)-4-(((tert-butylsulfinyl)imino)methyl) piperidine-1-carboxylate (2.0 g, 6.3 mmol) in THF (20 mL) under nitrogen atmosphere was added 2.0 M methylmagnesium bromide in THF (15.8 mL, 31.6 mmol) dropwise. After stirred at 0° C. for 30 min, LCMS showed complete conversion. The reaction mixture was quenched with saturated aq. $NH_4Cl$ and the mixture was extracted with ethylacetate. The organic layer was washed with brine and dried over $Na_2SO_4$. Solvent was removed under vacuum and the residue was purified by flash chromatography (silica gel, 0-50% ethyl acetate in petroleum ether) to afford a diastereomeric mixture, which was further purified by Gilson (C18, 5-40% MeCN in water with 0.1% formic acid) to afford the major isomer (300 mg, 13% yield) as a colorless oil. LCMS (ESI) m/z calcd for $C_{18}H_{34}N_2O_3S$: 358.23. Found: 359.45 $(M+1)^+$.

Preparation of Tert-butyl (R)-4-(amino(cyclopropyl)methyl)piperidine-1-carboxylate

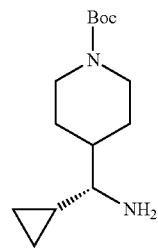 [SMILES: CC(C)(C)OC(=O)N1CCC([C@H](N)C2CC2)CC1]

To tert-butyl tert-butyl 4-((R)—(((S)-tert-butylsulfinyl) amino)(cyclopropyl)methyl)piperidine-1-carboxylate (300 mg, 0.84 mmol) was added 0.4 M HCl in MeOH (2.3 mL, 0.92 mmol). After stirred at r.t. for 1 h, LCMS showed the reaction was completed. The reaction mixture was quenched with saturated aq. NaHCO$_3$ and extracted with DCM (×3). The combined organic layers were washed with brine and dried over Na$_2$SO$_4$. Solvent was removed under vacuum to afford the title compound (192 mg, 90% yield) as a viscous pale oil, which was used in the following step directly. LCMS (ESI) m/z calcd for C$_{14}$H$_{26}$N$_2$O$_2$: 254.20. Found: 255.30 (M+1)$^+$.

Preparation of Tert-butyl (R)-4-((5-chlorothiophene-2-carboxamido)(cyclopropyl) Methyl)piperidine-1-carboxylate

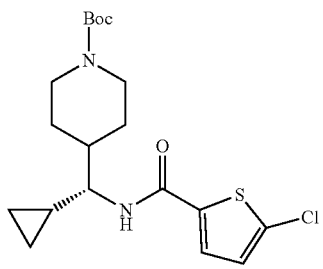 [SMILES: CC(C)(C)OC(=O)N1CCC([C@H](NC(=O)c2ccc(Cl)s2)C2CC2)CC1]

To a stirred solution of tert-butyl (R)-4-(amino(cyclopropyl)methyl)piperidine-1-carboxylate (80 mg, 0.31 mmol) and 5-chlorothiophene-2-carboxylic acid (51 mg, 0.31 mmol) in DMF (2 mL) under was added DIPEA (0.26 mL, 1.55 mmol) followed by HATU (164 mg, 0.432 mmol). After stirred at r.t. overnight, the reaction mixture was quenched with brine and the resulting mixture was extracted with DCM. The combined organic layers were dried over Na$_2$SO$_4$. Solvent was removed under vacuum and the residue was purified by flash chromatography (silica gel, 0~70% ethyl acetate in petroleum ether) to afford the title compound (120 mg, 96%) as a pale solid. LCMS (ESI) m/z calcd for C$_{19}$H$_{27}$ClN$_2$O$_3$S: 398.14. Found: 399.23/401.25 (M/M+2)$^+$.

Preparation of (R)-5-chloro-N-(cyclopropyl(piperidin-4-yl)methyl)thiophene-2-carboxamide

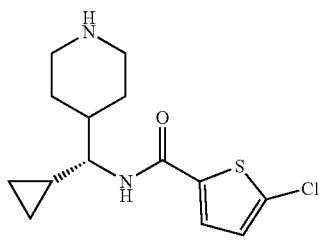 [SMILES: O=C(N[C@@H](C1CCNCC1)C1CC1)c1ccc(Cl)s1]

To a solution of tert-butyl (R)-4-((5-chlorothiophene-2-carboxamido)(cyclopropyl)methyl) piperidine-1-carboxylate (120 mg, 0.30 mmol) in DCM (2.0 mL) was added 4 M HCl in dioxane (3.0 mL). After stirred at r.t. for 1 h, the reaction mixture was concentrated under vacuum to afford the title compound (101 mg, 100% yield) as a HCl salt, which was used in the following step directly. LCMS (ESI) m/z calcd for C$_{14}$H$_{19}$ClN$_2$OS: 298.09. Found: 299.35/301.34 (M/M+2)$^+$.

Preparation of Phenyl (R)-4-((5-chlorothiophene-2-carboxamido)(cyclopropyl) Methyl)piperidine-1-carboxylate

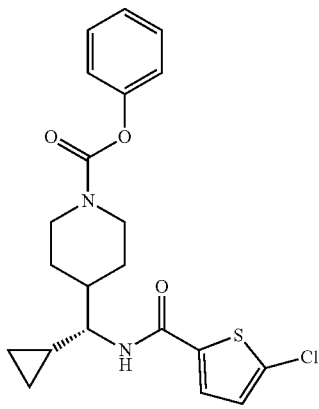 [SMILES: O=C(N[C@H](C1CC1)C1CCN(C(=O)Oc2ccccc2)CC1)c1ccc(Cl)s1]

At 0° C., to a stirred solution of (R)-5-chloro-N-(cyclopropyl(piperidin-4-yl)methyl) thiophene-2-carboxamide (101 mg, 0.30 mmol) and DMAP (3 mg, 0.018 mmol) in DCM (5 mL) was added DIPEA (0.3 mL, 1.44 mmol) followed by phenyl carbonochloridate (84 mg, 0.54 mmol) drop wise. After stirred at r.t. for 2 h, the reaction mixture was partitioned between DCM/H$_2$O, and the layers were separated. The organic layer was washed with aq. NaHCO$_3$, brine and dried over Na$_2$SO$_4$. Solvent was removed under vacuum and the residue was purified by Gilson (C18, 10-50% MeCN in water with 0.1% formic acid) to afford the title compound (63 mg, 50%) as a white solid. $^1$H NMR (400 MHz, DMSO) δ 8.41 (d, J=8.9 Hz, 1H), 7.74 (d, J=4.1 Hz, 1H), 7.42-7.32 (m, 2H), 7.25-7.16 (m, 2H), 7.14-7.05 (m, 2H), 4.22-4.01 (m, 2H), 3.19-3.10 (m, 1H), 3.02-2.78 (m, 2H), 1.96-1.73 (m, 3H), 1.37-1.23 (m, 2H), 1.05-0.95 (m, 1H), 0.64-0.55 (m, 1H), 0.40-0.27 (m, 2H), 0.22-0.13 (m, 1H). LCMS (ESI) m/z calcd for C$_{21}$H$_{23}$ClN$_2$O$_3$S: 418.11. Found: 419.40/421.36 (M/M+2)$^+$.

Example 7

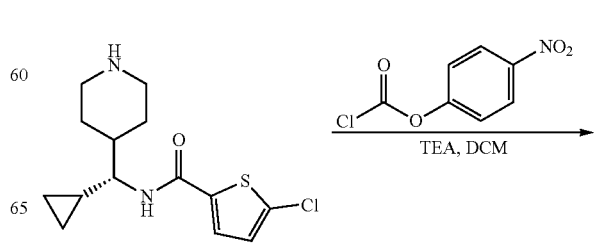

85

-continued

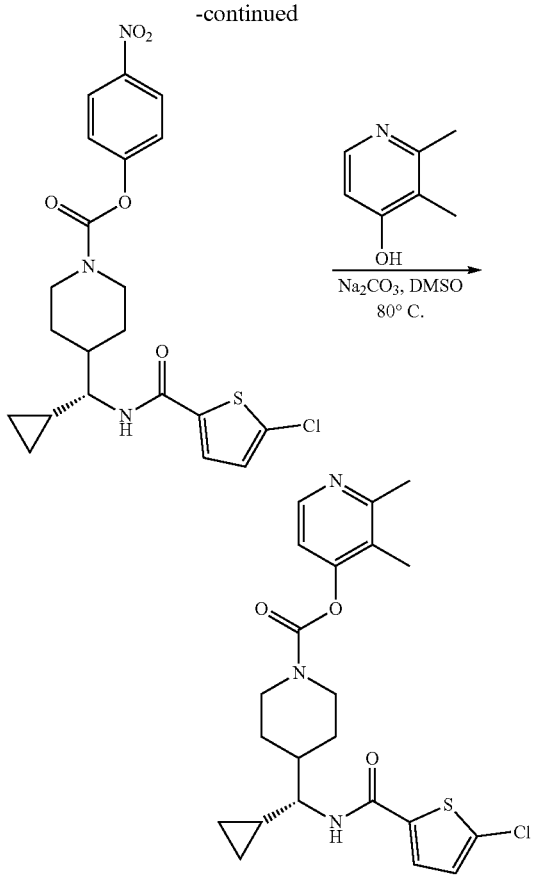

(R)-4-nitrophenyl 4-((5-chlorothiophene-2-carbox-amido)(cyclopropyl)methyl) Piperidine-1-carboxylate

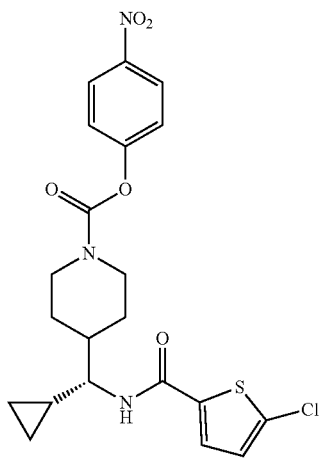 [SMILES: O=C(N[C@H](C1CC1)C1CCN(C(=O)Oc2ccc([N+](=O)[O-])cc2)CC1)c1ccc(Cl)s1]

(R)-5-chloro-N-(cyclopropyl(piperidin-4-yl)methyl)thiophene-2-carboxamide was dissolved in Dichloromethane (DCM) (10.0 mL) and treated with 4-nitrophenyl carbonochloridate (190 mg, 0.943 mmol) and DIEA (0.549 mL, 3.14 mmol) and stirred at r.t. for 16 h. Concentrated and purified by prep. TLC (DCM/MeOH 5%) to give the desired product as a solid.

86

(R)-2,3-dimethylpyridin-4-yl 4-((5-chlorothiophene-2 carboxamido) (cyclopropyl) Methyl) piperidine-1-carboxylate

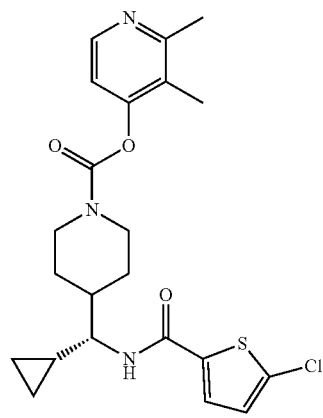 [SMILES: Cc1nccc(OC(=O)N2CCC([C@H](NC(=O)c3ccc(Cl)s3)C3CC3)CC2)c1C]

To a suspension of 2,3-dimethylpyridin-4-ol (46.5 mg, 0.377 mmol), DMAP (13.83 mg, 0.113 mmol) and Na2CO3 (80 mg, 0.754 mmol) in Dimethyl Sulfoxide (DMSO) (3.0 mL) was added 4-nitrophenyl (R)-4-((5-chlorothiophene-2-carboxamido)(cyclopropyl)methyl)piperidine-1-carboxylate (35 mg, 0.075 mmol) and stirred at 80° C. for 16 h. Cooled to r.t., diluted with water, extracted with DCM, dried over sodium sulfate and concentrated. Purification by Gilson afforded the desired product as a solid (20.3 mg, 60.1% yield).

$^{1}$H NMR (400 MHz, METHANOL-d$_{4}$) δ ppm 8.20 (d, J=5.3 Hz, 1H) 7.58 (d, J=3.5 Hz, 1H) 6.96-7.12 (m, 2H) 4.28-4.42 (m, 1H) 4.10-4.27 (m, 1H) 3.01-3.22 (m, 2H) 2.76-3.00 (m, 1H) 2.51 (s, 3H) 2.14 (s, 3H) 2.08 (d, J=13.1 Hz, 1H) 1.79-2.00 (m, 2H) 1.29-1.51 (m, 2H) 0.96-1.12 (m, 1H) 0.62-0.75 (m, 1H) 0.42-0.52 (m, 1H) 0.33-0.42 (m, 1H) 0.19-0.31 (m, 1H).

LCMS (ESI) m/z calcd for C22H26ClN3O3S: 447.14 Found: 448.5 (M/M+1)$^{+}$.

The following compounds were synthesized following the procedure described for examples 23 and 7 using appropriate materials.

Example 17

(R)-2-methylpyridin-3-yl 4-((5-chlorothiophene-2-carboxamido)(cyclopropyl)methyl) Piperidine-1-carboxylate

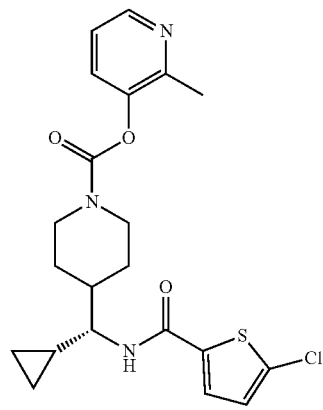 [SMILES: Cc1ncccc1OC(=O)N1CCC([C@H](NC(=O)c2ccc(Cl)s2)C2CC2)CC1]

¹H NMR (400 MHz, METHANOL-d₄) δ ppm 8.27 (d, J=4.3 Hz, 1H) 7.58 (d, J=3.9 Hz, 1H) 7.53 (d, J=8.0 Hz, 1H) 7.30 (dd, J=7.8, 5.1 Hz, 1H) 7.03 (d, J=3.9 Hz, 1H) 4.29-4.47 (m, 1H) 4.09-4.29 (m, 1H) 3.13-3.22 (m, 1H) 3.08 (s, 1H) 2.82-3.00 (m, 1H) 2.39 (br. s., 3H) 2.07 (d, J=13.1 Hz, 1H) 1.78-2.01 (m, 2H) 1.29-1.55 (m, 2H) 0.98-1.14 (m, 1H) 0.59-0.78 (m, 1H) 0.42-0.55 (m, 1H) 0.33-0.42 (m, 1H) 0.19-0.32 (m, 1H)
LCMS (ESI) m/z calcd for C21H24ClN3O3S: 433.12 Found: 434.57 (M/M+1)⁺.

Example 19

(R)-3-fluoro-2-methylphenyl 4-((5-chlorothiophene-2-carboxamido) (cyclopropyl) Methyl) piperidine-1-carboxylate

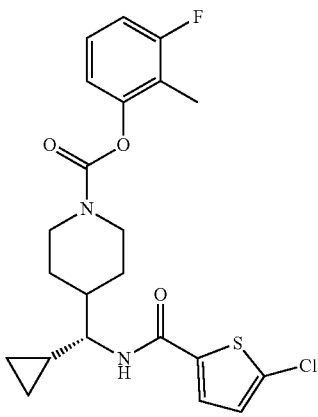 [SMILES: Cc1c(F)cccc1OC(=O)N1CCC([C@H](NC(=O)c2ccc(Cl)s2)C2CC2)CC1]

¹H NMR (400 MHz, METHANOL-d₄) δ ppm 7.58 (d, J=3.7 Hz, 1H) 7.18 (q, J=7.7 Hz, 1H) 7.03 (d, J=3.7 Hz, 1H) 6.94 (t, J=8.8 Hz, 1H) 6.86 (d, J=8.2 Hz, 1H) 4.29-4.44 (m, 1H) 4.11-4.25 (m, 1H) 3.13-3.22 (m, 1H) 2.98-3.13 (m, 1H) 2.79-2.97 (m, 1H) 2.06 (br. s., 4H) 1.77-2.00 (m, 2H) 1.27-1.51 (m, 2H) 0.98-1.13 (m, 1H) 0.61-0.75 (m, 1H) 0.42-0.54 (m, 1H) 0.33-0.42 (m, 1H) 0.21-0.30 (m, 1H) LCMS (ESI) m/z calcd for C22H24ClFN2O3S: 450.12 Found: 451.18 (M/M+1)⁺.

Example 24

(R)-2-methylpyridin-3-yl 4-(cyclopropyl(5-methyl-thiophene-2-carboxamido) methyl) Piperidine-1-carboxylate

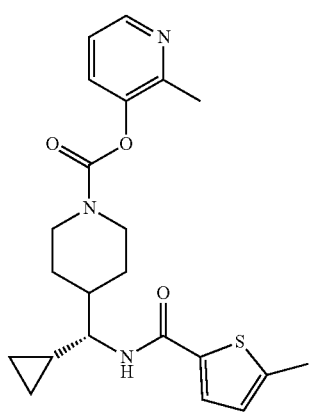 [SMILES: Cc1ccc(C(=O)N[C@H](C2CC2)C2CCN(C(=O)Oc3cccnc3C)CC2)s1]

¹H NMR (400 MHz, METHANOL-d₄) δ ppm 8.27 (d, J=4.9 Hz, 1H) 7.44-7.61 (m, 2H) 7.30 (dd, J=8.1, 5.0 Hz, 1H) 6.81 (d, J=3.5 Hz, 1H) 4.29-4.50 (m, 1H) 4.06-4.28 (m, 1H) 3.15-3.24 (m, 1H) 2.99-3.14 (m, 1H) 2.79-2.99 (m, 1H) 2.50 (s, 3H) 2.39 (d, J=3.5 Hz, 3H) 2.01-2.12 (m, 1H) 1.81-2.00 (m, 2H) 1.29-1.57 (m, 2H) 0.95-1.12 (m, 1H) 0.61-0.75 (m, 1H) 0.42-0.53 (m, 1H) 0.32-0.42 (m, 1H) 0.20-0.31 (m, 1H) LCMS (ESI) m/z calcd for C22H27N3O3S: 413.18 Found: 414.67 (M/M+1)⁺.

Example 32

(R)-2,3-dimethylpyridin-4-yl 4-(cyclopropyl(5-methylthiophene-2-carboxamido) Methyl)piperidine-1-carboxylate

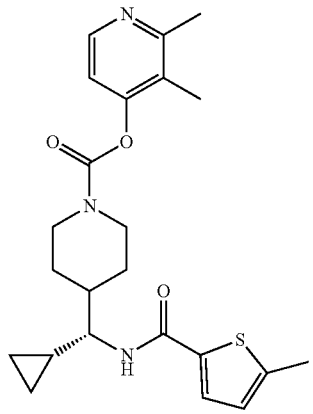 [SMILES: Cc1ccc(C(=O)N[C@H](C2CC2)C2CCN(C(=O)Oc3ccnc(C)c3C)CC2)s1]

¹H NMR (400 MHz, METHANOL-d₄) δ ppm 8.20 (d, J=5.5 Hz, 1H) 7.54 (d, J=3.5 Hz, 1H) 7.04 (d, J=5.5 Hz, 1H) 6.81 (d, J=3.5 Hz, 1H) 4.26-4.46 (m, 1H) 4.06-4.24 (m, 1H) 3.14-3.23 (m, 1H) 2.99-3.14 (m, 1H) 2.82-2.99 (m, 1H) 2.51 (d, J=3.5 Hz, 6H) 2.14 (s, 3H) 2.03-2.11 (m, 1H) 1.79-2.01 (m, 2H) 1.28-1.53 (m, 2H) 0.94-1.13 (m, 1H) 0.60-0.75 (m, 1H) 0.42-0.53 (m, 1H) 0.32-0.42 (m, 1H) 0.19-0.32 (m, 1H) LCMS (ESI) m/z calcd for C23H29N3O3S: 427.19 Found: 429.28 (M/M+2)⁺.

Example 112

(S)-4,6-dimethylpyrimidin-5-yl 4-((5-chlorothiophene-2-carboxamido) (cyclopropyl)methyl)piperidine-1-carboxylate

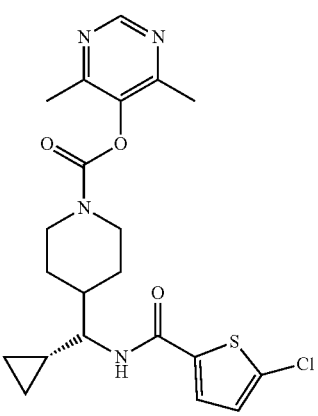

¹H NMR (400 MHz, METHANOL-d₄) δ ppm 8.70 (s, 1H) 7.58 (d, J=3.7 Hz, 1H) 7.03 (d, J=3.3 Hz, 1H) 4.32-4.49 (m, 1H) 4.05-4.29 (m, 1H) 3.05-3.23 (m, 2H) 2.79-3.04 (m, 1H) 2.36 (d, J=4.7 Hz, 6H) 2.04-2.16 (m, 1H) 1.73-2.03 (m, 2H) 1.28-1.56 (m, 2H) 0.93-1.17 (m, 1H) 0.60-0.76 (m, 1H) 0.43-0.54 (m, 1H) 0.33-0.43 (m, 1H) 0.18-0.31 (m, 1H)

LCMS (ESI) m/z calcd for C21H25ClN4O3S: 448.97. Found: 449.25 (M+1)⁺.

Example 113

(R)-4,6-dimethylpyrimidin-5-yl 4-(cyclopropyl(5-methylthiophene-2-carboxamido) Methyl)piperidine-1-carboxylate

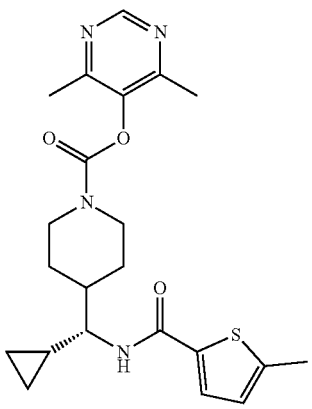 [SMILES: Cc1ccc(C(=O)N[C@H](C2CC2)C2CCN(C(=O)Oc3c(C)ncnc3C)CC2)s1]

¹H NMR (400 MHz, METHANOL-d₄) δ ppm 8.69 (s, 1H) 7.52 (d, J=3.5 Hz, 1H) 6.70-6.87 (m, 1H) 4.29-4.45 (m, 1H) 4.06-4.26 (m, 1H) 3.02-3.26 (m, 2H) 2.82-3.02 (m, 1H) 2.49 (s, 3H) 2.36 (br. s., 3H) 2.34 (br. s., 3H) 2.03-2.13 (m, 1H) 1.81-2.02 (m, 2H) 1.29-1.52 (m, 2H) 0.96-1.12 (m, 1H) 0.60-0.73 (m, 1H) 0.41-0.51 (m, 1H) 0.32-0.40 (m, 1H) 0.20-0.31 (m, 1H)

LCMS (ESI) m/z calcd for C22H28N4O3S: 428.55. Found: 429.00 (M+1)⁺.

Example 114

(R)-2,4-dimethylpyridin-3-yl 4-((5-chlorothiophene-2-carboxamido)(cyclopropyl) Methyl)piperidine-1-carboxylate

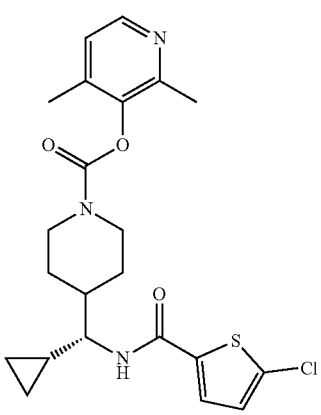 [SMILES: Cc1ccnc(C)c1OC(=O)N1CCC([C@H](NC(=O)c2ccc(Cl)s2)C2CC2)CC1]

¹H NMR (400 MHz, METHANOL-d₄) δ ppm 8.11 (d, J=4.9 Hz, 1H) 7.57 (d, J=4.1 Hz, 1H) 7.16 (d, J=4.9 Hz, 1H) 7.02 (d, J=4.1 Hz, 1H) 4.31-4.48 (m, 1H) 4.06-4.27 (m, 1H) 3.04-3.23 (m, 2H) 2.80-3.03 (m, 1H) 2.33 (s, 3H) 2.18 (br. s., 3H) 2.02-2.11 (m, 1H) 1.79-2.01 (m, 2H) 1.23-1.54 (m, 2H) 0.97-1.12 (m, 1H) 0.61-0.76 (m, 1H) 0.42-0.53 (m, 1H) 0.31-0.42 (m, 1H) 0.18-0.31 (m, 1H).

LCMS (ESI) m/z calcd for C22H26ClN3O3S: 447.98. Found: 448.23 (M+1)⁺.

Example 115

(R)-pyrimidin-5-yl 4-((5-chlorothiophene-2-carboxamido)(cyclopropyl) Methyl)piperidine-1-carboxylate

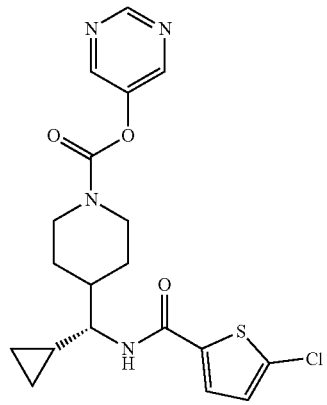 [SMILES: O=C(N[C@H](C1CC1)C1CCN(C(=O)Oc2cncnc2)CC1)c1ccc(Cl)s1]

¹H NMR (400 MHz, METHANOL-d₄) δ ppm 8.96 (s, 1H) 8.66 (s, 2H) 7.57 (d, J=4.1 Hz, 1H) 7.01 (d, J=4.1 Hz, 1H) 4.26-4.42 (m, 1H) 4.08-4.27 (m, 1H) 3.09-3.21 (m, 1H) 2.97-3.09 (m, 1H) 2.80-2.97 (m, 1H) 2.00-2.12 (m, 1H) 1.76-1.99 (m, 2H) 1.27-1.54 (m, 2H) 0.94-1.10 (m, 1H) 0.60-0.74 (m, 1H) 0.41-0.51 (m, 1H) 0.30-0.40 (m, 1H) 0.17-0.28 (m, 1H).

LCMS (ESI) m/z calcd for C19H21ClN4O3S: 420.91. Found: 421.19 (M+1)⁺.

Example 91

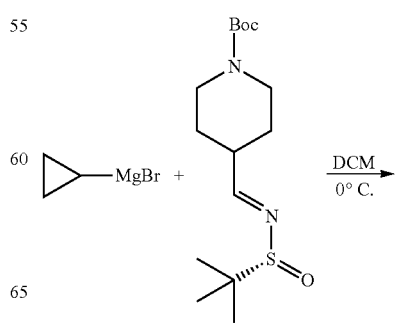

91

-continued

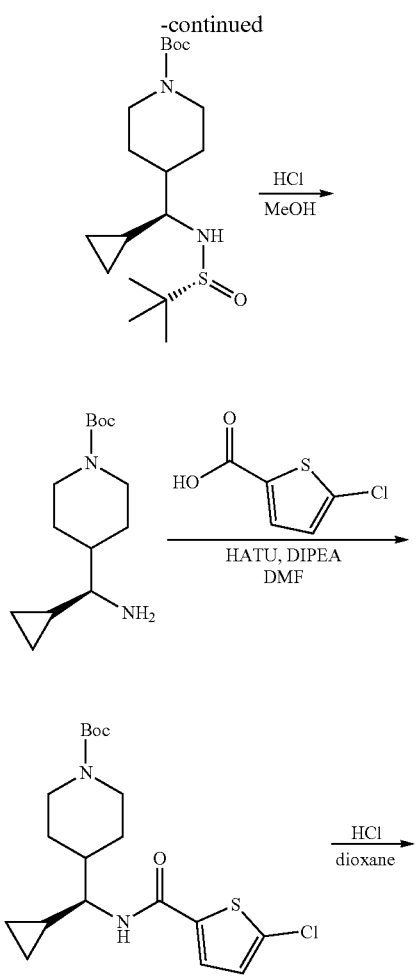

Preparation of Tert-butyl 4-((R)—(((S)-tert-butylsulfinyl)amino)(cyclopropyl)methyl) Piperidine-1-carboxylate

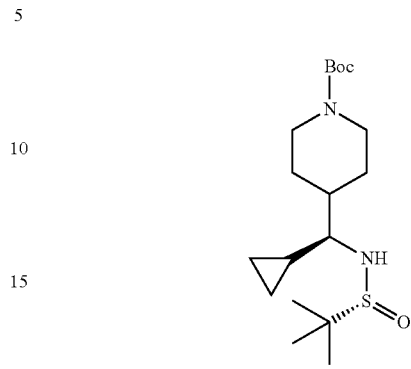

At 0° C., to a stirred solution of tert-butyl (R,E)-4-(((tert-butylsulfinyl)imino)methyl) piperidine-1-carboxylate (1.50 g, 4.74 mmol) in THF (15 mL) under nitrogen atmosphere was added 1.0 M methylmagnesium bromide in THF (24 mL, 23.7 mmol) dropwise. After stirred at 00° C. for 60 min, the reaction mixture was quenched with saturated aq. $NH_4Cl$ and the mixture was extracted with ethylacetate. The organic layer was washed with brine and dried over $Na_2SO_4$. Solvent was removed under vacuum and the residue was purified by flash chromatography (silica gel, 0-50% ethyl acetate in petroleum ether) to afford a diastereomeric mixture, which was further purified by Gilson (C18, 5-40% MeCN in water with 0.1% formic acid) to afford the major isomer (230 mg, 14% yield) as a colorless oil. LCMS (ESI) m/z calcd for $C_{18}H_{34}N_2O_3S$: 358.23. Found: 359.73 $(M+1)^+$.

Preparation of Tert-butyl (S)-4-(amino(cyclopropyl)methyl)piperidine-1-carboxylate

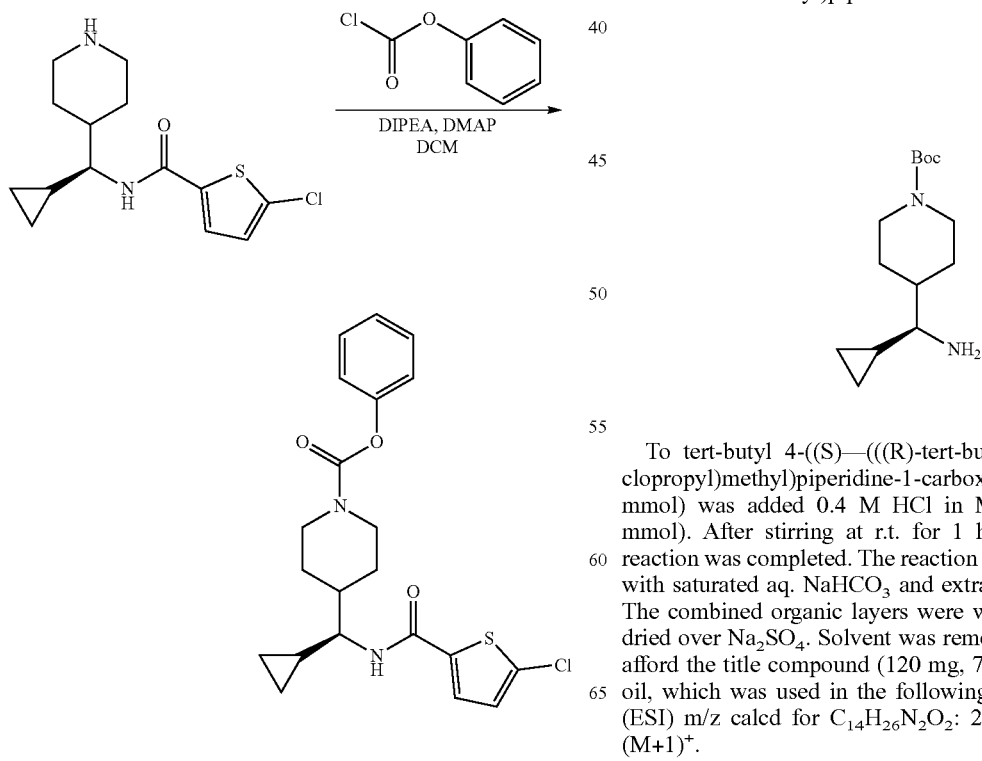

To tert-butyl 4-((S)—(((R)-tert-butylsulfinyl)amino)(cyclopropyl)methyl)piperidine-1-carboxylate (230 mg, 0.64 mmol) was added 0.4 M HCl in MeOH (1.8 mL, 0.71 mmol). After stirring at r.t. for 1 h, LCMS showed the reaction was completed. The reaction mixture was quenched with saturated aq. $NaHCO_3$ and extracted with DCM (×3). The combined organic layers were washed with brine and dried over $Na_2SO_4$. Solvent was removed under vacuum to afford the title compound (120 mg, 74%) as a viscous pale oil, which was used in the following step directly. LCMS (ESI) m/z calcd for $C_{14}H_{26}N_2O_2$: 254.20. Found: 255.39 $(M+1)^+$.

Preparation of Tert-butyl (S)-4-((5-chlorothiophene-2-carboxamido)(cyclopropyl) Methyl)piperidine-1-carboxylate

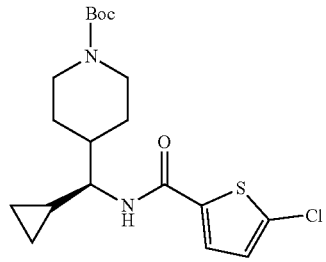 [SMILES: CC(C)(C)OC(=O)N1CCC([C@@H](NC(=O)c2ccc(Cl)s2)C2CC2)CC1]

To a stirred solution of tert-butyl (S)-4-(amino(cyclopropyl)methyl)piperidine-1-carboxylate (120 mg, 0.47 mmol) and 5-chlorothiophene-2-carboxylic acid (77 mg, 0.47 mmol) in DMF (2 mL) under was added DIPEA (0.3 mL, 0.94 mmol) followed by HATU (246 mg, 0.71 mmol). After stirred at r.t. overnight, the reaction mixture was quenched with brine and the resulting mixture was extracted with DCM. The combined organic layers were dried over Na$_2$SO$_4$. Solvent was removed under vacuum and the residue was purified by flash chromatography (silica gel, 0-50% ethyl acetate in petroleum ether) to afford the title compound (170 mg, 91%) as a pale solid. LCMS (ESI) m/z calcd for C$_{19}$H$_{27}$ClN$_2$O$_3$S: 398.14. Found: 399.32/401.34 (M/M+2)$^+$.

Preparation of (S)-5-chloro-N-(cyclopropyl(piperidin-4-yl)methyl)thiophene-2-carboxamide

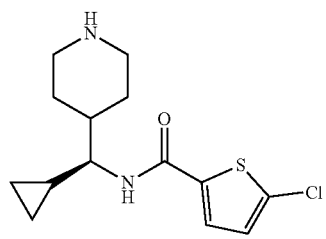 [SMILES: O=C(N[C@H](C1CCNCC1)C1CC1)c1ccc(Cl)s1]

To a solution of tert-butyl (S)-4-((5-chlorothiophene-2-carboxamido)(cyclopropyl)methyl) piperidine-1-carboxylate (170 mg, 0.43 mmol) in DCM (1.0 mL) was added 4 M HCl in dioxane (2.0 mL). After stirred at r.t. for 1 h, the reaction mixture was concentrated under vacuum to afford the title compound (140 mg, 100% yield) as a HCl salt, which was used in the following step directly. LCMS (ESI) m/z calcd for C$_{14}$H$_{19}$ClN$_2$OS: 298.09. Found: 299.34/301.33 (M/M+2)$^+$.

Preparation of Phenyl (S)-4-((5-chlorothiophene-2-carboxamido)(cyclopropyl) Methyl)piperidine-1-carboxylate

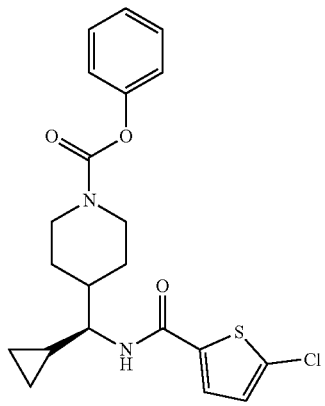 [SMILES: O=C(N[C@@H](C1CC1)C1CCN(C(=O)Oc2ccccc2)CC1)c1ccc(Cl)s1]

At 0° C., to a stirred solution of (S)-5-chloro-N-(cyclopropyl(piperidin-4-yl)methyl) thiophene-2-carboxamide (120 mg, 0.36 mmol) and DMAP (4.4 mg, 0.036 mmol) in DCM (3 mL) was added DIPEA (0.3 mL, 1.43 mmol) followed by phenyl carbonochloridate (84 mg, 0.54 mmol) drop wise. After stirred at r.t. for 2 h, the reaction mixture was partitioned between DCM/H$_2$O, and the layers were separated. The organic layer was washed with aq. NaHCO$_3$, brine and dried over Na$_2$SO$_4$. Solvent was removed under vacuum and the residue was purified by Gilson (C18, 10-50% MeCN in water with 0.1% formic acid) to afford the title compound (115 mg, 77%) as a white solid. $^1$H NMR (400 MHz, DMSO) δ 8.42 (d, J=8.9 Hz, 1H), 7.74 (d, J=4.0 Hz, 1H), 7.41-7.33 (m, 2H), 7.24-7.16 (m, 2H), 7.10 (d, J=7.6 Hz, 2H), 4.22-4.01 (m, 2H), 3.19-3.11 (m, 1H), 3.02-2.78 (m, 2H), 1.96-1.73 (m, 3H), 1.34-1.17 (m, 2H), 1.05-0.96 (m, 1H), 0.63-0.54 (m, 1H), 0.40-0.28 (m, 2H), 0.22-0.14 (m, 1H). LCMS (ESI) m/z calcd for C$_{21}$H$_{23}$ClN$_2$O$_3$S: 418.11. Found: 419.34/421.18 (M/M+2)$^+$.

Examples 14, 20, 31 and 49

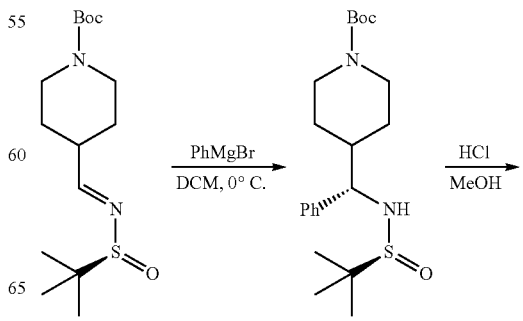

-continued

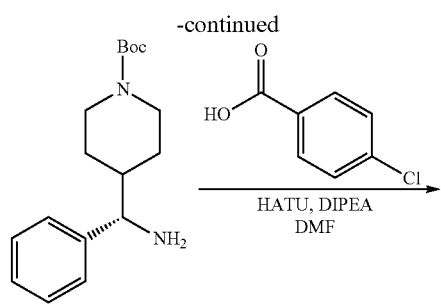

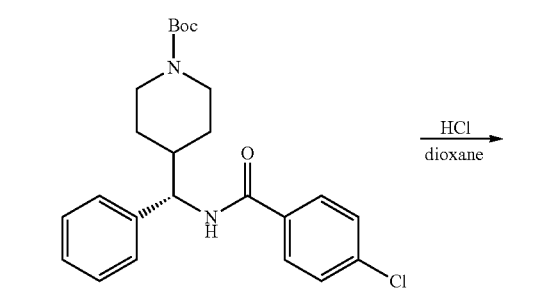

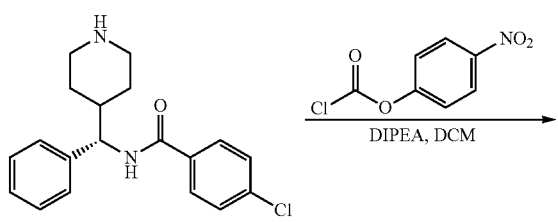

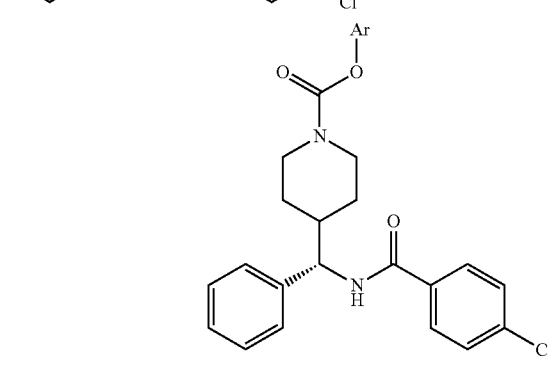

Preparation of Tert-butyl 4-((S)—(((S)-tert-butylsulfinyl)amino)(phenyl)methyl) Piperidine-1-carboxylate

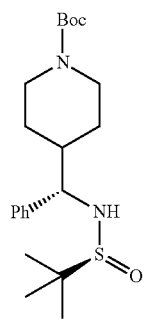

At 0° C., to a solution of (S,E)-tert-butyl 4-{{tertbutylsulfinyiimino) methyl)piperidine-1-carboxylate (5.0 g, 15.8 mmol) in DCM (100 mL) under nitrogen atmosphere, was added PhMgBr (26.4 ml, 79.1 mmol) (3M in diethyl ether) drop wise and the reaction stirred for 2 h at this temperature. The reaction was carefully quenched via the addition of saturated aqueous NH$_4$Cl. The solid were broken up by the addition of 1N HCl. The layers were separated and the aqueous phase was extracted with DCM. The combined organic layer was washed with brine, dried over Na$_2$SO$_4$, filtered and concentrated to give the crude product which was purified by flash chromatography (silica gel, 0-30% EtOAc in PE) to afford the title compound (3.4 g, 55% yield). LCMS (ESI) m/z calcd for $C_{21}H_{34}N_2O_3S$: 394.23. Found: 395.51 (M+1)$^+$.

Preparation of Tert-butyl (S)-4-(amino(phenyl)methyl)piperidine-1-carboxylate

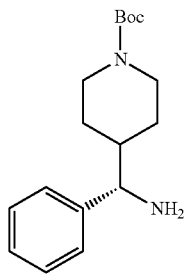 [SMILES: CC(C)(C)OC(=O)N1CCC([C@H](N)c2ccccc2)CC1]

To a solution of tert-butyl 4-((S)—(((S)-tert-butylsulfinyl)amino)(phenyl)methyl)piperidine-1-carboxylate (3.3 g, 8.38 mmol) in MeOH (22 mL) was added 4 M HCl in MeOH (2.5 mL, 10.05 mmol). After stirred at r.t. for 1 h, LCMS showed the reaction was complete. The reaction mixture was quenched with saturated aq. NaHCO$_3$ and extracted with DCM (×3). The combined organic layers were washed with brine and dried over Na$_2$SO$_4$. Solvent was removed under vacuum to afford the title compound (3.1 g, 100%) as a viscous pale oil, which was used in the following step directly. LCMS (ESI) m/z calcd for $C_{17}H_{26}N_2O_2$: 290.20. Found: 291.63 (M+1)$^+$.

Preparation of Tert-butyl (S)-4-((4-chlorobenzamido)(phenyl)methyl)piperidine-1-carboxylate

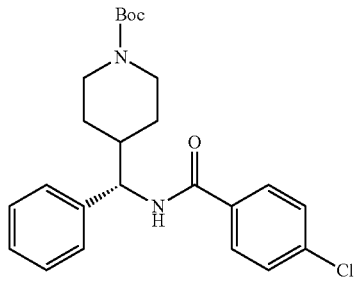 [SMILES: CC(C)(C)OC(=O)N1CCC([C@H](NC(=O)c2ccc(Cl)cc2)c2ccccc2)CC1]

To a stirred solution of tert-butyl (S)-4-(amino(phenyl) methyl)piperidine-1-carboxylate (1.5 g, 5.17 mmol) and 4-chlorobenzoic acid (1.21 g, 7.76 mmol) in DMF (15 mL) under was added DIPEA (1.8 mL, 10.34 mmol) followed by HATU (2.95 g, 7.76 mmol). After stirred at r.t. overnight, the reaction mixture was quenched with brine and the resulting mixture was extracted with DCM. The combined organic layers were dried over $Na_2SO_4$. Solvent was removed under vacuum and the residue was purified by flash chromatography (silica gel, 0-25% ethyl acetate in petroleum ether) to afford the title compound (1.3 g, 58%)) as a pale solid. LCMS (ESI) m/z calcd for $C_{24}H_{29}ClN_2O_3$: 428.19. Found: 429.37/431.35 $(M/M+2)^+$.

Preparation of (S)-4-chloro-N-(phenyl(piperidin-4-yl)methyl)benzamide

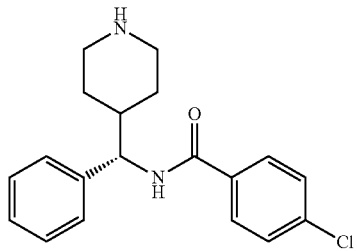 [SMILES: O=C(N[C@H](c1ccccc1)C1CCNCC1)c1ccc(Cl)cc1]

To a solution of tert-butyl (S)-4-((4-chlorobenzamido)(phenyl)methyl)piperidine-1-carboxylate (1.3 g, 3.04 mmol) in DCM (6.0 mL) was added 4 M HCl in dioxane (20 mL). After stirred at r.t. for 1 h, the reaction mixture was concentrated under vacuum to afford the title compound (1.11 g, 100% yield) as a HCl salt, which was used in the following step directly. LCMS (ESI) m/z calcd for $C_{19}H_{21}ClN_2O$: 328.13. Found: 329.29/331.34 $(M/M+2)^+$.

Preparation of 4-nitrophenyl (S)-4-((4-chlorobenzamido)(phenyl)methyl)piperidine-1-carboxylate

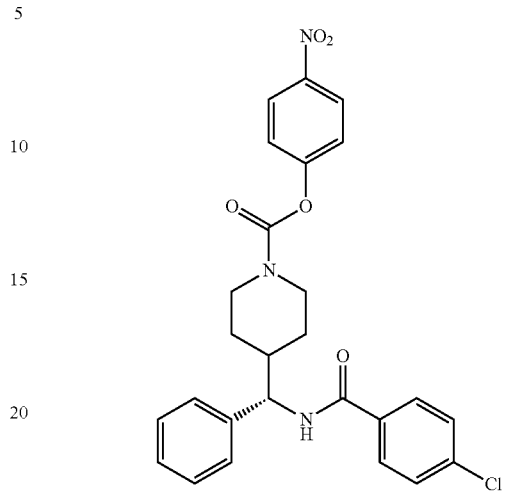

At 0° C., to a stirred solution of (S)-4-chloro-N-(phenyl (piperidin-4-yl)methyl)benzamide (1.11 g, 3.04 mmol) in DCM (12 mL) was added DIPEA (1.56 mL, 8.92 mmol) followed by phenyl carbonochloridate (863 mg, 4.28 mmol) drop wise. After stirred at r.t. for 2 h, the reaction mixture was partitioned between $DCM/H_2O$, and the layers were separated. The organic layer was washed with aq. $NaHCO_3$, brine and dried over $Na_2SO_4$. Solvent was removed under vacuum and the residue was purified by flash chromatography (silica gel, 0-30% ethyl acetate in petroleum ether) to afford the title compound (1.25 g, 83%)) as a pale solid. LCMS (ESI) m/z calcd for $C_{26}H_{24}ClN_3O_5$: 493.14. Found: 494.10/496.14 $(M/M+2)^+$.

Example 14

Preparation of 2-methylpyridin-3-yl (S)-4-((4-chlorobenzamido)(phenyl)methyl) Piperidine-1-carboxylate

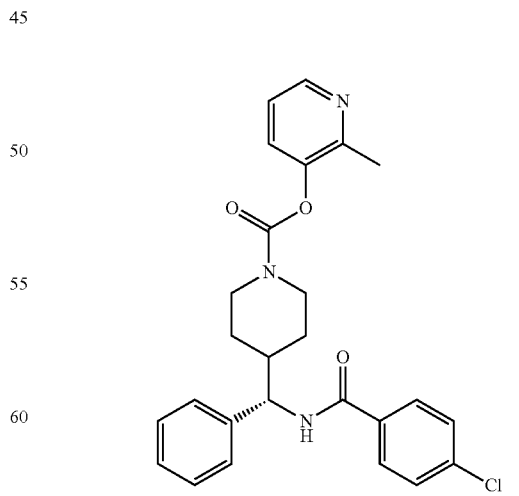

A mixture of 4-nitrophenyl (S)-4-((4-chlorobenzamido) (phenyl)methyl)piperidine-1-carboxylate (100 mg, 0.20 mmol), 2-methylpyridin-3-ol (88 mg, 0.81 mmol), $Cs_2CO_3$ (130 mg, 0.40 mmol) and DMSO (2.5 mL) was heated to 140° C. by microwave. After stirred at this temperature for 1 h, the reaction mixture was partitioned between EtOAc/H$_2$O, and the layers were separated. The organic layer was washed with brine and dried over Na$_2$SO$_4$. Solvent was removed under vacuum and the residue was purified by Gilson (C18, 10-50% MeCN in water with 0.1% formic acid) to afford the title compound (67 mg, 72%) as a white solid. $^1$H NMR (400 MHz, DMSO) δ 8.91 (d, J=8.7 Hz, 1H), 8.31 (dd, J=4.7, 1.3 Hz, 1H), 7.92-7.85 (m, 2H), 7.58-7.50 (m, 3H), 7.44 (d, J=7.3 Hz, 2H), 7.35 (t, J=7.5 Hz, 2H), 7.30-7.23 (m, 2H), 4.81 (t, J=8.9 Hz, 1H), 4.27-3.93 (m, 2H), 3.03-2.77 (m, 2H), 2.33 (s, 3H), 2.12-1.95 (m, 2H), 1.34-1.14 (m, 3H). LCMS (ESI) m/z calcd for C$_{26}$H$_{26}$ClN$_3$O$_3$: 463.17. Found: 464.30/466.24 (M/M+2)$^+$.

Example 20

Preparation of 2,3-dimethylpyridin-4-yl (S)-4-((4-chlorobenzamido)(phenyl)methyl) Piperidine-1-carboxylate

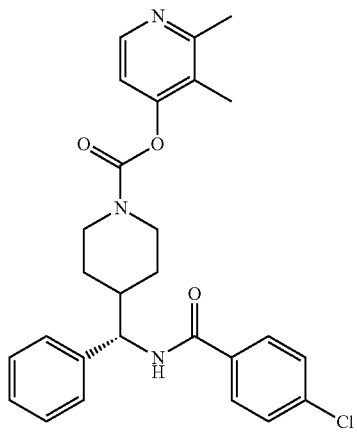 [SMILES: Cc1nccc(OC(=O)N2CCC([C@H](NC(=O)c3ccc(Cl)cc3)c3ccccc3)CC2)c1C]

A mixture of 4-nitrophenyl (S)-4-((4-chlorobenzamido)(phenyl)methyl)piperidine-1-carboxylate (100 mg, 0.20 mmol), 2,3-dimethylpyridin-4-ol (170 mg, 1.40 mmol), Cs$_2$CO$_3$ (130 mg, 0.40 mmol) and DMSO (2.5 mL) was heated to 140° C. by microwave. After stirred at this temperature for 1 h, the reaction mixture was partitioned between EtOAc/H$_2$O, and the layers were separated. The organic layer was washed with brine and dried over Na$_2$SO$_4$. Solvent was removed under vacuum and the residue was purified by Gilson (C18, 10-50% MeCN in water with 0.1% formic acid) to afford the title compound (73 mg, 77%) as a white solid. $^1$H NMR (400 MHz, DMSO) δ 8.90 (d, J=8.7 Hz, 1H), 8.24 (d, J=5.4 Hz, 1H), 7.88 (d, J=8.5 Hz, 2H), 7.54 (d, J=8.5 Hz, 2H), 7.47-7.39 (m, 2H), 7.39-7.31 (m, 2H), 7.28-7.21 (m, 1H), 7.02 (d, J=5.4 Hz, 1H), 4.81 (t, J=8.8 Hz, 1H), 4.24-3.93 (m, 2H), 3.03-2.79 (m, 2H), 2.46 (s, 3H), 2.11-1.94 (m, 5H), 1.36-1.15 (m, 3H). LCMS (ESI) m/z calcd for C$_{27}$H$_{28}$ClN$_3$O$_3$: 477.18. Found: 478.23/480.29 (M/M+2)$^+$.

Example 31

Preparation of 2-fluoropyridin-3-yl (S)-4-((4-chlorobenzamido)(phenyl)methyl) Piperidine-1-carboxylate

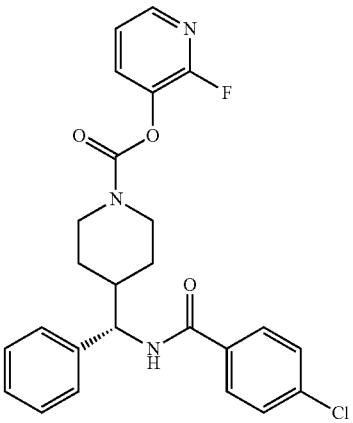 [SMILES: O=C(N[C@H](c1ccccc1)C1CCN(C(=O)Oc2cccnc2F)CC1)c1ccc(Cl)cc1]

A mixture of 4-nitrophenyl (S)-4-((4-chlorobenzamido)(phenyl)methyl)piperidine-1-carboxylate (200 mg, 0.40 mmol), 2-fluoropyridin-3-ol (180 mg, 1.59 mmol), Cs$_2$CO$_3$ (130 mg, 0.40 mmol) and DMSO (2.5 mL) was heated to 140° C. by microwave. After stirred at this temperature for 1 h, the reaction mixture was partitioned between EtOAc/H$_2$O, and the layers were separated. The organic layer was washed with brine and dried over Na$_2$SO$_4$. Solvent was removed under vacuum and the residue was purified by Gilson (C18, 10-50% MeCN in water with 0.1% formic acid) to afford the title compound (76 mg, 41%) as a white solid. $^1$H NMR (400 MHz, DMSO) δ 8.90 (d, J=8.7 Hz, 1H), 8.08 (d, J=4.6 Hz, 1H), 7.89 (d, J=8.5 Hz, 3H), 7.54 (d, J=8.5 Hz, 2H), 7.46-7.38 (m, 3H), 7.34 (t, J=7.5 Hz, 2H), 7.28-7.21 (m, 1H), 4.81 (t, J=9.1 Hz, 1H), 4.22-3.91 (m, 2H), 3.06-2.80 (m, 2H), 2.12-1.96 (m, 2H), 1.33-1.11 (m, 3H). LCMS (ESI) m/z calcd for C$_{25}$H$_{23}$ClFN$_3$O$_3$: 467.14. Found: 468.23/470.19 (M/M+2)$^+$.

Example 49

Preparation of 2-methoxypyridin-3-yl (S)-4-((4-chlorobenzamido)(phenyl)methyl) Piperidine-1-carboxylate

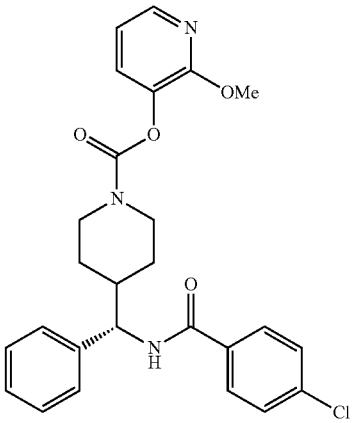 [SMILES: COc1ncccc1OC(=O)N1CCC([C@H](NC(=O)c2ccc(Cl)cc2)c2ccccc2)CC1]

A mixture of 4-nitrophenyl (S)-4-((4-chlorobenzamido)(phenyl)methyl)piperidine-1-carboxylate (100 mg, 0.20 mmol), 2-methoxypyridin-3-ol (100 mg, 0.80 mmol), Cs₂CO₃ (130 mg, 0.40 mmol) and DMSO (2.5 mL) was heated to 140° C. by microwave. After stirred at this temperature for 1 h, the reaction mixture was partitioned between EtOAc/H₂O, and the layers were separated. The organic layer was washed with brine and dried over Na₂SO₄. Solvent was removed under vacuum and the residue was purified by Gilson (C18, 10-50% MeCN in water with 0.1% formic acid) to afford the title compound (78 mg, 81%) as a white solid. ¹H NMR (400 MHz, DMSO) δ 8.90 (d, J=8.6 Hz, 1H), 8.01 (d, J=3.6 Hz, 1H), 7.89 (d, J=8.5 Hz, 2H), 7.61-7.48 (m, 3H), 7.47-7.40 (m, 2H), 7.34 (t, J=7.5 Hz, 2H), 7.28-7.22 (m, 1H), 7.03-6.97 (m, 1H), 4.81 (t, J=9.2 Hz, 1H), 4.20-3.93 (m, 2H), 3.85 (s, 3H), 3.00-2.78 (m, 2H), 2.13-1.95 (m, 2H), 1.34-1.13 (m, 3H). LCMS (ESI) m/z calcd for C₂₆H₂₆ClN₃O₄: 479.16. Found: 480.28/482.23 (M/M+2)⁺.

Example 1

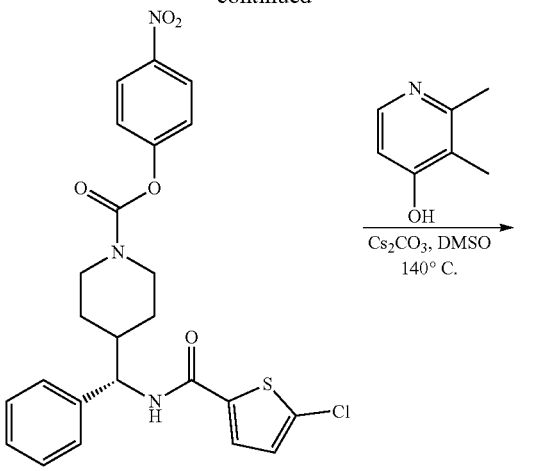

Preparation of Tert-butyl (S)-4-((5-chlorothiophene-2-carboxamido)(phenyl)methyl) Piperidine-1-carboxylate

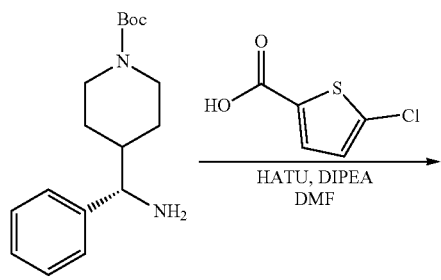

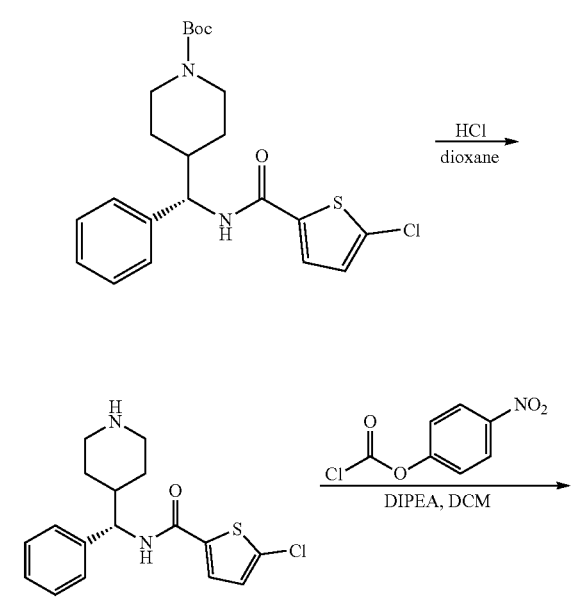

To a stirred solution of tert-butyl (S)-4-(amino(phenyl)methyl)piperidine-1-carboxylate (300 mg, 1.03 mmol) and 5-chlorothiophene-2-carboxylic acid (185 mg, 1.14 mmol) in DMF (4 mL) under was added DIPEA (0.8 mL, 5.17 mmol) followed by HATU (433 mg, 1.14 mmol). After stirred at r.t. overnight, the reaction mixture was quenched with brine and the resulting mixture was extracted with DCM. The combined organic layers were dried over Na₂SO₄. Solvent was removed under vacuum and the residue was purified by flash chromatography (silica gel, 0-25% ethyl acetate in petroleum ether) to afford the title compound (320 mg, 71% yield) as a pale solid. LCMS (ESI) m/z calcd for $C_{22}H_{27}ClN_2O_3S$: 434.14. Found: 435.21/435.17 (M/M+2)⁺.

Preparation of (S)-5-chloro-N-(phenyl(piperidin-4-yl)methyl)thiophene-2-carboxamide

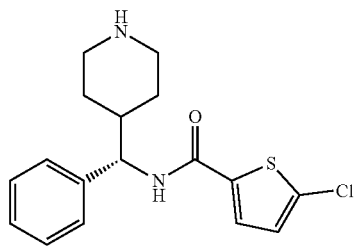 [SMILES: O=C(N[C@H](c1ccccc1)C1CCNCC1)c1ccc(Cl)s1]

To a solution of tert-butyl (S)-4-((5-chlorothiophene-2-carboxamido)(phenyl) methyl)piperidine-1-carboxylate (320 g, 0.74 mmol) in DCM (2.0 mL) was added 4 M HCl in dioxane (4 mL). After stirred at r.t. for 1 h, the reaction mixture was concentrated under vacuum to afford the title compound (280 mg, 100% yield) as a HCl salt, which was used in the following step directly. LCMS (ESI) m/z calcd for $C_{17}H_{19}ClN_2OS$: 334.09. Found: 335.15/337.13 (M/M+2)⁺.

Preparation of 4-nitrophenyl (S)-4-((5-chlorothiophene-2-carboxamido)(phenyl) Methyl)piperidine-1-carboxylate

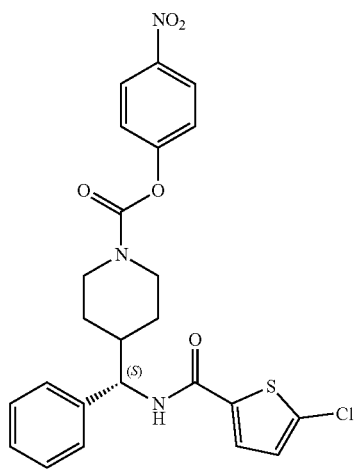

At 0° C., to a stirred solution of (S)-5-chloro-N-(phenyl (piperidin-4-yl)methyl)thiophene-2-carboxamide (280 g, 0.74 mmol) in DCM (4 mL) was added DIPEA (0.66 mL, 3.70 mmol) followed by 4-nitrophenyl carbonochloridate (224 mg, 1.11 mmol) drop wise. After stirred at r.t. for 2 h, the reaction mixture was partitioned between DCM/H₂O, and the layers were separated. The organic layer was washed with aq. NaHCO₃, brine and dried over Na₂SO₄. Solvent was removed under vacuum and the residue was purified by flash chromatography (silica gel, 0-30% ethyl acetate in petroleum ether) to afford the title compound (315 g, 85%)) as a pale solid. LCMS (ESI) m/z calcd for $C_{24}H_{22}ClN_3O_5S$: 499.10. Found: 500.24/502.30 (M/M+2)⁺.

Preparation of 2,3-dimethylpyridin-4-yl (S)-4-((5-chlorothiophene-2-carboxamido) (phenyl)methyl)piperidine-1-carboxylate

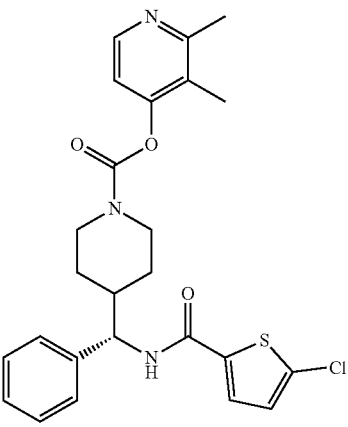 [SMILES: Cc1nccc(OC(=O)N2CCC([C@H](NC(=O)c3ccc(Cl)s3)c3ccccc3)CC2)c1C]

A mixture of 4-nitrophenyl (S)-4-((5-chlorothiophene-2-carboxamido)(phenyl) methyl)piperidine-1-carboxylate (110 mg, 0.22 mmol), 2,3-dimethylpyridin-3-ol (189 mg, 1.54 mmol), Cs₂CO₃ (143 mg, 0.44 mmol) and DMSO (2.5 mL) was heated to 140° C. by microwave. After stirred at this temperature for 1 h, the reaction mixture was partitioned between EtOAc/H₂O, and the layers were separated. The organic layer was washed with brine and dried over Na₂SO₄. Solvent was removed under vacuum and the residue was purified by Gilson (C18, 10-60% MeCN in water with 0.1% formic acid) to afford the title compound (41 mg, 39% yield) as a white solid. ¹H NMR (400 MHz, DMSO) δ 8.88 (d, J=8.6 Hz, 1H), 8.26 (d, J=5.5 Hz, 1H), 7.81 (d, J=4.0 Hz, 1H), 7.44-7.31 (m, 4H), 7.29-7.23 (m, 1H), 7.20 (d, J=4.0 Hz, 1H), 7.05 (d, J=5.4 Hz, 1H), 4.74 (t, J=9.2 Hz, 1H), 4.25-3.94 (m, 2H), 3.03-2.79 (m, 2H), 2.47 (s, 3H), 2.12-1.94 (m, 5H), 1.36-1.15 (m, 3H). LCMS (ESI) m/z calcd for $C_{25}H_{26}ClN_3O_3S$: 483.14. Found: 484.07/486.26 (M/M+2)⁺.

Example 42

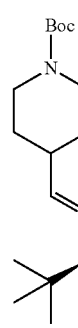 

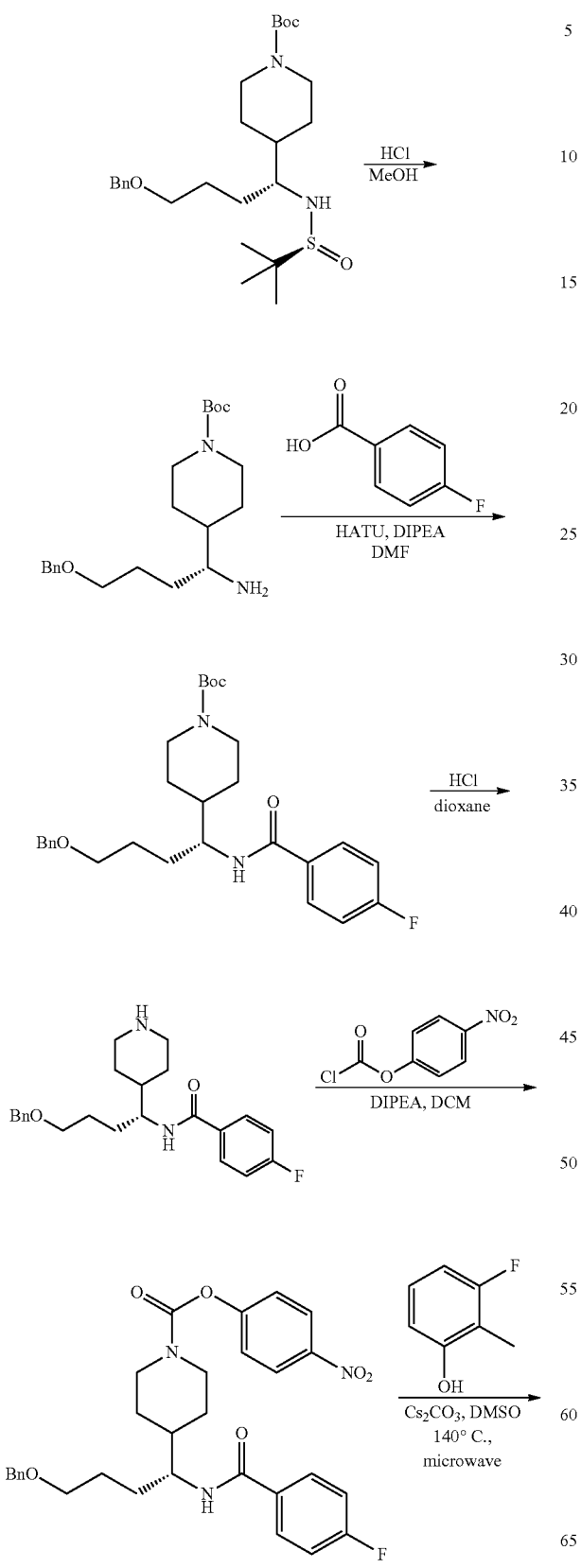
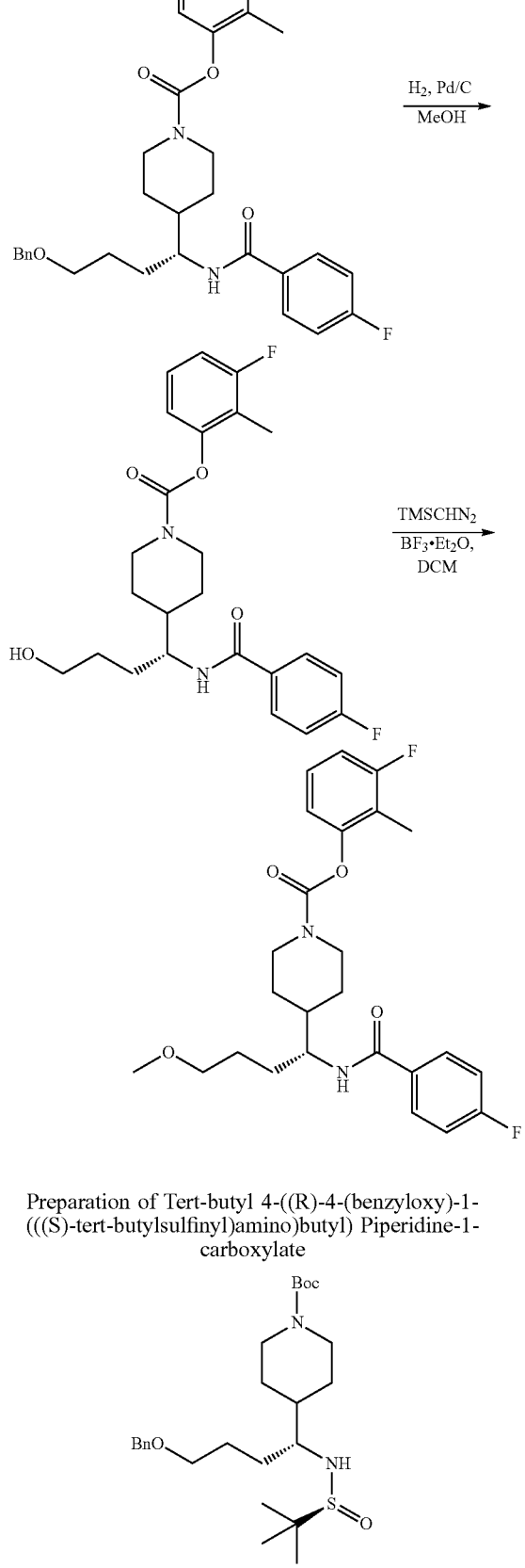
Preparation of Tert-butyl 4-((R)-4-(benzyloxy)-1-(((S)-tert-butylsulfinyl)amino)butyl) Piperidine-1-carboxylate To a mixture of magnesium chips (5.76 g, 237 mmol) and dry THF (100 mL) placed in a flame-dried flask under N₂, was added benzyl-3-bromopropyl ether (36.2 g, 158 mmol) dropwise. Then the resulting mixture was heated to reflux and stirred at this temperature for another 1 hour. At 0° C., to a solution of (S,E)-tert-butyl 4-{{tertbutylsulfinyiimino)methyl)piperidine-1-carboxylate (10 g, 31.6 mmol) in THF (150 mL) under nitrogen atmosphere, was added the above fresh prepared Grignard reagent drop wise and the reaction mixture was stirred for 2 h at this temperature. The reaction was carefully quenched via the addition of saturated aqueous NH₄Cl. The layers were separated and the aqueous phase was extracted with DCM. The combined organic layer was washed with brine, dried over Na₂SO₄, filtered and concentrated to give the crude product which was purified by flash chromatography (silica gel, 0-30% MeCN in DCM) to afford the title compound (4.1 g, 28% yield). LCMS (ESI) m/z calcd for $C_{25}H_{42}N_2O_4S$: 466.29. Found: 467.48 $(M+1)^+$.

Preparation of Tert-butyl (R)-4-(1-amino-4-(benzyloxy)butyl)piperidine-1-carboxylate

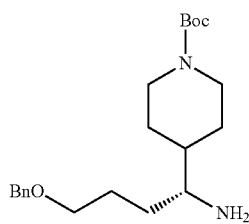 [SMILES: CC(C)(C)OC(=O)N1CCC([C@H](N)CCCOCc2ccccc2)CC1]

To tert-butyl 4-((R)-4-(benzyloxy)-1-(((S)-tert-butylsulfinyl)amino)butyl)piperidine-1-carboxylate (1.90 g, 4.06 mmol) was added 0.4 M HCl in MeOH (11.2 mL, 4.47 mmol). After stirred at r.t. for 1 h, LCMS showed the reaction was complete. The reaction mixture was quenched with saturated aq. NaHCO₃ and extracted with DCM (×3). The combined organic layers were washed with brine and dried over Na₂SO₄. Solvent was removed under vacuum to afford the title compound (1.3 g, 88%) as a viscous pale oil, which was used in the following step directly. LCMS (ESI) m/z calcd for $C_{21}H_{34}N_2O_3$: 362.26. Found: 363.92 $(M+1)^+$.

Preparation of Tert-butyl (R)-4-(4-(benzyloxy)-1-(4-fluorobenzamido)butyl) piperidine-1-carboxylate

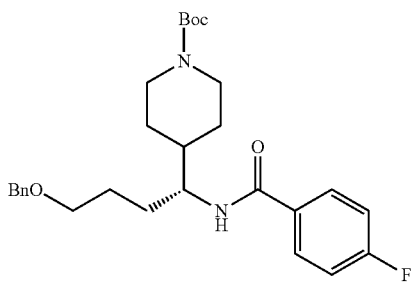 [SMILES: CC(C)(C)OC(=O)N1CCC([C@@H](CCCOCc2ccccc2)NC(=O)c2ccc(F)cc2)CC1]

To a stirred solution of tert-butyl (R)-4-(1-amino-4-(benzyloxy)butyl)piperidine-1-carboxylate (605 mg, 1.66 mmol) and 4-fluorobenzoic acid (256 mg, 1.83 mmol) in DMF (10 mL) under was added DIPEA (0.90 mL, 4.98 mmol) followed by HATU (696 mg, 1.83 mmol). After stirred at r.t. overnight, the reaction mixture was quenched with brine and the resulting mixture was extracted with DCM (×3). The combined organic layers were dried over Na₂SO₄. Solvent was removed under vacuum and the residue was purified by flash chromatography (silica gel, 0-40% ethyl acetate in petroleum ether) to afford the title compound (610 mg, 76%) as a pale solid. LCMS (ESI) m/z calcd for $C_{28}H_{37}FN_2O_4$: 484.27. Found: 485.41 $(M+1)^+$.

Preparation of (R)—N-(4-(benzyloxy)-1-(piperidin-4-yl)butyl)-4-fluorobenzamide

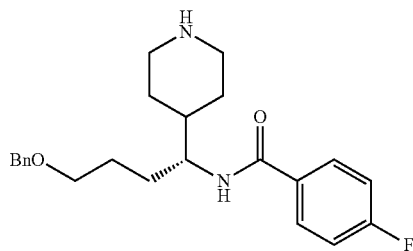 [SMILES: O=C(N[C@H](CCCOCc1ccccc1)C1CCNCC1)c1ccc(F)cc1]

To a solution of tert-butyl (R)-4-(4-(benzyloxy)-1-(4-fluorobenzamido)butyl)piperidine-1-carboxylate (610 mg, 1.26 mmol) in DCM (4.0 mL) was added 4 M HCl in dioxane (10 mL). After stirred at r.t. for 1 h, the reaction mixture was concentrated under vacuum to afford the title compound (550 mg, quantitative yield) as a HCl salt, which was used in the following step directly. LCMS (ESI) m/z calcd for $C_{23}H_{29}FN_2O_2$: 384.22. Found: 385.32 $(M+1)^+$.

Preparation of 4-nitrophenyl (R)-4-(4-(benzyloxy)-1-(4-fluorobenzamido)butyl) Piperidine-1-carboxylate

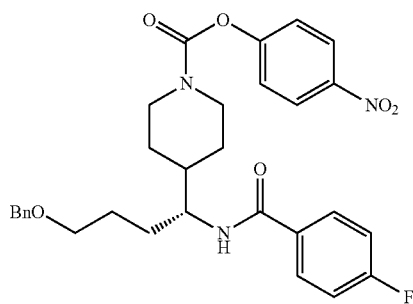 [SMILES: O=C(N[C@H](CCCOCc1ccccc1)C1CCN(C(=O)Oc2ccc([N+](=O)[O-])cc2)CC1)c1ccc(F)cc1]

At 0° C., to a stirred solution of (R)—N-(4-(benzyloxy)-1-(piperidin-4-yl)butyl)-4-fluorobenzamide (550 mg, 1.26 mmol) in DCM (11 mL) was added DIPEA (1.10 mL, 6.30 mmol) followed by adding 4-nitrophenyl carbonochloridate (305 mg, 1.51 mmol) drop wise. After stirred at r.t. for 2 h, the reaction mixture was partitioned between DCM/H₂O, and the layers were separated. The organic layer was washed with aq. NaHCO₃, brine and dried over Na₂SO₄. Solvent was removed under vacuum and the residue was purified by flash chromatography (silica gel, 0-30% ethyl acetate in petroleum ether) to afford the title compound (610 mg, 88%)) as a pale solid. LCMS (ESI) m/z calcd for $C_{30}H_{32}FN_3O_6$: 549.23. Found: 550.57 $(M+1)^+$.

Preparation of 3-fluoro-2-methylphenyl (R)-4-(4-(benzyloxy)-1-(4-fluorobenzamido) butyl)piperidine-1-carboxylate

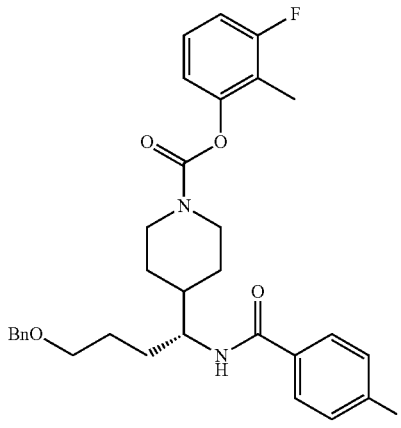

A mixture of 4-nitrophenyl (R)-4-(4-(benzyloxy)-1-(4-fluorobenzamido)butyl)piperidine-1-carboxylate (400 mg, 0.73 mmol), 3-fluoro-2-methylphenol (367 mg, 2.91 mmol), $Cs_2CO_3$ (948 mg, 2.91 mmol) and DMSO (6 mL) was heated to 140° C. by microwave. After stirred at this temperature for 1 h, the reaction mixture was partitioned between EtOAc/$H_2O$, and the layers were separated. The organic layer was washed with brine and dried over $Na_2SO_4$. Solvent was removed under vacuum and the residue was purified by chromatography on silica gel to afford the title compound (310 mg, 79%). LCMS (ESI) m/z calcd for $C_{31}H_{34}F_2N_2O_4$: 536.25. Found: 537.41 $(M+1)^+$.

Preparation of 3-fluoro-2-methylphenyl (R)-4-(1-(4-fluorobenzamido)-4-hydroxy butyl)piperidine-1-carboxylate

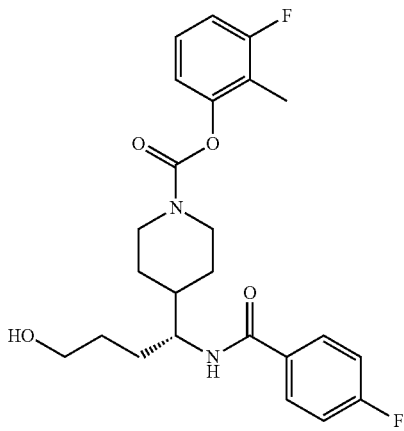 [SMILES: Cc1c(F)cccc1OC(=O)N1CCC([C@@H](CCCO)NC(=O)c2ccc(F)cc2)CC1]

A mixture of 3-fluoro-2-methylphenyl (R)-4-(4-(benzyloxy)-1-(4-fluorobenzamido) butyl)piperidine-1-carboxylate (336 mg, 0.626 mmol) and 10% Pd/C (168 mg) in MeOH (3 mL) was stirred at room temperature under $H_2$ atmosphere (15 psi) overnight. The resulting mixture was filtered through a pad of Celite and the filtrate was concentrated under reduced pressure to give a residue, which was purified by chromatography on silica gel to afford the title compound (144 mg, 52% yield). $^1H$ NMR (400 MHz, DMSO) δ 8.12 (d, J=8.8 Hz, 1H), 7.97-7.90 (m, 2H), 7.30 (t, J=8.9 Hz, 2H), 7.26-7.19 (m, 1H), 7.05 (t, J=8.8 Hz, 1H), 6.93 (d, J=8.1 Hz, 1H), 4.38 (t, J=5.1 Hz, 1H), 4.26-4.15 (m, 1H), 4.08-3.97 (m, 1H), 3.92-3.84 (m, 1H), 3.43-3.35 (m, 2H), 3.07-2.94 (m, 1H), 2.89-2.75 (m, 1H), 2.00 (s, 3H), 1.82-1.68 (m, 3H), 1.67-1.58 (m, 1H), 1.55-1.44 (m, 2H), 1.43-1.35 (m, 1H), 1.31-1.15 (m, 2H). (ESI) m/z calcd for $C_{24}H_{28}F_2N_2O_4$: 446.20. Found: 447.64 $(M+1)^+$.

Preparation of 3-fluoro-2-methylphenyl (R)-4-(1-(4-fluorobenzamido)-4-methoxy butyl)piperidine-1-carboxylate

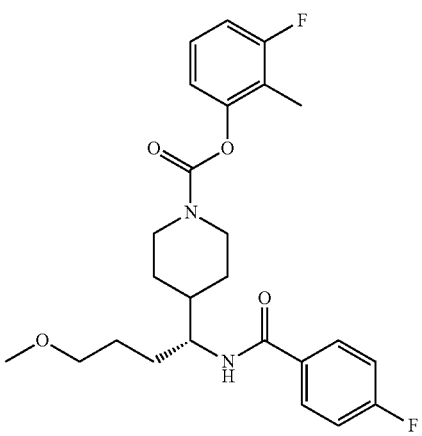 [SMILES: COCCC[C@@H](NC(=O)c1ccc(F)cc1)C1CCN(C(=O)Oc2cccc(F)c2C)CC1]

At room temperature, to a mixture of 3-fluoro-2-methylphenyl (R)-4-(1-(4-fluorobenzamido)-4-hydroxy butyl)piperidine-1-carboxylate (140 mg, 0.313 mmol), 2 drops of $BF_3.Et_2O$ and DCM (2 mL) with a vigorously stirring bar, $TMSCHN_2$ in diethyl ether (0.78 mL, 1.56 mmol) was added by a syringe pump over 30 min. The resulting mixture was concentrated under reduced pressure to give a residue, which was further purified by Prep. HPLC to afford the title compound (26 mg, 18% yield) as a white solid. $^1H$ NMR (400 MHz, DMSO) δ 8.13 (d, J=9.0 Hz, 1H), 7.99-7.87 (m, 2H), 7.30 (t, J=8.9 Hz, 2H), 7.26-7.17 (m, 1H), 7.05 (t, J=8.7 Hz, 1H), 6.93 (d, J=8.1 Hz, 1H), 4.26-4.15 (m, 1H), 4.08-3.97 (m, 1H), 3.92-3.84 (m, 1H), 3.31-3.27 (m, 2H), 3.20 (s, 3H), 3.05-2.94 (m, 1H), 2.88-2.77 (m, 1H), 2.00 (s, 3H), 1.81-1.68 (m, 3H), 1.67-1.60 (m, 1H), 1.58-1.42 (m, 3H), 1.30-1.15 (m, 2H). (ESI) m/z calcd for $C_{25}H_{30}F_2N_2O_4$: 460.22. Found: 461.27 $(M+1)^+$.

PBMC IDO1 Assay

PBMC IDOi Assay:

Data shown in Table 2. Compounds of the present invention were tested via high-throughput cellular assays utilizing detection of kynurenine via mass spectrometry and cytotoxicity as end-points. For the mass spectrometry and cytotoxicity assays, human peripheral blood mononuclear cells (PBMC) (PB003F; AllCells®, Alameda, Calif.) were stimulated with human interferon-γ (IFN-γ) (Sigma-Aldrich Corporation, St. Louis, Mo.) and lipopolysaccharide from *Salmonella minnesota* (LPS) (Invivogen, San Diego, Calif.) to induce the expression of indoleamine 2, 3-dioxygenase (IDO1). Compounds with IDO1 inhibitory properties decreased the amount of kynurenine produced by the cells via the tryptophan catabolic pathway. Cellular toxicity due to the effect of compound treatment was measured using CellTiter-Glo® reagent (CTG) (Promega Corporation, Madison, Wis.), which is based on luminescent detection of ATP, an indicator of metabolically active cells.

In preparation for the assays, test compounds were serially diluted 3-fold in DMSO from a typical top concentration of 5 mM and plated at 0.5 µL in 384-well, polystyrene, clear bottom, tissue culture treated plates with lids (Greiner Bio-One, Kremsmünster, Austria) to generate 11-point dose response curves. Low control wells (0% kynurenine or 100% cytotoxicity) contained either 0.5 µL of DMSO in the presence of unstimulated (-IFN-γ/-LPS) PBMCs for the mass spectrometry assay or 0.5 µL of DMSO in the absence of cells for the cytotoxicity assay, and high control wells (100% kynurenine or 0% cytotoxicity) contained 0.5 µL of DMSO in the presence of stimulated (+IFN-γ/+LPS) PBMCs for both the mass spectrometry and cytotoxicity assays.

Frozen stocks of PBMCs were washed and recovered in RPMI 1640 medium (Thermo Fisher Scientific, Inc., Waltham, Mass.) supplemented with 10% v/v heat-inactivated fetal bovine serum (FBS) (Thermo Fisher Scientific, Inc., Waltham, Mass.), and 1× penicillin-streptomycin antibiotic solution (Thermo Fisher Scientific, Inc., Waltham, Mass.). The cells were diluted to 1,000,000 cells/mL in the supplemented RPMI 1640 medium. 50 µL of either the cell suspension, for the mass spectrometry assay, or medium alone, for the cytotoxicity assay, were added to the low control wells, on the previously prepared 384-well compound plates, resulting in 50,000 cells/well or 0 cells/well respectively. IFN-γ and LPS were added to the remaining cell suspension at final concentrations of 100 ng/ml and 50 ng/ml respectively, and 50 µL of the stimulated cells were added to all remaining wells on the 384-well compound plates. The plates, with lids, were then placed in a 37° C., 5% $CO_2$ humidified incubator for 2 days.

Following incubation, the 384-well plates were removed from the incubator and allowed to equilibrate to room temperature for 30 minutes. For the cytotoxicity assay, CellTiter-Glo® was prepared according to the manufacturer's instructions, and 40 µL were added to each plate well. After a twenty minute incubation at room temperature, luminescence was read on an EnVision® Multilabel Reader (PerkinElmer Inc., Waltham, Mass.). For the mass spectrometry assay, 10 µL of supernatant from each well of the compound-treated plates were added to 40 µL of acetonitrile, containing 10 µM of an internal standard for normalization, in 384-well, polypropylene, V-bottom plates (Greiner Bio-One, Kremsmünster, Austria) to extract the organic analytes. Following centrifugation at 2000 rpm for 10 minutes, 10 µL from each well of the acetonitrile extraction plates were added to 90 µL of sterile, distilled $H_2O$ in 384-well, polypropylene, V-bottom plates for analysis of kynurenine and the internal standard on the RapidFire 300 (Agilent Technologies, Santa Clara, Calif.) and 4000 QTRAP MS (SCIEX, Framingham, Mass.). MS data were integrated using Agilent Technologies' RapidFire Integrator software, and data were normalized for analysis as a ratio of kynurenine to the internal standard.

The data for dose responses in the mass spectrometry assay were plotted as % IDO1 inhibition versus compound concentration following normalization using the formula $100-(100*((U-C2)/(C1-C2)))$, where U was the unknown value, C1 was the average of the high (100% kynurenine; 0% inhibition) control wells and C2 was the average of the low (0% kynurenine; 100% inhibition) control wells. The data for dose responses in the cytotoxicity assay were plotted as % cytotoxicity versus compound concentration following normalization using the formula $100-(100*((U-C2)/(C1-C2)))$, where U was the unknown value, C1 was the average of the high (0% cytotoxicity) control wells and C2 was the average of the low (100% cytotoxicity) control wells.

Curve fitting was performed with the equation $y=A+((B-A)/(1+(10^x/10^C)^D))$, where A was the minimum response, B was the maximum response, C was the $\log(XC_{50})$ and D was the Hill slope. The results for each test compound were recorded as pIC50 values for the mass spectrometry assay and as pCC50 values for the cytoxicity assay (−C in the above equation).

Although the invention has been shown and described above with reference to some embodiments, those skilled in the art will readily appreciate that the specific experiments detailed are only illustrative of the invention. It should be understood that various modifications can be made without departing from the spirit of the invention.

For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims. Accordingly, the invention is limited only by the following claims. All publications, issued patents, patent applications, books and journal articles, cited in this application are each herein incorporated by reference in their entirety.

TABLE 2

| Example | Name | PBMC PXC50_ |
|---|---|---|
| 1 | (S)-2,3-dimethylpyridin-4-yl 4-((5-chlorothiophene-2-carboxamido)(phenyl)methyl)piperidine-1-carboxylate | 9.2 |
| 2 | 2-methylpyridin-3-yl 4-(3-methyl-1-(5-methylthiophene-2-carboxamido)butyl)piperidine-1-carboxylate | 9 |
| 3 | 2,4-dimethylpyridin-3-yl 4-(1-(4-chlorobenzamido)-3-methylbutyl)piperidine-1-carboxylate | 9 |
| 4 | 2-methylpyridin-3-yl 4-{1-[(5-chlorothiophen-2-yl)formamido]-3-methylbutyl}piperidine-1-carboxylate | 8.9 |
| 5 | 2-cyanopyridin-3-yl 4-{1-[(4-chlorophenyl)formamido]-3-methylbutyl}piperidine-1-carboxylate | 8.8 |
| 6 | 2-methylpyridin-3-yl 4-{1-[(4-chlorophenyl)formamido]-3-methylbutyl}piperidine-1-carboxylate | 8.8 |
| 7 | 2,3-dimethylpyridin-4-yl 4-[(R)-[(5-chlorothiophen-2-yl)formamido](cyclopropyl)methyl]piperidine-1-carboxylate | 8.7 |
| 8 | phenyl 4-[(1R)-1-[(5-chlorothiophen-2-yl)formamido]-3-methylbutyl]piperidine-1-carboxylate | 8.7 |
| 9 | 3-fluoro-2-methylphenyl 4-{1-[(4-fluorophenyl)formamido]-3-methylbutyl}piperidine-1-carboxylate | 8.6 |
| 10 | 2-methoxypyridin-3-yl 4-{1-[(4-chlorophenyl)formamido]-3-methylbutyl}piperidine-1-carboxylate | 8.6 |
| 11 | 2-chloro-3-fluorophenyl 4-{1-[(4-fluorophenyl)formamido]-3-methylbutyl}piperidine-1-carboxylate | 8.6 |
| 12 | 2-cyano-3-fluorophenyl 4-{1-[(4-fluorophenyl)formamido]-3-methylbutyl}piperidine-1-carboxylate | 8.6 |
| 13 | 3-fluoro-2-methoxyphenyl 4-{1-[(4-fluorophenyl)formamido]-3-methylbutyl}piperidine-1-carboxylate | 8.6 |

TABLE 2-continued

| Example | Name | PBMC PXC50_ |
|---|---|---|
| 14 | 2-methylpyridin-3-yl 4-[(S)-[(4-chlorophenyl)formamido](phenyl)methyl]piperidine-1-carboxylate | 8.6 |
| 15 | 4,6-dimethylpyrimidin-5-yl 4-{1-[(4-chlorophenyl)formamido]-3-methylbutyl}piperidine-1-carboxylate | 8.6 |
| 16 | phenyl 4-{1-[(5-chlorothiophen-2-yl)formamido]-3-methylbutyl}piperidine-1-carboxylate | 8.5 |
| 17 | 2-methylpyridin-3-yl 4-[(R)-[(5-chlorothiophen-2-yl)formamido](cyclopropyl)methyl]piperidine-1-carboxylate | 8.5 |
| 18 | 2-methylpyridin-3-yl 4-{1-[(4-fluorophenyl)formamido]-3-methylbutyl}piperidine-1-carboxylate | 8.5 |
| 19 | 3-fluoro-2-methylphenyl 4-[(R)-[(5-chlorothiophen-2-yl)formamido](cyclopropyl)methyl]piperidine-1-carboxylate | 8.5 |
| 20 | 2,3-dimethylpyridin-4-yl 4-[(S)-[(4-chlorophenyl)formamido](phenyl)methyl]piperidine-1-carboxylate | 8.4 |
| 21 | phenyl 4-[(1R)-1-[(4-chlorophenyl)formamido]-3-methylbutyl]piperidine-1-carboxylate | 8.4 |
| 22 | 2-fluoropyridin-3-yl 4-{1-[(4-fluorophenyl)formamido]-3-methylbutyl}piperidine-1-carboxylate | 8.4 |
| 23 | phenyl 4-[(R)-[(5-chlorothiophen-2-yl)formamido](cyclopropyl)methyl]piperidine-1-carboxylate | 8.4 |
| 24 | 2-methylpyridin-3-yl 4-[(R)-cyclopropyl[(5-methylthiophen-2-yl)formamido]methyl]piperidine-1-carboxylate | 8.4 |
| 25 | phenyl 4-[(1R)-3-methyl-1-(phenylformamido)butyl]piperidine-1-carboxylate | 8.3 |
| 26 | phenyl 4-{1-[(4-chlorophenyl)formamido]-3-methylbutyl}piperidine-1-carboxylate | 8.3 |
| 27 | phenyl 4-[(1R)-1-[(4-fluorophenyl)formamido]-3-methylbutyl]piperidine-1-carboxylate | 8.3 |
| 28 | 2-fluoro-3-methylphenyl 4-{1-[(4-fluorophenyl)formamido]-3-methylbutyl}piperidine-1-carboxylate | 8.3 |
| 29 | 3-methylpyridin-4-yl 4-{1-[(4-chlorophenyl)formamido]-3-methylbutyl}piperidine-1-carboxylate | 8.3 |
| 30 | 2-methoxypyridin-3-yl 4-{1-[(4-fluorophenyl)formamido]-3-methylbutyl}piperidine-1-carboxylate | 8.3 |
| 31 | 2-fluoropyridin-3-yl 4-[(S)-[(4-chlorophenyl)formamido](phenyl)methyl]piperidine-1-carboxylate | 8.3 |
| 32 | 2,3-dimethylpyridin-4-yl 4-[(R)-cyclopropyl[(5-methylthiophen-2-yl)formamido]methyl]piperidine-1-carboxylate | 8.3 |
| 33 | 2-fluoro-3-methylpyridin-4-yl 4-{1-[(4-fluorophenyl)formamido]-3-methylbutyl}piperidine-1-carboxylate | 8.2 |
| 34 | 2-(propan-2-yl)pyridin-3-yl 4-{1-[(4-chlorophenyl)formamido]-3-methylbutyl}piperidine-1-carboxylate | 8.2 |
| 35 | 2,3-dimethylpyridin-4-yl 4-{1-[(4-chlorophenyl)formamido]-3-methylbutyl}piperidine-1-carboxylate | 8.2 |
| 36 | 3-fluoro-2-methylphenyl 4-[(1R)-1-[(5-chlorothiophen-2-yl)formamido]ethyl]piperidine-1-carboxylate | 8.2 |
| 37 | phenyl 4-{1-[(4-fluorophenyl)formamido]-3-methylbutyl}piperidine-1-carboxylate | 8.1 |
| 38 | phenyl 4-[(1R)-1-[(5-chlorothiophen-2-yl)formamido]ethyl]piperidine-1-carboxylate | 8.1 |
| 39 | phenyl 4-[3-methyl-1-(phenylformamido)butyl]piperidine-1-carboxylate | 8.1 |
| 40 | 2,3-dimethylphenyl 4-{1-[(4-fluorophenyl)formamido]-3-methylbutyl}piperidine-1-carboxylate | 8.1 |
| 41 | 3-cyano-2-fluorophenyl 4-{1-[(4-fluorophenyl)formamido]-3-methylbutyl}piperidine-1-carboxylate | 8.1 |
| 42 | 3-fluoro-2-methylphenyl 4-[(1R)-1-[(4-fluorophenyl)formamido]-4-methoxybutyl]piperidine-1-carboxylate | 8.1 |
| 43 | phenyl 4-[phenyl(phenylformamido)methyl]piperidine-1-carboxylate | 8 |
| 44 | 2,3-dimethylpyridin-4-yl 4-{1-[(4-fluorophenyl)formamido]-3-methylbutyl}piperidine-1-carboxylate | 8 |
| 45 | 5-fluoropyridin-3-yl 4-{1-[(4-fluorophenyl)formamido]-3-methylbutyl}piperidine-1-carboxylate | 8 |
| 46 | phenyl 4-{[(5-chlorothiophen-2-yl)formamido](cyclopropyl)methyl}piperidine-1-carboxylate | 8 |
| 47 | 3-fluoropyridin-4-yl 4-{1-[(4-fluorophenyl)formamido]-3-methylbutyl}piperidine-1-carboxylate | 8 |
| 48 | 2,3-difluoropyridin-4-yl 4-{1-[(4-fluorophenyl)formamido]-3-methylbutyl}piperidine-1-carboxylate | 8 |
| 49 | 2-methoxypyridin-3-yl 4-[(S)-[(4-chlorophenyl)formamido](phenyl)methyl]piperidine-1-carboxylate | 8 |
| 50 | 4-fluorophenyl 4-{1-[(4-fluorophenyl)formamido]-3-methylbutyl}piperidine-1-carboxylate | 7.9 |
| 51 | 3-fluoro-2-methylpyridin-4-yl 4-{1-[(4-fluorophenyl)formamido]-3-methylbutyl}piperidine-1-carboxylate | 7.9 |
| 52 | phenyl 4-{1-[(5-chlorothiophen-2-yl)formamido]ethyl}piperidine-1-carboxylate | 7.8 |
| 53 | phenyl 4-{[(4-chloro-3-fluorophenyl)formamido](phenyl)methyl}piperidine-1-carboxylate | 7.7 |
| 54 | 3-methoxyphenyl 4-{1-[(4-fluorophenyl)formamido]-3-methylbutyl}piperidine-1-carboxylate | 7.7 |
| 55 | 2-fluoropyridin-4-yl 4-{1-[(4-fluorophenyl)formamido]-3-methylbutyl}piperidine-1-carboxylate | 7.7 |
| 56 | 3-fluoro-2-methylphenyl 4-[(1R)-1-(phenylformamido)ethyl]piperidine-1-carboxylate | 7.6 |
| 57 | phenyl 4-{[(3-fluoro-4-methoxyphenyl)formamido](phenyl)methyl}piperidine-1-carboxylate | 7.4 |
| 58 | phenyl 4-[(1S)-1-[(5-chlorothiophen-2-yl)formamido]-3-methylbutyl]piperidine-1-carboxylate | 7.4 |
| 59 | 4-chlorophenyl 4-{1-[(4-fluorophenyl)formamido]-3-methylbutyl}piperidine-1-carboxylate | 7.3 |
| 60 | 3-fluoro-2-methoxypyridin-4-yl 4-{1-[(4-fluorophenyl)formamido]-3-methylbutyl}piperidine-1-carboxylate | 7.3 |
| 61 | 3-fluoro-2-methylphenyl 4-{cyclopropyl[(4-fluorophenyl)formamido]methyl}piperidine-1-carboxylate | 7.2 |
| 62 | benzyl 4-{1-[(4-fluorophenyl)formamido]-3-methylbutyl}piperidine-1-carboxylate | 7.2 |
| 63 | 2-methylpyridin-3-yl 4-{1-[(4-bromophenyl)formamido]ethyl}piperidine-1-carboxylate | 7.1 |
| 64 | (1,3-thiazol-2-yl)methyl 4-{1-[(4-chlorophenyl)formamido]-3-methylbutyl}piperidine-1-carboxylate | 7.1 |
| 65 | phenyl 4-{[(4-fluorophenyl)formamido](pyridin-4-yl)methyl}piperidine-1-carboxylate | 7 |
| 66 | phenyl 4-{cyclopropyl[(4-fluorophenyl)formamido]methyl}piperidine-1-carboxylate | 7 |
| 67 | phenyl 4-[(1S)-1-[(4-chlorophenyl)formamido]-3-methylbutyl]piperidine-1-carboxylate | 7 |
| 68 | 3-fluoro-2-methylphenyl 4-[(1R)-1-[(4-chlorophenyl)formamido]ethyl]piperidine-1-carboxylate | 6.9 |
| 69 | phenyl 4-[(1S)-1-[(4-fluorophenyl)formamido]-3-methylbutyl]piperidine-1-carboxylate | 6.9 |
| 70 | 2-fluoropyridin-3-yl 4-{1-[(4-bromophenyl)formamido]ethyl}piperidine-1-carboxylate | 6.9 |
| 71 | 2-fluoropyridin-4-yl 4-{cyclopropyl[(4-fluorophenyl)formamido]methyl}piperidine-1-carboxylate | 6.8 |
| 72 | 2-fluoropyridin-3-yl 4-{[(4-fluorophenyl)formamido](pyridin-4-yl)methyl}piperidine-1-carboxylate | 6.8 |

TABLE 2-continued

| Example | Name | PBMC PXC50_ |
|---|---|---|
| 73 | phenyl 4-[phenyl({[4-(trifluoromethyl)phenyl]formamido})methyl]piperidine-1-carboxylate | 6.8 |
| 74 | phenyl 4-{1-[(4-fluorophenyl)formamido]ethyl}piperidine-1-carboxylate | 6.8 |
| 75 | phenyl 4-[(1S)-3-methyl-1-(phenylformamido)butyl]piperidine-1-carboxylate | 6.8 |
| 76 | 2-fluoropyridin-3-yl 4-[(1R)-1-[(4-fluorophenyl)formamido]-4-methoxybutyl]piperidine-1-carboxylate | 6.8 |
| 77 | phenyl 4-[(phenylformamido)(pyridin-4-yl)methyl]piperidine-1-carboxylate | 6.7 |
| 78 | tert-butyl 4-{[(4-ethynylphenyl)formamido](phenyl)methyl}piperidine-1-carboxylate | 6.6 |
| 79 | quinolin-4-yl 4-{1-[(4-fluorophenyl)formamido]-3-methylbutyl}piperidine-1-carboxylate | 6.5 |
| 80 | 3-fluoro-2-methylphenyl 4-[(1R)-1-[(4-fluorophenyl)formamido]-4-hydroxybutyl]piperidine-1-carboxylate | 6.5 |
| 81 | pyridin-4-yl 4-{cyclopropyl[(4-fluorophenyl)formamido]methyl}piperidine-1-carboxylate | 6.4 |
| 82 | phenyl 4-{1-[(4-fluorophenyl)formamido]-2-(propan-2-yloxy)ethyl}piperidine-1-carboxylate | 6.4 |
| 83 | phenyl 4-{1-[(5-chloro-1,3,4-thiadiazol-2-yl)formamido]-3-methylbutyl}piperidine-1-carboxylate | 6.3 |
| 84 | 1,2,3,4-tetrahydroquinolin-4-yl 4-{1-[(4-fluorophenyl)formamido]-3-methylbutyl}piperidine-1-carboxylate | 6.3 |
| 85 | tert-butyl 4-{[(1H-indol-7-yl)formamido](phenyl)methyl}piperidine-1-carboxylate | 6.2 |
| 86 | 2-methoxypyridin-4-yl 4-{cyclopropyl[(4-fluorophenyl)formamido]methyl}piperidine-1-carboxylate | 6.2 |
| 87 | pyridin-3-yl 4-{[(4-fluorophenyl)formamido](pyridin-4-yl)methyl}piperidine-1-carboxylate | 6.2 |
| 88 | phenyl 4-[phenyl({[5-(trifluoromethyl)pyridin-2-yl]formamido})methyl]piperidine-1-carboxylate | 6.2 |
| 89 | phenyl 4-{[(5-cyanopyridin-2-yl)formamido](phenyl)methyl}piperidine-1-carboxylate | 6.2 |
| 90 | pyridin-3-yl 4-{cyclopropyl[(4-fluorophenyl)formamido]methyl}piperidine-1-carboxylate | 6.2 |
| 91 | phenyl 4-[(S)-[(5-chlorothiophen-2-yl)formamido](cyclopropyl)methyl]piperidine-1-carboxylate | 6.2 |
| 92 | 3-fluoro-2-methylphenyl 4-[(1S)-1-[(5-chlorothiophen-2-yl)formamido]ethyl]piperidine-1-carboxylate | 6.2 |
| 93 | 2-methoxypyridin-4-yl 4-{[(4-fluorophenyl)formamido](pyridin-4-yl)methyl}piperidine-1-carboxylate | 6.1 |
| 94 | pyridin-4-yl 4-{[(4-fluorophenyl)formamido](pyridin-4-yl)methyl}piperidine-1-carboxylate | 6 |
| 95 | phenyl 4-[(1S)-1-[(5-chlorothiophen-2-yl)formamido]ethyl]piperidine-1-carboxylate | 6 |
| 96 | pyridin-2-yl 4-{[(4-fluorophenyl)formamido](pyridin-4-yl)methyl}piperidine-1-carboxylate | 5.9 |
| 97 | 2-fluoropyridin-3-yl 4-[(1R)-1-[(4-fluorophenyl)formamido]-4-hydroxybutyl]piperidine-1-carboxylate | 5.9 |
| 98 | tert-butyl 4-[phenyl(phenylformamido)methyl]piperidine-1-carboxylate | 5.8 |
| 99 | 6-methoxypyridin-3-yl 4-{[(4-fluorophenyl)formamido](pyridin-4-yl)methyl}piperidine-1-carboxylate | 5.6 |
| 100 | cyclohexyl 4-{[(4-fluorophenyl)formamido](pyridin-4-yl)methyl}piperidine-1-carboxylate | 5.5 |
| 101 | 2-fluoro-3-methylpyridin-4-yl 4-[(1R)-1-[(5-chlorothiophen-2-yl)formamido]ethyl]piperidine-1-carboxylate | 5.5 |
| 102 | tert-butyl 4-{phenyl[(pyridin-3-yl)formamido]methyl}piperidine-1-carboxylate | 5.3 |
| 103 | phenyl 4-{[(5-carbamoylpyridin-2-yl)formamido](phenyl)methyl}piperidine-1-carboxylate | 5 |
| 104 | (R)-2-methylpyridin-3-yl 4-(1-(4-chlorobenzamido)-3-methylbutyl)piperidine-1-carboxylate | 8.9 |
| 105 | (R)-2-methoxypyridin-3-yl 4-(1-(4-fluorobenzamido)-3-methylbutyl)piperidine-1-carboxylate | 8.9 |
| 106 | (R)-3-fluoro-2-methoxyphenyl 4-(1-(4-fluorobenzamido)-3-methylbutyl)piperidine-1-carboxylate | 8.8 |
| 107 | (R)-4,6-dimethylpyrimidin-5-yl 4-(1-(4-chlorobenzamido)-3-methylbutyl)piperidine-1-carboxylate | 8.8 |
| 108 | 1H-indazol-7-yl 4-(1-(4-chlorobenzamido)-3-methylbutyl)piperidine-1-carboxylate | 9.3 |
| 109 | (R)-phenyl 4-(1-(1H-indazole-7-carboxamido)-3-methylbutyl)piperidine-1-carboxylate | 8.2 |
| 110 | phenyl 4-(1-(1H-indazole-7-carboxamido)-3-methylbutyl)piperidine-1-carboxylate | 7.9 |
| 111 | (S)-phenyl 4-((4-chlorobenzamido)(6-methoxypyridin-3-yl)methyl)piperidine-1-carboxylate | 7.2 |
| 112 | (S)-4,6-dimethylpyrimidin-5-yl 4-((5-chlorothiophene-2-carboxamido)(cyclopropyl)methyl)piperidine-1-carboxylate | 8.0 |
| 113 | (S)-4,6-dimethylpyrimidin-5-yl 4-(cyclopropyl(5-methylthiophene-2-carboxamido)methyl)piperidine-1-carboxylate | 7.9 |
| 114 | (S)-2,4-dimethylpyridin-3-yl 4-((5-chlorothiophene-2-carboxamido)(cyclopropyl)methyl)piperidine-1-carboxylate | 8.8 |
| 115 | (S)-pyrimidin-5-yl 4-((5-chlorothiophene-2-carboxamido)(cyclopropyl)methyl)piperidine-1-carboxylate | 7.3 |

What is claimed is:

1. A compound of Formula I

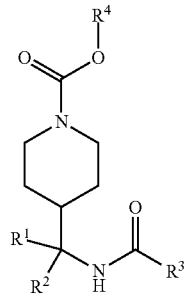

Formula I or a pharmaceutically acceptable salt thereof wherein:
one of $R^1$ and $R^2$ is H and the other is $C_{1-6}$alkyl, $C_{3-6}$ cycloalkyl, $C_{1-3}$ alkyl-O—$C_{1-4}$ alkylene-, HO—$C_{1-4}$ alkylene, $C_{6-9}$ aryl, 5-9 membered heteroaryl, or $R^1$ and $R^2$ together with the carbon to which they are bonded form a 3-6 membered cycloalkyl; and wherein $R^1$ and $R^2$ may optionally be substituted with 1 or 2 substituents selected from H, $C_{1-4}$alkyl, halogen, —O$C_{1-4}$alkyl, —COOH, NH—$C_{1-4}$alkyl, —$NH_2$, and OH;

$R^3$ is $C_{5-9}$aryl or 5 to 9 membered heteroaryl; and wherein $R^3$ may optionally be substituted with 1-3 substituents independently selected from halogen, $C_{1-3}$alkyl, $C_{1-3}$haloalkyl, —O$C_{1-3}$alkyl, $C_{2-4}$alkenyl, $C_{2-4}$alkynyl CN, and —$C(O)NH_2$;

and wherein each aryl and each heteroaryl includes bicycles and each heteroaryl contains from 1 to 3 heteroatoms selected from O, N, and S;

$R^4$ is $C_{5-9}$aryl or a 5 to 9 membered heteroaryl, wherein said aryl or heteroaryl may be linked to the rest of the compound with a $CH_2$; and wherein $R^4$ may optionally be substituted with 1-3 substituents independently selected from halogen, $C_{1-3}$alkyl, $C_{1-3}$haloalkyl, —$OC_{1-3}$alkyl, CN, and —$C(O)NH_2$;

and wherein each aryl and each heteroaryl includes bicycles and each heteroaryl contains from 1 to 3 heteroatoms selected from O, N, and S.

2. A compound or salt according to claim 1 wherein one of $R^1$ and $R^2$ is H and the other is $C_{1-6}$alkyl, $C_{3-6}$cycloalkyl, $C_{1-3}$alkyl-O—$C_{1-4}$alkylene-, HO—$C_{1-4}$alkylene, phenyl, or pyridyl.

3. A compound or salt according to claim 1 wherein $R^3$ is thiophene, phenyl, indole, indazole, or thiadiazole; optionally substituted with one or two substituents independently selected from, halogen, $C_{1-3}$alkyl, $C_{1-3}$fluoroalkyl, —$OC_{1-3}$alkyl, $C_{2-4}$alkynyl, $C_{2-4}$alkenyl, CN, and —$C(O)NH_2$.

4. A compound or salt according to claim 3 wherein $R^3$ is thiophene or phenyl optionally substituted with one or two substituents independently selected from, halogen and CH3.

5. A compound or salt according to claim 1 wherein $R^4$ is phenyl, pyridyl, pyrimidine, quinoline, tetrahydroquinoline, indazole, or thiazole; optionally substituted with one or two substituents independently selected from, halogen, $C_{1-3}$alkyl, $C_{1-3}$fluoroalkyl, —$OC_{1-3}$alkyl, and CN.

6. A compound or salt according to claim 5 wherein $R^4$ is phenyl, pyridyl, or pyrimidine optionally substituted with one or two substituents independently selected from, halogen, $CH_3$, $CF_3$, —$OCH_3$, and CN.

7. A compound or salt according to claim 1 wherein one of $R^1$ and $R^2$ is H and the other is $C_{1-6}$alkyl, $C_{3-6}$cycloalkyl, $C_{1-3}$alkyl-O—$C_{1-4}$alkylene-, HO—$C_{1-4}$alkylene, phenyl, or pyridyl; $R^3$ is thiophene, phenyl, indole, indazole, or thiadiazole; optionally substituted with one or two substituents independently selected from, halogen, $C_{1-3}$alkyl, $C_{1-3}$fluoroalkyl, —$OC_{1-3}$alkyl, $C_{2-4}$alkynyl, $C_{2-4}$alkenyl, CN, and —$C(O)NH_2$; and $R^4$ is phenyl, pyridyl, pyrimidine, quinoline, tetrahydroquinoline, indazole, or thiazole, wherein said phenyl, pyridyl, pyrimidine, quinoline, tetrahydroquinoline, or thiazole may be linked to the rest of the compound with a $CH_2$; optionally substituted with one or two substituents independently selected from, halogen, $C_{1-3}$alkyl, $C_{1-3}$fluoroalkyl, —$OC_{1-3}$alkyl, and CN.

8. A compound or salt according to claim 7 wherein $R^3$ is thiophene or phenyl, optionally substituted with one or two substituents independently selected from, halogen and $CH_3$; and $R^4$ is phenyl, pyridyl, or pyrimidine optionally substituted with one or two substituents independently selected from, halogen, $CH_3$, $CF_3$, —$OCH_3$, and CN.

9. A pharmaceutical composition comprising a compound or salt according to claim 1.

10. A pharmaceutical composition according to claim 9 wherein said composition is a unit dosage form.

11. A unit dosage form according to claim 10 wherein said unit dosage form is a tablet.

12. A method of treating a disease or condition that would benefit from inhibition of IDO1, wherein said disease or condition is chronic viral infection; chronic bacterial infections; cancer; sepsis; or a neurological disorder, comprising the step of administration of a composition according to claim 11.

13. The method of claim 12 wherein in said disease or condition, biomarkers of IDO activity are elevated.

14. The method of claim 12 wherein said biomarkers are plasma kynurenine or the plasma kynurenine/tryptophan ratio.

15. The method of claim 12 wherein said chronic viral infections are those involving HIV, HBV, or HCV; said chronic bacterial infections are tuberculosis or prosthetic joint infection; and said neurological disorders are major depressive disorder, Huntington's disease, or Parkinson's disease.

16. The method of claim 15 wherein said disease or condition is inflammation associated with HIV infection; chronic viral infections involving hepatitis B virus or hepatitis C virus; cancer; or sepsis.

* * * * *